United States Patent [19]

Sofia

[11] Patent Number: 5,352,690
[45] Date of Patent: Oct. 4, 1994

[54] 1,2,4-TRIOXYGENATED BENZENE DERIVATIVES USEFUL AS LEUKOTRIENE ANTAGONISTS

[75] Inventor: Michael J. Sofia, Carmel, Ind.

[73] Assignee: Eli Lilly and Company, Indianapolis, Ind.

[21] Appl. No.: 907,492

[22] Filed: Jul. 1, 1992

[51] Int. Cl.$^5$ .................. C07D 257/06; C07D 311/74; A61K 31/41; A61K 31/37

[52] U.S. Cl. ................... 514/381; 514/458; 548/253; 549/402

[58] Field of Search ............... 548/253; 514/381, 458; 549/402

[56] References Cited

U.S. PATENT DOCUMENTS

| | | | |
|---|---|---|---|
| 3,882,148 | 5/1975 | Augstein et al. | 260/345.2 |
| 3,899,513 | 8/1975 | Warren et al. | 260/345.2 |
| 4,424,231 | 1/1984 | Bantick et al. | 424/274 |
| 4,665,203 | 5/1987 | Miyano et al. | 549/402 |
| 4,889,871 | 12/1989 | Djuric et al. | 514/456 |
| 4,945,099 | 7/1990 | Bollinger et al. | 514/381 |
| 4,996,230 | 2/1991 | Gapinski | 514/454 |

FOREIGN PATENT DOCUMENTS

| | | |
|---|---|---|
| 056172 | 7/1982 | European Pat. Off. |
| 061800 | 10/1982 | European Pat. Off. |
| 256532 | 2/1988 | European Pat. Off. |
| WO91/17160 | 11/1991 | PCT Int'l Appl. |

OTHER PUBLICATIONS

Djuric et al., *J. Med. Chem.*, 32, 1145–1147 (1989).
Tsai et al., *Prostaglandins*, 38, 655–674 (1989).
Fretland et al., *Prostaglandins, Leukotrienes and Essential Fatty Acids*, 88, 169–172 (1989).
Fretland et al., *Agents and Actions*, 27, 395–397 (1989).
Showell et al., *Biochem. Biophys. Res. Commun.*, 106, 741–747 (1982).
Nakamura et al., *Chem. Pharm. Bull.*, 35, 2635–2645 (1987).
Morris et al., *Tet. Let.*, 29, 143–146 (1988).
Namiki et al., *Biochem. Biophys. Res. Commun.*, 138, 546 (1986).
Lin et al., *Ann. N.Y. Academy of Sci.*, 524, 196–200 (1988).

*Primary Examiner*—David B. Springer
*Attorney, Agent, or Firm*—Roger S. Benjamin; John C. Demeter

[57] ABSTRACT

This invention provides 1,2,4-trioxygenated benzene derivatives which are leukotriene B$_4$ antagonists, formulations of those derivatives, and a method of using those derivatives for the treatment of conditions characterized by an excessive release of leukotrienes.

23 Claims, No Drawings

1,2,4-TRIOXYGENATED BENZENE DERIVATIVES USEFUL AS LEUKOTRIENE ANTAGONISTS

BACKGROUND OF THE INVENTION

Research in the area of allergic reactions of the lung has provided evidence that arachidonic acid derivatives formed by the action of lipoxygenases are related to various disease states. Some of these arachidonic acid metabolites have been classified as members of a family of eicosatetraenoic acids termed leukotrienes. Three of these substances are currently thought to be major components of what has been previously called slow reacting substance of anaphylaxis (SRS-A) and have been designated leukotrienes $C_4$, $D_4$, and $E_4$ ($LTC_4$, $LTD_4$, and $LTE_4$, respectively).

Another arachidonic acid metabolite, leukotriene $B_4$ ($LTB_4$), is a proinflammatory lipid which has been implicated in the pathogenesis of psoriasis, arthritis, chronic lung diseases, acute respiratory distress syndrome, shock, asthma, inflammatory bowel diseases, and other inflammatory states characterized by the infiltration and activation of polymorphonuclear leukocytes and other proinflammatory cells. Thus activated, the polymorphonuclear leukocytes liberate tissue-degrading enzymes and reactive chemicals causing the inflammation. Antagonism of $LTB_4$ should therefore provide a novel therapeutic approach to treatment of these conditions.

It is the object of this invention to provide novel chemical agents which are selective leukotriene $B_4$ antagonists that can be used therapeutically in the treatment of inflammation and allergic disorders such as asthma, where leukotrienes are thought to be causal mediators.

SUMMARY OF THE INVENTION

This invention provides compounds of the Formula I

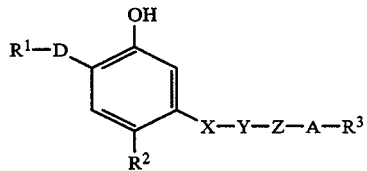

or a pharmaceutically acceptable base addition salt thereof, wherein

D is O or S;

$R^1$ is $C_1$-$C_{10}$ alkyl, $C_3$-$C_8$ cycloalkyl, or ($C_1$-$C_4$ alkyl)phenyl having 0 to 3 of the same or different substituents on the phenyl ring selected from halo, $C_1$-$C_4$ alkyl, $C_1$-$C_4$ alkoxy, trifluoromethyl, or di($C_1$-$C_4$ alkyl)amino;

$R^2$ is $C_1$-$C_5$ alkyl, $C_2$-$C_5$ alkenyl, $C_2$-$C_5$ alkynyl, $C_1$-$C_4$ alkoxy;

X is —O—, —S—, —C(=O)—, or —$CH_2$—;

Y is —O— or —$CH_2$—;

or when taken together, —X—Y— is —CH=CH— or —C≡C—

Z is a bond or straight or branched chain $C_1$-$C_{10}$ alkylidenyl;

A is a bond, —O—, —S—, —CH=CH—, or —$CR_aR_b$—, where $R_a$ and $R_b$ are each independently hydrogen, $C_1$-$C_5$ alkyl, or $R^6$-substituted phenyl, or when taken together with the carbon atom to which they are attached form a $C_4$-$C_8$ cycloalkyl ring;

$R^{3'}$ is $R^{4'}$,

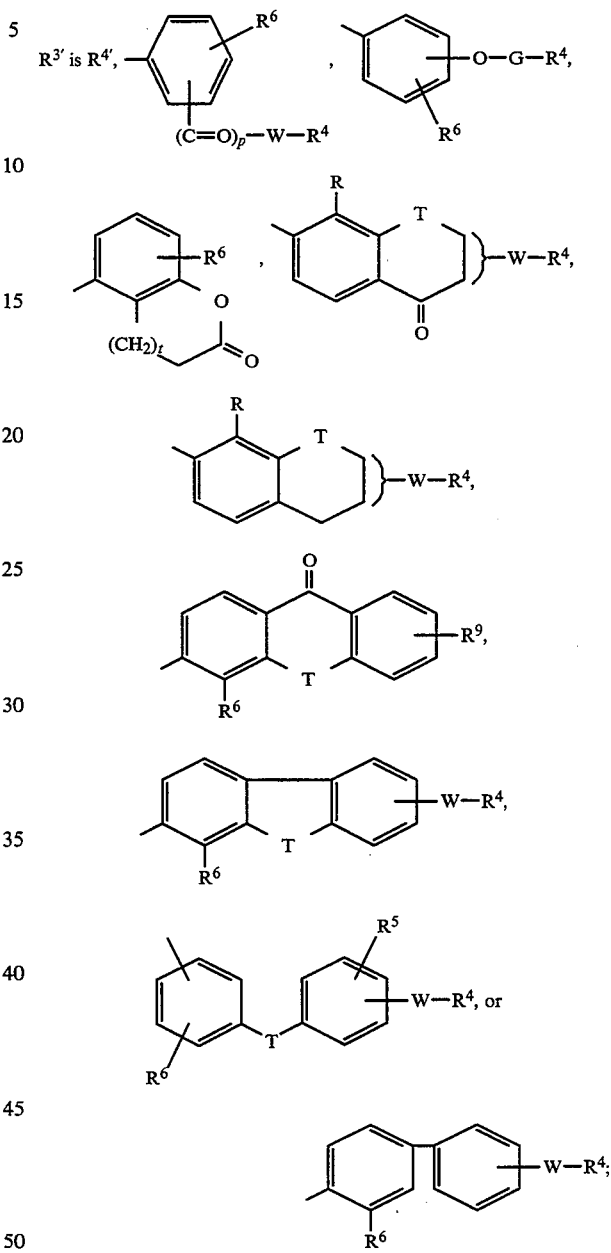

where
each R is independently hydrogen or $C_1$-$C_4$ alkyl;

each $R^4$ is independently —COOH, 5-tetrazolyl, —CON($R^7$)$_2$, or —CONHSO$_2R^8$;

$R^5$ is hydrogen or halo;

each $R^6$ is hydrogen, $C_1$-$C_4$ alkyl, $C_2$-$C_5$ alkenyl, $C_2$-$C_5$ alkynyl, benzyl, methoxy, —W—$R^4$, —T—G—$R^4$, ($C_1$-$C_4$ alkyl)—T—($C_1$-$C_4$ alkylidenyl)—O—, or hydroxy;

each R is independently hydrogen, phenyl, or $C_1$-$C_4$ alkyl, or when taken together with the nitrogen atom form a morpholino, piperidino, piperazino, or pyrrolidino group;

$R^8$ is $C_1$-$C_4$ alkyl or phenyl;

$R^9$ is hydrogen, halo, hydroxy, $C_1$-$C_4$ alkyl, $C_1$-$C_4$ alkoxy, ($C_1$-$C_4$ alkyl)—S(O)$_q$—, trifluoromethyl, or di($C_1$-$C_3$ alkyl)amino, —W—$R^4$, or —T—G—$R^4$;

each W is a bond or a straight or branched chain divalent hydrocarbyl residue of one to eight carbon atoms;

each G is a straight or branched chain divalent hydrocarbyl residue of one to eight carbon atoms;

each T is a bond, —CH$_2$—, —O—, —NH—, —NH-CO—, —C(=O)—, or —S(O)$_q$—;

each q is independently 0, 1, or 2;

p is 0 or 1; and t is 0 or 1;

provided when X is —O— or —S—, Y may not be —O—;

provided Z and A may not both be a bond when Y is —O—;

provided when A is —O— or —S—, R$^3$ may not be R$^4$;

provided when A is —O— or —S— and Z is a bond, Y may not be —O—;

provided Z may not be a bond when Y is —O—;

and provided W may not be a bond when p is 0.

Further provided by this invention is a method for treating immediate hypersensitivity conditions such as inflammation or asthma comprising the administration of an effective amount of a compound of Formula I.

This invention also provides pharmaceutical formulations which comprise as an active ingredient a compound of this invention as defined above associated with a pharmaceutically acceptable carrier therefor.

DETAILED DESCRIPTION AND PREFERRED EMBODIMENT

The present invention relates to new organic compounds that are useful in the treatment of conditions and diseases associated with the excessive release of leukotriene B$_4$. A preferred group of compounds are the compounds of Formula Ia:

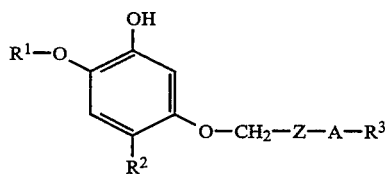

and pharmaceutically acceptable base addition salts thereof. Especially preferred are those compounds wherein R$_1$ is C$_1$-C$_6$ alkyl, or C$_5$-C$_6$ cycloalkyl and R$^2$ is C$_1$-C$_4$ alkyl.

Preferred Z substituents include C$_2$-C$_4$ alkylidene, particularly —CH$_2$CH$_2$— and —CH$_2$CH$_2$CH$_2$CH$_2$—. Preferred A groups include —O—, —CH$_2$—, and —C(CH$_3$)$_2$—. Preferred R$^3$ groups include —COOH, 5-tetrazolyl, or a mono-, bi-, or tri-cyclic group as drawn above wherein there is at least one acidic group attached to a ring, such as —W—COOH, —T—G—COOH, or the corresponding tetrazole derivatives. The preferred W moiety is that of a bond or straight chain C$_1$-C$_4$ alkylidene; preferred G moieties are straight chain C$_1$-C$_4$ alkylidene. It is preferred that R or R$^6$ be C$_1$-C$_4$ alkyl, especially n-propyl.

Particularly preferred groups are those wherein A is —O— or —C(CH$_3$)$_2$— and R$^3$ is 5-tetrazolyl or a chromanyl carboxylic acid having the structure

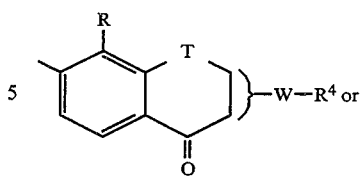

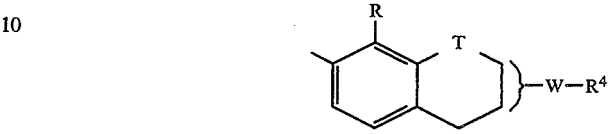

where

R is n-propyl,

T is —O—,

W is a bond, and

R$^4$ is —COOH or 5-tetrazolyl.

The following definitions refer to the various terms used throughout this disclosure. The term "C$_1$-C$_{10}$ alkyl" refers to the straight and branched aliphatic radicals of 1 to 10 carbon atoms such as methyl, ethyl, propyl, isopropyl, n-butyl, sec-butyl, tert-butyl, n-pentyl, 2,2-dimethylpropyl, hexyl, and the like. Included within this definition are the terms "C$_1$-C$_3$ alkyl", "C$_1$-C$_4$ alkyl" and "C$_1$-C$_5$ alkyl". The term "C$_2$-C$_5$ alkenyl" refers to straight and branched aliphatic radicals of 2 to 5 carbon atoms containing one double bond, such as —CH=CH$_2$, —CH$_2$CH=CH$_2$, —CH$_2$CH$_2$CH=CH$_2$, —CH$_2$C(CH$_3$)=CH$_2$, —CH$_2$CH=C(CH$_3$)$_2$, and the like. The term "C$_2$-C$_5$ alkynyl" refers to straight and branched aliphatic residues of 2 to 5 carbon atoms containing one triple bond, such as —C≡CH, —CH$_2$—C≡CH, —CH$_2$CH$_2$C≡CH, —CH$_2$CH(CH$_3$)C≡CH, —CH$_2$C≡CCH$_3$ and the like. The term "C$_1$-C$_4$ alkoxy" refers to methoxy, ethoxy, propoxy, isopropoxy, butoxy, sec-butoxy, and tert-butoxy. The term "halo" refers to fluoro, chloro, bromo, and iodo.

The term "C$_1$-C$_{10}$ alkylidene" refers to a divalent radical derived from a C$_1$-C$_{10}$ alkane such as —CH$_2$—, —CH(CH$_3$)—, —C(CH$_3$)$_2$—, —CH(C$_2$H$_5$)—, —CH$_2$CH$_2$—, —CH$_2$CH(CH$_3$)—, —CH(CH$_3$)CH$_2$—, —CH(CH$_3$)CH(CH$_3$)—, —CH$_2$C(CH$_3$)$_2$, —CH$_2$CH(C$_2$H$_3$)—, —CH$_2$CH$_2$CH$_2$—, —CH(CH$_3$)CH$_2$CH$_2$—, —CH$_2$CH(CH$_3$)CH$_2$—, —CH$_2$CH(C$_2$H$_5$)CH$_2$—, —CH$_2$CH$_2$CH(C$_2$H$_5$)—, —C(CH$_3$)$_2$CH$_2$CH$_2$—, —CH(CH$_3$)CH$_2$CH(CH$_3$)—, —CH$_2$CH$_2$CH$_2$CH$_2$—, —CH$_2$C(CH$_3$)$_2$CH$_2$CH$_2$—, —CH$_2$C(CH$_3$)$_2$CH$_2$—, —CH$_2$CH$_2$CH(C$_2$H$_5$)CH$_2$—, —CH$_2$CH$_2$CH$_2$CH$_2$CH$_2$—, —CH(CH$_3$)CH$_2$CH$_2$CH$_2$CH$_2$—, —CH$_2$CH$_2$CH$_2$CH$_2$CH$_2$CH$_2$—, —(CH$_2$)$_{10}$—, and the like. Included within this definition are the terms "C$_1$-C$_4$ alkylidene" and "C$_2$-C$_4$ alkylidene".

The term "C$_3$-C$_8$ cycloalkyl" refers to a cycloalkyl ring of three to eight carbon atoms, such as cyclopropyl, cyclobutyl, cyclopentyl, cyclohexyl, 4,4-dimethylcyclohexyl, cycloheptyl, cyclooctyl, and the like.

The term "straight or branched chain divalent hydrocarbyl residue of one to eight carbon atoms" refers to a divalent radical derived from a straight or branched alkane, alkene, or alkyne of one to eight carbon atoms. Depending upon the branching and number of carbon atoms, as will be appreciated by organic chemists, such a moiety can contain one, two or three double or triple bonds, or combinations of both. As such, this term can be considered an alkylidene group as defined above containing from 1 to 8 carbon atoms optionally containing one to three double or triple bonds, or combinations of the two, limited as noted in the preceding sentence.

This invention includes the pharmaceutically acceptable base addition salts of the compounds of Formula I. Such salts include those derived from inorganic bases, such as ammonium and alkali and alkaline earth metal hydroxides, carbonates, bicarbonates, and the like, as well as salts derived from basic organic amines, such as aliphatic and aromatic amines, aliphatic diamines, hydroxy alkylamines, and the like. Such bases useful in preparing the salts of this invention thus include ammonium hydroxide, potassium carbonate, sodium bicarbonate, calcium hydroxide, methyl amine, diethyl amine, ethylene diamine, cyclohexylamine, ethanolamine, and the like. The potassium and sodium salt forms are particularly preferred. This invention includes both monosalt forms, i.e., a 1:1 ratio of a compound of Formula I with a base as previously described, as well as disalt forms in those instances where a compound of Formula I has two acidic groups. In addition, this invention includes any solvate forms of the compounds of Formula I or salts thereof, such as ethanol solvates, hydrates, and the like.

It is recognized that in compounds having branched alkyl, alkylidenyl, or hydrocarbyl functionality, and in those compounds bearing double or triple bonds, various stereoisomeric products may exist. This invention is not limited to any particular stereoisomer but includes all possible individual isomers and mixtures thereof. The term "5-tetrazolyl" refers to both tautomers, i.e., (1 H)-5-tetrazolyl and (2 H)-5-tetrazolyl.

The compounds of this invention may be prepared according to standard methods known in the art. For example, the tetrazole compounds of Formula I (wherein at least one $R^4$ is 5-tetrazolyl) may be prepared from the corresponding nitrile intermediate by any of a variety of standard methods. Generally, the nitrile is reacted with an azide reagent in a non-reactive solvent. Preferred conditions include the use of lithium or ammonium azide in dimethylformamide, sodium azide in diglyme and N,N-dimethylethanolamine hydrochloride, or tri-n-butyltin azide in a non-reactive solvent such as dimethoxyethane or tetrahydrofuran. Under the latter conditions, the reaction is generally heated at or near the reflux temperature of the reaction mixture. The transformation is generally complete under these conditions in 2-3 days. Other operable reaction conditions include the reaction of nitrile with an alkali metal azide such as sodium azide, ammonium chloride, and (optionally) lithium chloride in a non-reactive high-boiling solvent such as N,N-dimethylformamide (DMF), preferably at temperatures from about 60° C. to about 125° C. Alternatively, tri-n-butyltin azide or tetramethylguanidinium azide, in a solvent such as tetrahydrofuran, dimethoxyethane, diethoxyethane, or the like, may be used in place of the alkali metal azide, ammonium chloride, lithium chloride and DMF. Similarly, the acids of this invention (Formula I wherein at least one $R^4$ is —COOH) are prepared from the corresponding —COO($C_1$-$C_4$alkyl) or —CN intermediates. Hydrolysis of such esters or nitriles may be accomplished by any of a variety of acidic or basic conditions, preferably under aqueous conditions. Preferred methods involve the use of lithium hydroxide in a solvent mixture of acetone/water, sodium hydroxide in dioxane, or potassium hydroxide or potassium carbonate in a mixture of methanol/water. Under the former conditions, hydrolysis is generally complete in about 12-18 hours at temperatures from about 20°-30° C. whereas the latter reaction is usually complete in one hour at 20°-30° C.

It is generally preferred, in compounds containing both a nitrile and an ester functionality, that the nitrile group be transformed into a tetrazole before hydrolysis of the ester.

The compounds of Formula I, or their precursors can be prepared according to the following processes.

Scheme 1

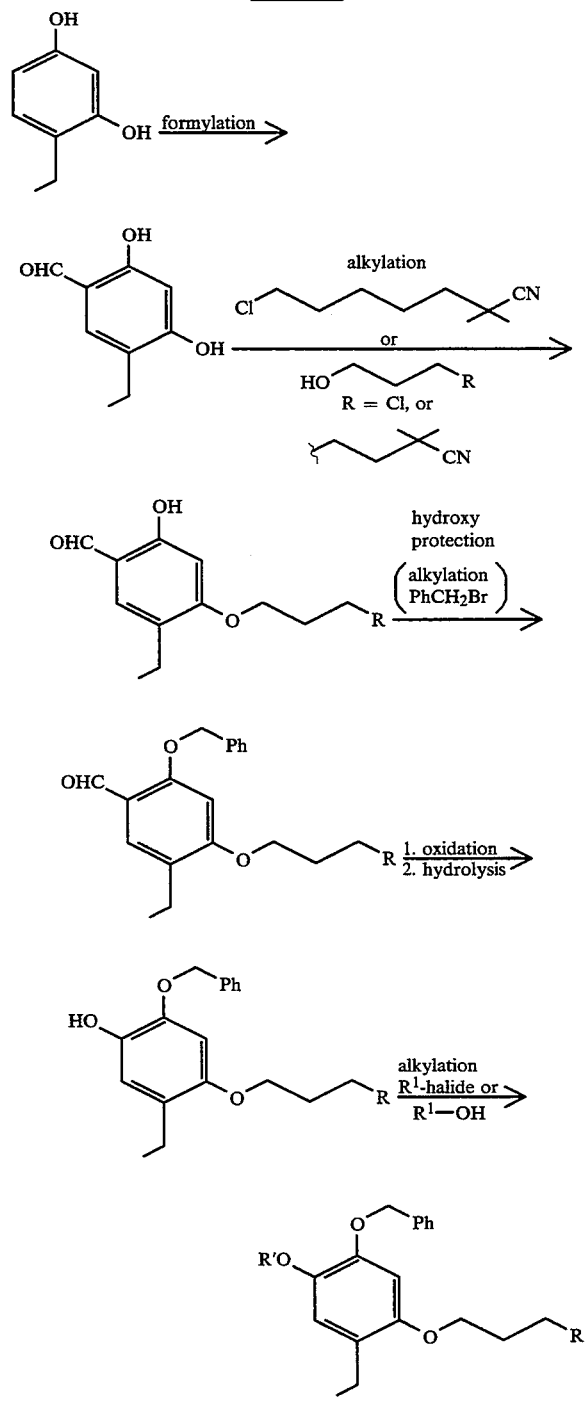

Scheme 2
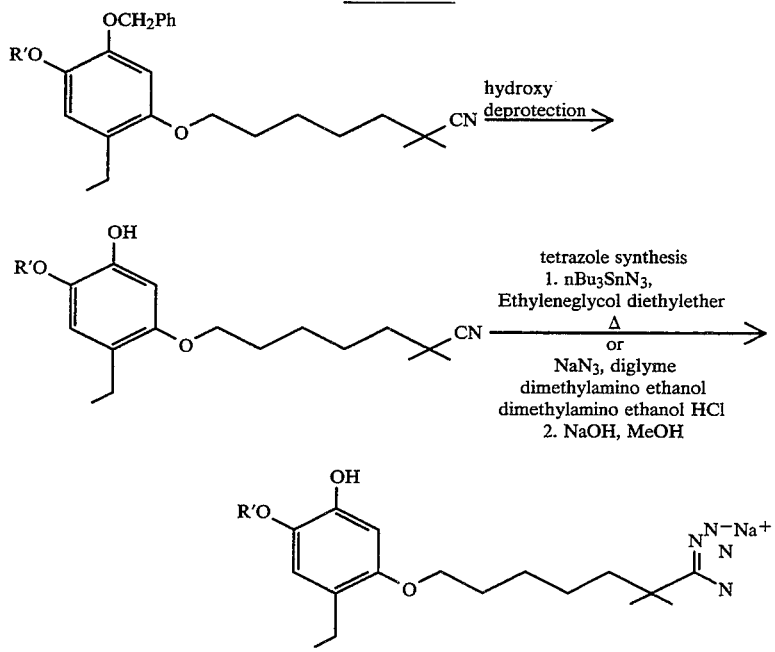
Scheme 3
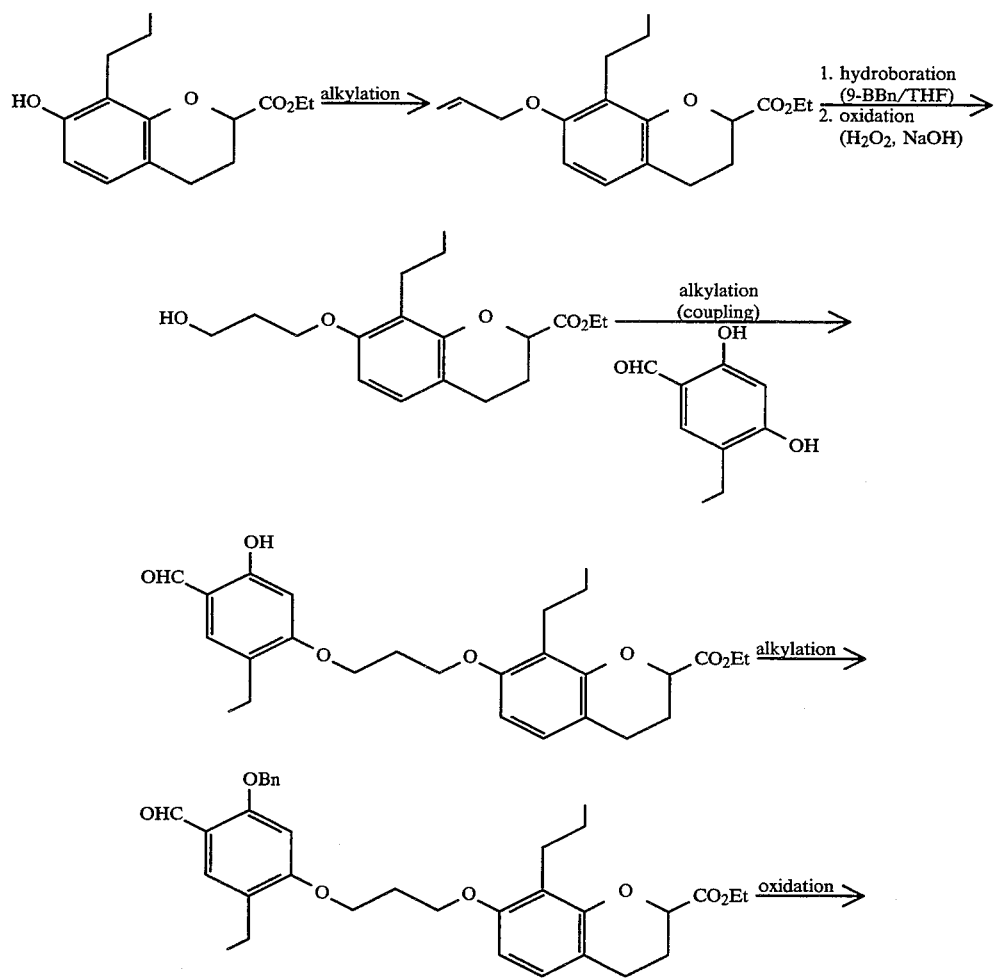

-continued
Scheme 3
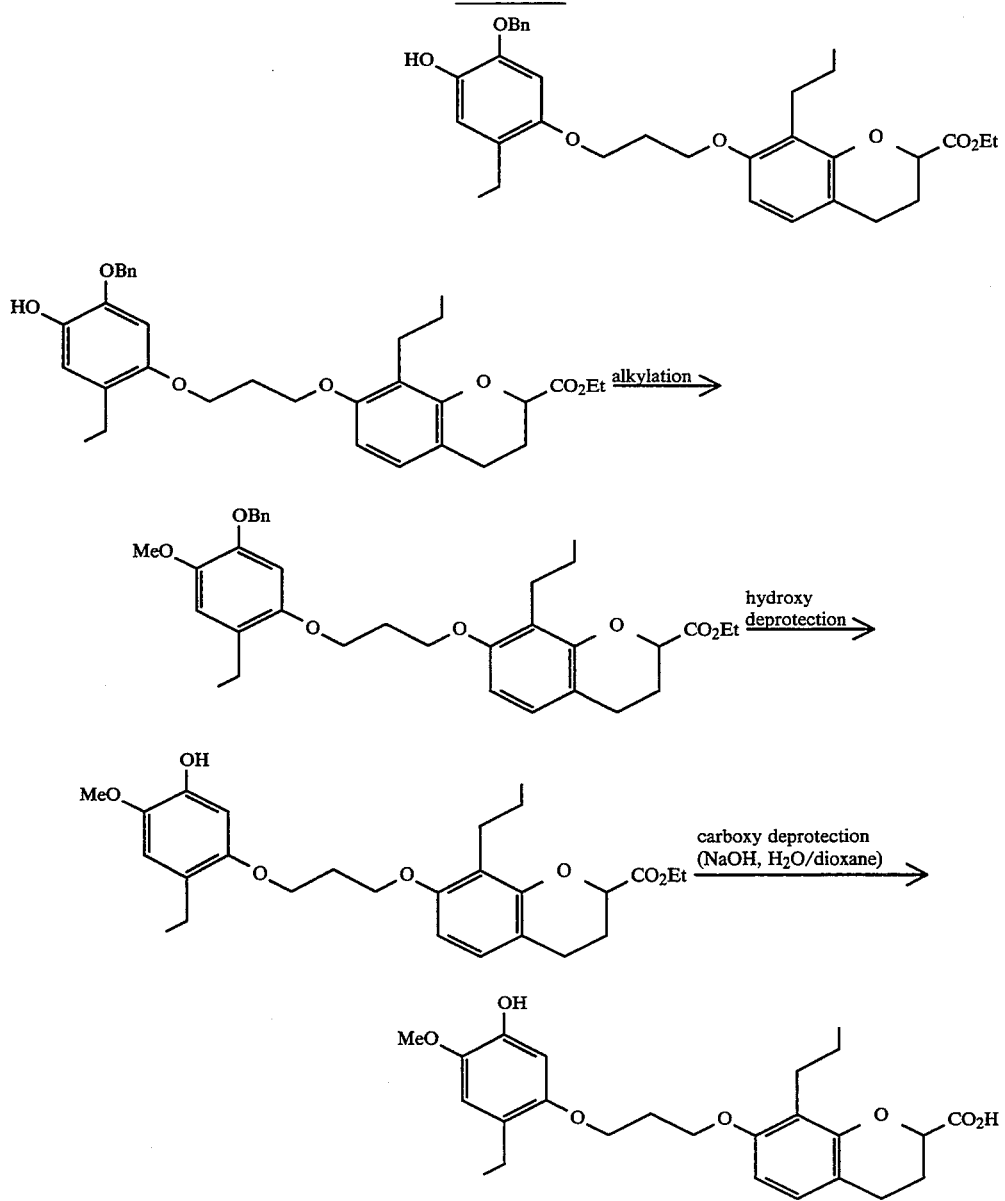
Scheme 4
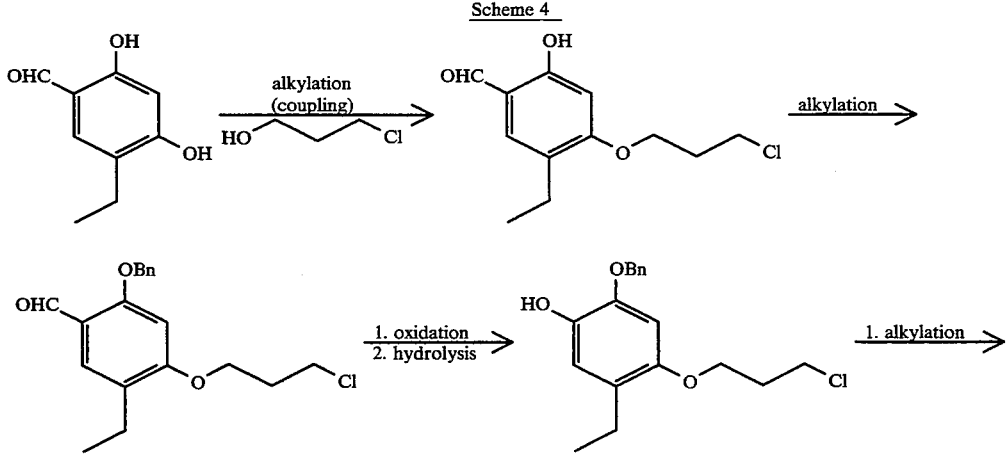

Scheme 4
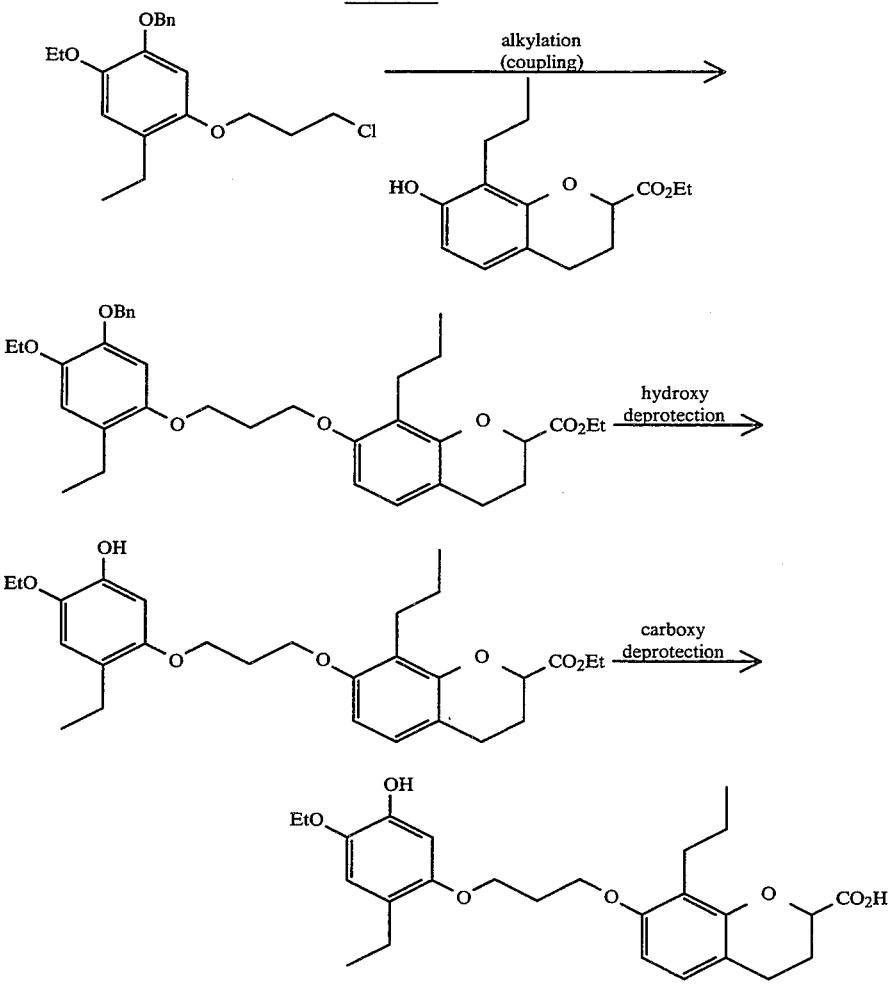
Scheme 5
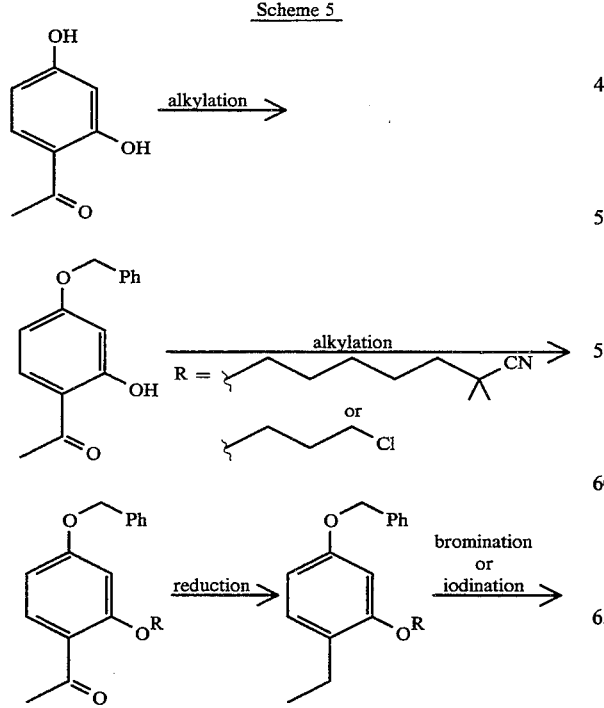
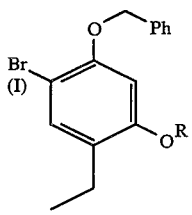
Scheme 6
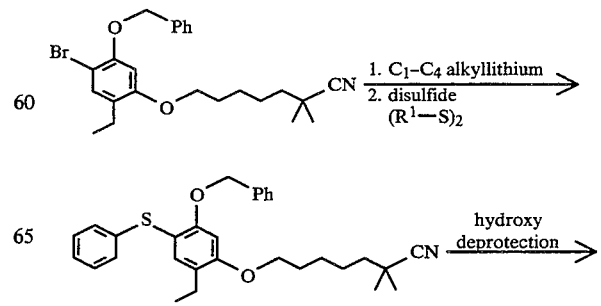

-continued
Scheme 6

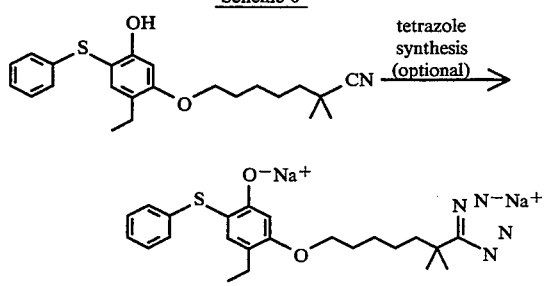

In scheme 1, a 4-substituted resorcinol is formylated with dimethyl formamide (DMF) in the presence of phosphorous oxychloride (POCl₃) in an inert or substantially inert solvent or mixture of solvents to afford the corresponding 2,4-dihydroxy-5-substituted benzaldehyde. Generally equivalent amounts of resorcinol and DMF to a slight excess of DMF are used. Suitable solvents are chlorinated polar solvents, preferably $CH_2Cl_2$.

The benzaldehyde thus afforded is alkylated (coupled) at the 4-position by combining the reactants in an organic base such as $K_2CO_3$ or NaH in the presence or absence of a metal halide in an inert or substantially inert solvent or mixture of solvents to afford the corresponding 2-hydroxy-4-substituted-5-substituted benzaldehyde. Generally, 2 equivalents to a slight excess of inorganic base are used and a catalytic amount of metal halide, if used. The preferred inorganic base is $H_2CO_3$. It is preferred that a metal halide be present and the preferred metal halides are NaI and KI. Suitable solvents are polar solvents such as DMF, methyl ethylketone, and DMSO, with DMF being preferred. Preferably, this reaction is carried out at temperatures of from about 75° C. to about 125° C.

Alternatively, alkylation of the benzaldehyde is carried out using a Mitsunobu reaction. Generally, this is a alkylative coupling reaction between alcohols on treatment with diethyl azodicarboxylate (DEAD) and triphenyl phosphine or trialkylphosphine in an etheral solvent, such as tetrahydrofuran (THF), dimethyl ether (DME) and diethyl ether. The preferred solvent is THF.

The 2-hydroxy-4-substituted-5-substituted benzaldehyde is then alkylated at the 2-position by reacting it with benzyl halide in an inorganic base, such as $H_2CO_3$ or NaH, in a polar aprotic solvent such as DMF, MEK and DMSO at a temperature of from about 50° C. to about 100° C., to afford the corresponding 2-benzyloxy-4-substituted-5-substituted benzaldehyde. Equivalent amounts to a slight excess of benzyl halide, preferably benzyl bromide, is used. The preferred solvent is DMF. When sodium hydride is used, it is necessary to add a catalytic amount of 18-crown-6 ether and the reaction carried out at about room temperature.

The benzaldehyde thus afforded is oxidized to the corresponding formate ester in a Baeyer-Villiger reaction. Preferably, the peracid is m-chloroperbenzoic acid. Generally, polar chlorinated solvents are used, and preferably $CH_2Cl_2$. The formate ester is then hydrolyzed with an aqueous inorganic base, preferably aqueous NaOH in apolar solvent, preferably THF, to afford the corresponding phenol.

The phenol thus afforded is then alkylated using substantially the same procedures and conditions described above for analagous alkylation reactions, using an appropriate $R^1$-halide or $R^1$-OH group to afford a corresponding 1,2,4-trioxygenated benzene derivative.

In Scheme 2, the 2-hydroxy group of the 1,2,4-trioxygenated benzene derivative from Scheme 1 is deprotected. As will be appreciated by skilled artisans in the field, the means for deprotecting the hydroxy group will depend upon the choice of protecting group employed. In the preferred situation where a benzyl group is used, the benzyl group is removed by catalytic hydrogenation, for example using 10% palladium on carbon and hydrogen gas in an inert or substantially inert solvent or mixture of solvents, preferably ethyl acetate or methanol. Alternatively, boron trihalide, preferably boron tribromide in a polar chlorinated solvent, preferably methylene chloride, is used to effect deprotection after removal of the benzyl protecting group the tetrazole compounds of Formula I (wherein at least one $R^4$ is 5-tetrazolyl) may be prepared from the corresponding nitrile intermediate by any of a variety of standard methods. Generally, the nitrile is reacted with an azide reagent in a non-reactive solvent. Preferred conditions include the use of lithium or ammonium azide in dimethylformamide, sodium azide in diglyme and N,N-dimethylethanolamine hydrochloride, or tri-n-butyltin azide in a non-reactive solvent such as dimethoxyethane or tetrahydrofuran. Under the latter conditions, the reaction is generally heated at or near the reflux temperature of the reaction mixture. The transformation is generally complete under these conditions in 2–3 days. Other operable reaction conditions include the reaction of the nitrile with an alkali metal azide such as sodium azide, ammonium chloride, and (optionally) lithium chloride in a non-reactive high-boiling solvent such as N,N-dimethylformamide (DMF), preferably at temperatures from about 60° C. to about 125° C. Alternatively, tri-n-butyltin azide or tetramethylguanidinium azide, in a solvent such as tetrahydrofuran, dimethoxyethane, diethoxyethane, or the like, may be used in place of the alkali metal azide, ammonium chloride, lithium chloride and DMF. Similarly, the acids of this invention (Formula I wherein at least one $R^4$ is —COOH) are prepared from the corresponding —COOR or —CN intermediates. Hydrolysis of such esters or nitriles may be accomplished by any of a variety of acidic or basic conditions, preferably under aqueous conditions. Preferred methods involve the use of lithium hydroxide in a solvent mixture of acetone/water, sodium hydroxide in dioxane, or potassium hydroxide or potassium carbonate in a mixture of methanol/water. Under the former conditions, hydrolysis is generally complete in about 12–18 hours at temperatures from about 20°–30° C. whereas the latter reaction is usually complete in one hour at 20°–30° C.

It is generally preferred, in compounds containing both a nitrile and an ester functionality, that the nitrile group be transformed into a tetrazole before hydrolysis of the ester.

In Scheme 3, the synthetic procedures for preparing a methoxy chroman compound of Formula I are set forth. This Scheme is set forth for illustrative purposes of other alkoxy chromans within the scope of the present invention. The alkylation, alkylative coupling, oxidation and hydroxy deprotection reactions are carried out using procedures and under conditions described above in Schemes 1 and 2 for analogous reactions. The hydroboration reaction is carried out under known conditions for such a reaction. The preferred organoborone reagent is 9-BBN. Suitable solvents are etheral and preferred is THF. The corresponding alcohol is prepared by reacting the organoborone intermediate with a basic peroxide. The preferred basic peroxide is $H_2O_2$ in aqueous NaOH.

The conditions for carboxy deprotection will, of course, depend on the carboxy protecting group employed. In the preferred situation where a $C_1$-$C_4$ alkyl group is used, the alkyl group is removed by basic hydrolysis using aqueous sodium hydroxide in dioxane.

In Scheme 4, the synthetic procedures employed for preparing an ethoxy chorman compound of Formula I is set forth. This Scheme is described for illustrative purposes of other alkoxy chromans within the scope of the present invention and as an alternative to the Scheme 3 procedures. The alkylative coupling, alkylation, oxidation, coupling, hydroxy deprotection and carboxy deprotection reactions are carried out using procedures and under conditions described above in Schemes 1, 2 and 3 for analagous reactions.

In Scheme 5, synthetic procedures for preparing aryl bromide intermediates are shown. The alkylation reactions are carried-out using substantially the same procedures and conditions described above in Schemes 1 and 2 for analogous reactions. The reduction is carried out by treatment with a $C_1$-$C_4$ trialkylsilane, preferably triethylsilane, and trifluoroacetic acid in a haloalkane solvent, preferably carbon tetrachloride.

The iodination is carried out by treatment with a suitable iodinating agent, preferably iodine and silver acetate in a suitable solvent, preferably acetic acid. Bromination, which is preferred, is carried out by treatment with a suitable brominating agent, preferably N-bromosuccinimide, in a solvent, preferably carbon tetrachloride to afford the desired aryl bromide intermediate. This intermediate can then be transformed into various intermediates and final products of this invention by methods previously described or by the methods shown in Scheme 6 and described below.

In Scheme 6, methods for preparing the thioether compounds of the present invention are illustrated. Although illustrated with fixed groups, it should be appreciated the methods are broadly applicable to the thioether compounds of Formula I. The hydroxy deprotection and optional tetrazole synthesis are carried out using substantially the same procedures and conditions described above in Schemes 1 and 2 for analagous reactions. The metal-halogen exchange reaction is carried out by sequentially treating the bromo (or iodo) intermediate with a $C_1$-$C_4$ alkyllithium reactant and then with the appropriate disulfide (phenyl disulfide shown for illustrative purposes). Suitable solvents for this reaction are aprotic ethers such as diethyl ether and preferably tetrahydrofuran (THF). This reaction is carried out at temperatures of from about $-100°$ C. to about $-40°$ C., preferably between about $-55°$ C. and about $-85°$ C.

In addition, various compounds of Formula I can be prepared from other compounds, precursors, or intermediates of Formula I by standard methods such as hydrolysis, esterification, alkylation, oxidation, reduction, and the like, as are well known to those skilled in the art. The Schemes noted above are illustrative of the more conventional methods for preparing the compounds of this invention. However, different combinations of these chemical steps and others generally known in the organic chemistry art can effectively be employed; the particular sequence of any such transformations and interconversions will be appreciated by experienced organic chemists in view of the various functional groups to be present in the compound of choice. For example, a tetrazole group can be protected with a group such as trityl; other chemistry can be performed on the remaining portion of the molecule, and the trityl group removed upon treatment with dilute acid to give the unprotected tetrazole. Other variations of this and related transformations will be apparent to skilled artisans in this field.

The following preparations and examples further illustrate the preparation of the intermediates and compounds of this invention. The examples are illustrative only and are not intended to limit the scope of the invention. Melting points were determined on a Thomas-Hoover apparatus and are uncorrected. NMR spectra were determined on a GE QE-300 spectrometer. All chemical shifts are reported in parts per million ($\delta$) relative to tetramethylsilane. The following abbreviations are used to denote signal patterns: s=singlet, d=doublet, t=triplet, q=quartet, b=broad, m=multiplier. Infrared spectra were determined on a Nicolet DX10 FT-IR spectrometer. Mass spectral data were determined on a CEC-21-110 spectrometer using electron impact (EI) conditions, a MAT-731 spectrometer using field desorption (FD) conditions, or a VG ZAB-3F spectrometer using fast atom bombardment (FAB) conditions. Silica gel chromatography was performed using ethyl acetate/hexane gradients unless otherwise indicated. Reverse-phase chromatography was performed on MCI CHP20P gel using an acetonitrile/water or methanol/water gradient unless otherwise indicated. Tetrahydrofuran (THF) was distilled from sodium/benzophenone ketyl immediately prior to use. All reactions were conducted under argon atmosphere with stirring unless otherwise noted. Where structures were confirmed by infra-red, proton nuclear magnetic resonance, or mass spectral analysis, the compound is so designated by "IR", "NMR", or "MS", respectively.

EXAMPLE 1

Preparation of 4-Ethyl-2-methoxy-5-[[6-methyl-6-(2H-tetrazol-5-yl)heptyl]oxy] phenol sodium salt, a compound represented by the formula:

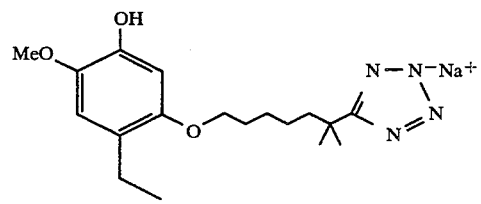

A. Preparation of 5-Ethyl-2,4-Dihydroxybenzaldehyde.

Dimethyformamide (250 mL) was cooled to 0° C. under argon atmosphere. With stirring, $POCl_3$ (18.60 mL, 0.20 mol) was added slowly to the DMF. After several minutes at 0° C., the reaction was warmed to room temp and $CH_2Cl_2$ (150 mL) was added to the reaction mixture to dissolve the solid. The reaction was subsequently recooled to 0° C. 4-Ethylresorcinol (25.0 g, 0.181 mol) was added to the reaction mixture as a 200 mL $CH_2Cl_2$ solution. After stirring at 0° C. for 10 min., the reaction was warmed to room temp and then refluxed for 16 h. The reaction was cooled to room temp, and a 100 mL water solution of NaOAc (50 g) was added slowly. This mixture was refluxed for 40 min then cooled to room temp. The aqueous layer was washed several times with $CH_2Cl_2$. The organics were combined and washed with 1N HCl solution and brine the dried over $MgSO_4$. Filtration and solvent removal gave an orange solid which was recrystallized from toluene and hexane (17 g, 56%)

TLC Rf=0.39 (30% EtOAc/Hexane)

$^1$HNMR($CDCl_3$)δ11.30(s,1), 9.71(s,1), 7.29(s,1), 6.36(s(br), 1), 2.61(q,2,J=7.48 Hz), 1.25(t,3,J=7.54 Hz)

B. Preparation of 1-[6-Methyl-6-cyanoheptyloxy]-2-ethyl-4-formyl-5-hydroxy benzene.

To a mixture of 5-ethyl-2,4-dihydroxybenzaldehyde (10.05 g, 0.060 mol), $H_2CO_3$ (14.63 g, 0.105 mol), KI (2.51 g, 0.015 mol) and DMF (250 mL), added a 250 mL solution of the chloronitrile (10.45 g, 0.060 mol) and warmed to 100° C. After 5 h, the reaction was cooled to room temp and the DMF was removed by vacuum distillation at 4 mmHg. The resulting brown oil was dissolved in EtOAc and washed with water and brine. The EtOAc extract was dried over $MgSO_4$ and filtered. Solvent removal gave 17.0 g of a brown oil. The oil was purified by flash chromatography on silica gel eluting with 15% EtOAc/hexane. The desired product was obtained as a clear oil (6.98 g, 38%).

TLC Rf=47 (30% EtOAc/Hexane)

$^1$HNMR($CDCl_3$)δ11.44(s,1), 9.67(s,1), 7.22(s,1), 6.36(s,1), 4.02(t,2,J=6.22 Hz), 2.56(q,2,J=7.52 Hz), 1.85(m,2), 1.55(s(br), 6), 1.34(s,6), 1.18(t,3,J=7.50 Hz)

IR ($CHCl_3$) 2980, 2944, 2860, 2230, 1640, 1585, 1493 $cm^{-1}$

Mass Spec(FD) m/e 303 (M+)

Elem Anal Calc'd for $C_{18}H_{25}NO_3$:

C,71.26; H, 8.31; N,4.62;

Found C,71.39; H, 8.10; N,4.75.

C. Preparation of 1-Benzyloxy-3-(6-cyano-6-methyl-heptyloxy)-4-ethyl-6-formyl benzene.

A solution of 40 mL of dry DMF, 1-[6-Methyl-6-cyanoheptyloxy]-2-ethyl-4-formyl-5-hydroxy benzene (3.05 g, 10.7 mmol) and $H_2CO_3$ (2,43 g, 17.6 mmol) were stirred at room temp. To this mixture was added benzylbromide (3.66 g, 21.4 mmol), and the reaction was warmed to 75° C. After 19 h the reaction was cooled to room temp. and the solids were removed by filtration. The DMF was removed from the filtrate by vacuum distillation at 6 mHg, and the resulting material was dissolved in EtOAc and washed with water and brine. The organic layer was dried over $MgSO_4$. Filtration and solvent removal gave a white solid (4.52 g). The solid was recrystallized from $Et_2O$/Hexane to give 3.42 g (82%) of white flakes.

TLC Rf=0.40 (30% EtOAc/Hexane)

$^1$HNMR($CDCl_3$)δ10.40(s,1), 7.67(s,1), 7.42(m,5), 6.45(s,1), 5.20(s,2), 4.00(t,2,J=6.15 Hz), 2.58(q,2,J=7.42 Hz), 1.86(m,2), 1.58(s(br), 6), 1.37(s,6), 1.18(t,3,J=7.50 Hz)

IR(KBr) 2980, 2940, 2860, 2230, 1660, 1600, 1575 $cm^{-1}$

Mass Spec(FD) m/e 393 (M+)

Elem Anal Calc'd for $C_{25}H_3NO_3$:

C,76.30; H, 7.94; N,3.56;

Found C,76.54; H, 7.84; N,3.60.

D. Preparation of 1-benzyloxy-3-(6-cyano-6-methyl-heptyloxy)-4-ethyl-6-hydroxy benzene A solution of the aldehyde in $CH_2Cl_2$ (0.18M) at room temperature was treated with m-chloroperbenzoic acid (1.1 eqv), and the reaction was stirred at room temp. After 30 min. a ppt formed. The reaction was complete after 5 h. The precipitate was removed by filtration. The solvent was removed under vacuum and the resulting solid was dissolved in THF (0.28M) and stirred overnight with 2N NaOH (2.5 eqv). Subsequently, the THF was removed under vacuum, and the resulting aqueous mixture was diluted with $H_2O$ and acidified to pH 1 with 1N HCl. The milky suspension was extracted several times with EtOAc. The organic extract was washed several times with saturated aqueous $NaHCO_3$ solution and then with brine. The organic layer was dried over $MgSO_4$. Filtration and solvent removal gave 8.70 g of a brown oil. The oil was purified by silica gel chromatography. 1-Benzyloxy-2-(6-cyano-6-methylheptyloxy)-4-ethyl-6-hydroxy benzene was obtained in 94% yield from 1-Benzyloxy-2-(6-cyano-6-methyl-heptyloxy)-4-ethyl-6-formyl benzene.

TLC Rf=0.38 (30% EtOAc/Hexane)

$^1$HNMR($CDCl_3$)δ7.42 (m,5) 6.79 (s,1), 6.56 (s,1), 5.30 (s,1) 5.10(s,2), 3.89(t,2,J=6.25 Hz), 2.58(q,2,J=7.51 Hz), 1.82(m,1), 1.52(s(br),6), 1.19(t,3,J=7.46 Hz)

IR (KBr) 3450, 2950, 2870, 2240, 1750, 1625, 1510 $cm^{-1}$

Mass Spec(FD) m/e 382(M++1)

Elem Anal Calc'd for $C_{24}H_{31}NO_3$:

C,75.56; H,8.19; N,3.67;

Found C,74.91; H,8.13, N,4.11.

E. Preparation of 1-Benzyloxy-3-(6-cyano-6-methyl-heptyloxy)-4-ethyl-6-methoxy benzene.

A 0.22M solution of the phenol in a 5:1 mixture of methyethyl-ketone: DMSO was stirred with $H_2CO_3$ (1.75 eq) under argon atmosphere. To this solution at room temperature was added methyliodide (4.0 eqv). The reaction was then stirred at room temp or 80° C. for 24 to 48 h. The reaction was quenched with water, and the mixture was extracted several times with EtOAc. The EtOAc extract was washed with water and brine and then dried over $MgSO_4$. Filtration and solvent removal gave the crude product which was purified by silica gel flash chromatography.

1-Benzyloxy-2-(6-cyano-6-methylheptyloxy)-4-ethyl-6-methoxy benzene was prepared in 75% yield as a white solid from 1-Benzyloxy-2-(6-cyano-6-methylheptyloxy)-4-ethyl-6-hydroxy benzene and methyliodide.

TLC Rf=0.53 (30% EtOAc/Hexane)

$^1$HNMR($CDCl_3$)δ7.39(m,5), 6.76(s,1), 6.52(s,1), 5.15(s,1), 3.87(s,3), 3.84(t,2,J=6.31 Hz), 2.59(q,2,J=7.51 Hz), 7.76(m,2), 1.55(s(br), 6), 1.37(s,6), 1.19(t,3,J=7.45 Hz).

IR(KBr) 2957, 2945, 2969, 2931, 2867, 2250, 1615, 1526, 1512, 1463 $cm^{-1}$

Mass Spec (FD) m/e 395 (M+)

Elem Anal Calc'd for $C_{25}H_{33}NO_3$:

C,75.92; H,8.41;

Found C, 75.55; H, 8.17.

F. Preparation of 1-(6-cyano-6-methylheptyloxy)-2-ethyl-4-methoxy-5-hydroxy benzene.

To a solution of the benzyl ether in ethyl acetate or methanol (0.14M solution) was added 10% Pd/C (15% w/w). Hydrogen gas was bubbled through this solution for 15 min. The reaction was then stirred at room temp under an atmosphere of hydrogen. After starting material was consumed, argon was bubbled through the reaction mixture for 15 min. The reaction mixture was filtered through a Celite ® pad in a sintered glass funnel, and the catalyst was washed with EtOAc. The resulting crude product was purified by flash chromatography using silica gel as the solid support and eluting with an ethyl acetate/hexane mixture.

1-(6-cyano-6-methylheptyloxy)-2-ethyl-4-methoxy-5-hydroxy benzene was prepared from 1-Benzyloxy-2-(6-cyano-6-methylheptyloxy)-4-ethyl-6-methoxy benzene in 100% yield.

TLC Rf=0.36 (30% EtOAc/Hexane)
$^1$HNMR(CDCl$_3$)δ6.70(s,1), 6.53(s,1), 5.64(s,1), 3.90(t,2,J=6.24 Hz), 3.85(s,3), 2.59(q,2,J=7.48 Hz), 1.83 (m,2), 1.36(s(br),6), 1.19(t,3,J=7.44 Hz),
IR(CHCl$_3$) 3540, 3020, 2980, 2940, 2860, 2240, 1600, 1510, 1440 cm$^{-1}$
Mass Spec (FAB) m/e 305 (M+)
Elem Anal Calc'd for C$_{18}$H$_{27}$NO$_3$:
C,70.79; H,8.91; N, 4.59;
Found C, 70.99; H,9.02; N, 4.59.

G. Preparation of 4-Ethyl-2-methoxy-5-[[6-methyl-6-(2H-tetrazol-5-yl)heptyl]oxy]phenol sodium salt.

To a solution of the nitrile in ethyleneglycol diethylether (0.20M solution) under argon atmosphere was added tri-nbutyltin azide (6.0 eqv). The reaction was then refluxed from 48 to 72 h. The reaction was then cooled to room temperature and treated with 5N HCl (11 eqv) and stirred for 2 h. The reaction mixture was then diluted with water and extracted with EtOAc. The ethyl acetate extract was dried over MgSO$_4$, filtered and solvent removed under vacuum to give an orange oil. The resulting oil was dissolved in Et$_2$O and treated with 1.1M aq KF solution (8.0 eqv), and stirred for 2.5 h. The resulting precipitate was removed by filtration. The solvent was removed from the filtrate and the remaining residue was triturated with hexane. The resulting solid was dissolved in methanol and treated with 2N NaOH (5 eqv), and stirred for 1.5 h. The solvent was then removed under vacuum, and the resulting solid was purified by reverse phase chromatography using CHP-20 resin and eluting with 60% MeOH/H$_2$O. The desired product was obtained as a white lyophilate sodium salt.

4-Ethyl-2-methoxy-5-[[6-methyl-6-(2H-tetrazol-5-yl)heptyl]oxy]phenol sodium salt was prepared in 59% yield from 1-(6-cyano-6-methylheptyloxy )-2-ethyl-4-methoxy-5 hydroxy benzene.

TLC Rf=0.39 (10% MeOH/CH$_2$Cl$_2$)
$^1$HNMR(D$_2$O)δ6.76(s,1), 6.49(S,1), 3.71(S,3), 3.71(t,2,J=8.12 Hz), 2.36(q,2,J=7.52 Hz), 1.55(m,6), 1.26(s,6), 1.20(m,2), 0.98(t,3,J=7.52 Hz)
IR(KBr) 2899, 2865, 2852, 1609, 1532, 1520, 1480 cm$^{-1}$
Mass Spec (FAB) m/e 393 (M+ +2Na+), 371 (M+ +Na+ +H)
Elem Anal Calc'd for C$_{18}$H$_{27}$N$_4$O$_3$Na . 1.9H$_2$O:
C, 53.44; H, 7.62;
Found C, 53.47; H, 7.27.

EXAMPLE 2

Preparation of 4-Ethyl-2-ethoxy-5-[[6-methyl-6-(2H-tetrazol-5-yl)heptyl]oxy] phenol sodium salt, a compound represented by the formula:

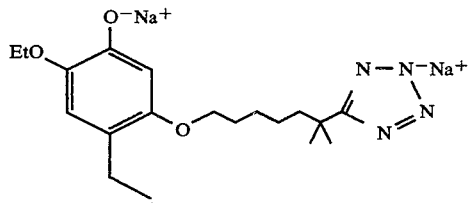

A. Preparation of 5-Ethyl-2,4-Dihydroxybenzaldehyde.

Dimethyformamide (250 mL) was cooled to 0° C. under argon atmosphere. With stirring, POCl$_3$ (18.60 mL, 0.20 mol) was added slowly to the DMF. After several minutes at 0° C., the reaction was warmed to room temp and CH$_2$Cl$_2$ (150 mL) was added to the reaction mixture to dissolve the solid. The reaction was subsequently recooled to 0° C. 4-Ethyresorcinol (25.0 g, 0.181 mol) was added to the reaction mixture as a 200 mL CH$_2$Cl$_2$ solution. After stirring at 0° C. for 10 min., the reaction was warmed to room temp and then refluxed for 16 h. The reaction was cooled to room temp, and a 100 mL water solution of NaOAc (50 g) was added slowly. This mixture was refluxed for 40 min then cooled to room temp. The aqueous layer was washed several times with CH$_2$Cl$_2$. The organics were combined and washed with 1N HCl solution and brine the dried over MgSO$_4$. Filtration and solvent removal gave an orange solid which was recrystallized from toluene and hexane (17 g, 56%)

TLC Rf=0.39 (30% EtOAc/Hexane)
$^1$HNMR(CDCl$_3$)δ11.30(s,1), 9.71(s,1), 7.29(s,1), 6.36(s(br),1), 2.61(q,2,J=7.48 Hz), 1.25(t,3,J=7.54 Hz)

B. Preparation of 1-[6-Methyl-6-cyanoheptyloxy]-2-ethyl-4-formyl-5-hydroxy benzene.

To a mixture of 5-ethyl-2,4-dihydroxybenzaldehyde (10.05 g, 0.060 mol), K$_2$CO$_3$ (14.63 g, 0.105 mol), KI (2.51 g, 0.015 mol) and DMF (250 mL), added a 250 mL solution of the chloronitrile (10.45 g, 0.060 mol) and warmed to 100° C. After 5 h, the reaction was cooled to room temp and the DMF was removed by vacuum distillation at 4 mmHg. The resulting brown oil was dissolved in EtOAc and washed with water and brine. The EtOAc extract was dried over MgSO$_4$ and filtered. Solvent removal gave 17.0 g of a brown oil. The oil was purified by flash chromatography on silica gel eluting with 15% EtOAc/hexane. The desired product was obtained as a clear oil (6.98 g, 38%).

TLC Rf=47 (30% EtOAc/Hexane)
$^1$HNMR(CDCl$_3$)δ11.44(s,1), 9.67(s,1), 7.22(s,1), 6.36(s,1), 4.02(t,2,J=6.22 Hz), 2.56(q,2,J=7.52 Hz), 1.85(m,2), 1.55(s(br),6), 1.34(s,6), 1.18(t,3,J=7.50 Hz)
IR(CHCl$_3$) 2980, 2944, 2860, 2230, 1640, 1585, 1493 cm$^{-1}$
Mass Spec(FD) m/e 303 (M+)
Elem Anal Calc'd for C$_{18}$H$_{25}$NO$_3$:
C,71.26; H, 8.31; N,4.62;
Found C,71.39; H, 8.10; N,4.75.

C. Preparation of 1-Benzyloxy-3-(6-cyano-6-methylheptyloxy)-4-ethyl-6-formyl benzene.

A solution of 40 mL of dry DMF, 1-[6-Methyl-6-cyanoheptyloxy]-2-ethyl-4-formyl-5-hydroxy benzene (3.05 g, 10.7 mmol) and K$_2$CO$_3$ (2,43 g, 17.6 mmol) were stirred at room temp. To this mixture was added benzylbromide (3.66 g, 21.4 mmol), and the reaction was warmed to 75° C. After 19 h the reaction was cooled to room temp. and the solids were removed by filtration. The DMF was removed from the filtrate by vacuum distillation at 6 mHg, and the resulting material was dissolved in EtOAc and washed with water and brine. The organic layer was dried over MgSO$_4$. Filtration and solvent removal gave a white solid (4.52 g). The solid was recrystallized from Et$_2$O/Hexane to give 3.42 g (82%) of white flakes.

TLC Rf=0.40 (30% EtOAc/Hexane)
$^1$HNMR(CDCl$_3$)δ10.40(s,1), 7.67(s,1), 7.42(m,5), 6.45(s,1), 5.20(s,2), 4.00(t,2,J=6.15 Hz), 2.58(q,2,J=7.42

Hz), 1.86(m,2), 1.58(s(br), 6), 1.37(s,6), 1.18(t,3,J=7.50 Hz)

IR(KBr) 2980, 2940, 2860, 2230, 1660, 1600, 1575 cm$^{-1}$

Mass Spec(FD) m/e 393(M+)
Elem Anal Calc'd for $C_{25}H_3NO_3$:
C,76.30; H, 7.94; N,3.56;
Found C,76.54; H, 7.84; N,3.60.

D. Preparation of 1-Benzyloxy-3-(6-cyano-6-methylheptyloxy)-4-ethyl-6-hydroxy benzene.

A solution of the aldehyde in $CH_2Cl_2$ (0.18M) at room temperature was treated with m-chloroperbenzoic acid (1.1 eqv), and the reaction was stirred at room temp. After 30 min. a ppt formed. The reaction was complete after 5 h. The precipitate was removed by filtration. The solvent was removed under vacuum and the resulting solid was dissolved in THF (0.28M) and stirred overnight with 2N NaOH (2.5 eqv). Subsequently, the THF was removed under vacuum, and the resulting aqueous mixture was diluted with $H_2O$ and acidified to pH 1 with 1N HCl. The milky suspension was extracted several times with EtOAc. The organic extract was washed several times with saturated aqueous $NaHCO_3$ solution and then with brine. The organic layer was dried over $MgSO_4$. Filtration and solvent removal gave 8.70 g of a brown oil. The oil was purified by silica gel chromatography.

1-Benzyloxy-3-(6-cyano-6-methylheptyloxy)-4-ethyl-6-hydroxy benzene was obtained in 94% yield from 1-Benzyloxy-3-(6-cyano-6-methyl-heptyloxy)-4-ethyl-6-formyl benzene.

TLC Rf=0.38 (30% EtOAc/Hexane)
$^1$HNMR(CDCl$_3$)δ7.42(m,5), 6.79(s,1), 6.56(s,1), 5.30(s,1), 5.10(s,2), 3.89(t,2,J=6.25 Hz), 2.58(q,2,J=7.51 Hz), 1.82(m,1), 1.52(s(br), 6), 1.19(t,3,J=7.46 Hz)
IR(KBr) 3450, 2950, 2870, 2240, 1750, 1625, 1510 cm$^{-1}$ Mass Spec(FD) m/e 382(M++1)
Elem Anal Calc'd for $C_{24}H_{31}NO_3$:
C,75.56; H,8.19; N,3.67;
Found C, 74.91; H, 8.13, N, 4.11.

E. Preparation of 1-Benzyloxy-3-(6-cyano-6-methylheptyloxy)-4-ethyl-6-ethoxy benzene.

A 0.22M. solution of the phenol in a 5:1 mixture of methyethyl-ketone: DMSO was stirred with $K_2CO_3$ (1.75 eq) under argon atmosphere. To this solution at room temperature was added the alkyliodide (4.0 eqv). The reaction was then stirred at room temp or 80° C. for 24 to 48 h. The reaction was quenched with water, and the mixture was extracted several times with EtOAc. The EtOAc extract was washed with water and brine and then dried over $MgSO_4$. Filtration and solvent removal gave the crude product which was purified by silica gel flash chromatography.

1-Benzyloxy-2-(6-cyano-6-methylheptyloxy)-4-ethyl-6-ethoxy benzene was prepared in 38% yield as a white solid from 1-Benzyloxy-2-(6-cyano-6-methylheptyloxy)-4-ethyl-6-hydroxy benzene and ethyliodide.

TLC Rf=0.46 (30% EtOAc/Hexane)
$^1$HNMR(CDCl$_3$)δ7.42(m,5), 6.80(s,1), 6.54(s,1), 5.15(s,2), 4.09(q,2,J=7.00 Hz), 3.86(t,2,J=6.20 Hz), 2.60(q, 2, J=7.52 Hz), 1.79(m,2)1.54(m,6), 1.44(t,3,J=6.98 Hz), 1.37(S,6), 1.21(t,3,J=7.45 Hz )
IR(KBr) 2957, 2945, 2930, 2868, 2225, 1613, 1525, 1462, cm$^{-1}$ Mass Spec(FD) m/e 409(M+)
Elem Anal Calc'd for $C_{26}H_{35}O_3N$
C,76.28; H,8.56; N, 3.42;
Found C,76.05; H,8.37; N, 3.60.

F. Preparation of 1-(6-cyano-6-methylheptyloxy)-2-ethyl-4-ethoxy-5-hydroxy benzene.

To a solution of the benzyl ether in ethyl acetate or methanol (0.14M solution) was added 10% Pd/C (15% w/w). Hydrogen gas was bubbled through this solution for 15 min.

The reaction was then stirred at room temp under an atmosphere of hydrogen. After starting material was consumed, argon was bubbled through the reaction mixture for 15 min. The reaction mixture was filtered through a celite pad in a sintered glass funnel, and the catalyst was washed with EtOAc. The resulting crude product was purified by flash chromatography using silica gel as the solid support and eluting with an ethyl acetate/hexane mixture.

1-(6-cyano-6-methylheptyloxy)-2-ethyl-4-ethoxy-5-hydroxy benzene was prepared from 1-Benzyloxy-2-(6-cyano-6-methylheptyloxy)-4-ethyl-6-ethoxy benzene in 85% yield.

TLC Rf=0.36 (30% EtOAc/Hexane)
$^1$HNMR(CDCl$_3$)δ6.70(s,1), 6.53(s,1), 5.63(s,1), 4.07(q,2,J=6.96 Hz), 3.90(t,2,J=6.23 Hz), 2.57(q,2,J=7.47 Hz), 1.85(m,2), 1.56(s(br),6), 1.42(t,3,J=6.97 Hz), 1.36(s,6), 1.17 (t,3, J=7.60 Hz )
IR(KBr) 3400(br), 2975, 2950, 2875, 2938, 2230, 1612, 1525, 1450 cm$^{-1}$ Mass Spec (FD) m/e 319 (M+)

G. Preparation of 4-Ethyl-2-ethoxy-5-[[6-methyl-6-(2H-tetrazol-5-yl)heptyl]oxy]phenol disodium salt.

To a solution of the nitrile in ethyleneglycol diethylether (0.20M solution) under argon atmosphere added tri-n-butyltin azide (6.0 eqv). The reaction was then refluxed from 48 to 72 h. The reaction was then cooled to room temperature and treated with 5N HCl (11 eqv) and stirred for 2 h. The reaction mixture was then diluted with water and extracted with EtOAc. The ethyl acetate extract was dried over $MgSO_4$, filtered and solvent removed under vacuum to give an orange oil. The resulting oil was dissolved in $Et_2O$ and treated with 1.1M aq KF solution (8.0 eqv), and stirred for 2.5 h. The resulting precipitate was removed by filtration. The solvent was removed from the filtrate and the remaining residue was triturated with hexane. The resulting solid was dissolved in methanol and treated with 2N NaOH (5 eqv), and stirred for 1.5 h. The solvent was then removed under vacuum, and the resulting solid was purified by reverse phase chromatography using CHP-20 resin and eluting with 60% MeOH/$H_2O$. The desired product was obtained as a white lyophilate sodium salt.

4-Ethyl-2-ethoxy-5-[[6-methyl-6-(2H-tetrazol-5-yl)heptyl]oxy]phenol as a white lyophilate disodium salt was prepared in 35% yield from 1-(6-cyano-6-methylheptyloxy)-2-ethyl-4-ethoxy-5-hydroxy benzene.

TLC Rf=0.40 (10% MeOH/$CH_2Cl_2$)
$^1$HNMR(d$^6$-DMSO)δ9.65(S(br),1), 6.62(s,1), 6.46(s,1), 3.89(q,2,J=6.96 Hz), 3.72(t,2,J=6.40 Hz), 2.37(q,2,J=7.50 Hz), 1.56(m,4), 1.26(m,5), 1.22(s,6), 1.09(m,2), 1.03 (t,3,J=7.50 Hz)
IR(KBr) 3464, 3457, 2982, 2972, 2962, 2860, 1609, 1531, 1517, 1482 cm$^{-1}$

Mass Spec (FAB) m/e 385 (M++2Na++H), 384 (M++2Na+)
Elem Anal Calc'd for $C_{19}H_{29}N_4O_3Na$-0.25$H_2O$
C, 55.54; H, 6.94; N, 13.64;
Found C, 55.39; H, 7.48; N, 13.53.

EXAMPLE 3

Preparation of 4-Ethyl-2-pentyloxy-5-[[6-methyl-6-(2H-tetrazol-5-yl)heptyl]oxy] phenol sodium salt, a compound represented by the formula:

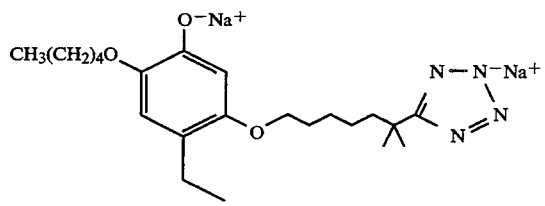

A. Preparation of 5-Ethyl-2,4-Dihydroxybenzaldehyde.

Dimethyformamide (250 mL) was cooled to 0° C. under argon atmosphere. With stirring, $POCl_3$ (18.60 mL, 0.20 mol) was added slowly to the DMF. After several minutes at 0° C., the reaction was warmed to room temp and $CH_2Cl_2$ (150 mL) was added to the reaction mixture to dissolve the solid. The reaction was subsequently recooled to 0° C. 4-Ethyresorcinol (25.0 g, 0.181 mol) was added to the reaction mixture as a 200 mL $CH_2Cl_2$ solution. After stirring at 0° C. for 10 min., the reaction was warmed to room temp and then refluxed for 16 h. The reaction was cooled to room temp, and a 100 mL water solution of NaOAc (50 g) was added slowly. This mixture was refluxed for 40 min then cooled to room temp. The aqueous layer was washed several times with $CH_2Cl_2$. The organics were combined and washed with 1N HCl solution and brine the dried over $MgSO_4$. Filtration and solvent removal gave an orange solid which was recrystallized from toluene and hexane (17 g, 56%)

TLC Rf=0.39 (30% EtOAc/Hexane)
$^1$HNMR($CDCl_3$)δ11.30(s,1), 9.71(s,1), 7.29(s,1), 6.36(s(br), 1), 2.61(q,2,J=7.48 Hz), 1.25(t,3,J=7.54 Hz)

B. Preparation of 1-[6-Methyl-6-cyanoheptyloxy]-2-ethyl-4-formyl-5-hydroxy benzene.

To a solution of 2-cyano-2-methyl-7-chloroheptane (15.01 g, 86.8 mmol) in 600 mL of acetone, added tetraethylammonium acetate tetrahydrate (45.36 g, 1.74 mol). The reaction was then refluxed under argon atmosphere for 25 h. The reaction was cooled to room temp and the acetone was removed under vacuum. To the resulting residue was added water and $Et_2O$. The aqueous layer was extracted with $Et_2O$ several times and then dried over $MgSO_4$. Filtration and solvent removal gave a clear oil (23.19 g).

To the above prepared acetate in 400 mL of methanol was added $K_2CO_3$ (16.27 g) and stirred at room temp for 24 h. The reaction mixture was filtered to remove the solids and the solvent was removed from the filtrate. The resulting solid was dissolved in EtOAc and the EtOAc solution was washed with $H_2O$. The organic solution was dried over $MgSO_4$. Filtration and solvent removal gave 14.50 g of a yellow oil which was purified by Waters Prep 500 chromatography using a silica gel support and eluting with a solvent gradient of 5% to 60% EtOAc/Hexane over 50 min. The desired alcohol was obtained as a clear oil (10.58 g, 57%).

TLC Rf=0.13 (30% EtOAc/Hexane)

A 50 mL dry THF solution of the above prepare 2-cyano-2-methyl-7-hydroxyheptane and 2,4-dihydroxy-5-ethylbenzaldehyde was stirred at room temp. To this solution added triphenylphosphine (17.91 g, 68.3 mmol) and finally diethyl azodicarboxylate (11.89 g, 68.3 mmol). The reaction was stirred at room temp for 2 h 15 min. and then quenched with saturated $NH_4Cl$ solution. The THF was removed under vacuum and the resulting residue was dissolved in EtOAc and the EtOAc solution was washed with brine. The organic layer was dried over $MgSO_4$. Filtration and solvent removal gave an orange solid. The product was purified by Waters Prep 500 chromatography using silica gel as a solid support and eluting with a gradient of 10% to 30% EtOAc/Hexane over 50 min. The desired product was obtained as a yellow oil (10.50 g, 51%).

$^1$HNMR($CDCl_3$)δ11.44(s,1), 9.67(s,1), 7.22(s,1), 6.36(s,1), 4.02(t,2,J=6.22 Hz), 2.56(q,2,J=7.52 Hz), 1.85(m,2), 1.55(s(br), 6), 1.34(s,6), 1.18(t,3,J=7.50 Hz)

IR ($CHCl_3$) 2980, 2944, 2860, 2230, 1640, 1585, 1493 $cm^{-1}$

Mass Spec(FD) m/e 303 (M+)
Elem Anal Calc'd for $C_{18}H_{25}NO_3$:
C,71.26; H, 8.31; N,4.62;
Found C,71.39; H, 8.10; N,4.75.

C. Preparation of 1-Benzyloxy-3-(6-cyano-6-methylheptyloxy)-4-ethyl-6-formyl benzene.

A solution of 40 mL of dry DMF, 1-[6-Methyl-6-cyanoheptyloxy]-2-ethyl-4-formyl-5-hydroxy benzene (3.05 g, 10.7 mmol) and $K_2CO_3$ (2,43 g, 17.6 mmol) were stirred at room temp. To this mixture was added benzylbromide (3.66 g, 21.4 mmol), and the reaction was warmed to 75° C. After 19 h the reaction was cooled to room temp. and the solids were removed by filtration. The DMF was removed from the filtrate by vacuum distillation at 6 mHg, and the resulting material was dissolved in EtOAc and washed with water and brine. The organic layer was dried over $MgSO_4$. Filtration and solvent removal gave a white solid (4.52 g). The solid was recrystallized from $Et_2O$/Hexane to give 3.42 g (82%) of white flakes.

TLC Rf=0.40 (30% EtOAc/Hexane)
$^1$HNMR($CDCl_3$)δ10.40(s,1), 7.67(s,1), 7.42(m,5), 6.45(s,1), 5.20(s,2), 4.00(t,2,J=6.15 Hz), 2.58(q,2,J=7.42 Hz), 1.86(m,2), 1.58(s(br), 6), 1.37(s,6), 1.18(t,3,J=7.50 Hz)

IR(KBr) 2980, 2940, 2860, 2230, 1660, 1600, 1575 $cm^{-1}$

Mass Spec(FD) m/e 393(M+)
Elem Anal Calc'd for $C_{25}H_3NO_3$:
C,76.30; H, 7.94; N,3.56;
Found C,76.54; H, 7.84; N,3.60.

D. Preparation of 1-Benzyloxy-3-(6-cyano-6-methylheptyloxy)-4-ethyl-6-hydroxy benzene.

A solution of the aldehyde in $CH_2Cl_2$ (0.18M) at room temperature was treated with m-chloroperbenzoic acid (1.1 eqv), and the reaction was stirred at room temp. After 30 min. a ppt formed. The reaction was complete after 5 h. The precipitate was removed by filtration. The solvent was removed under vacuum and the resulting solid was dissolved in THF (0.28M) and stirred overnight with 2N NaOH (2.5 eqv). Subsequently, the THF was removed under vacuum, and the resulting aqueous mixture was diluted with $H_2O$ and acidified to pH 1 with 1N HCl. The milky suspension was extracted several times with EtOAc. The organic extract was washed several times with saturated aqueous $NaHCO_3$ solution and then with brine. The organic layer was dried over $MgSO_4$. Filtration and solvent removal gave 8.70 g of a brown oil. The oil was purified by silica gel chromatography.

1-Benzyloxy-3-(6-cyano-6-methylheptyloxy)-4-ethyl-6-hydroxy benzene was obtained in 94% yield from 1-Benzyloxy-3-(6-cyano-6-methyl-heptyloxy)-4-ethyl-6-formyl benzene.

TLC Rf=0.38 (30% EtOAc/Hexane)

$^1$HNMR(CDCl$_3$)$\delta$7.42(m,5), 6.79(s,1), 6.56(s,1), 5.30(s,1), 5.10(s,2), 3.89(t,2,J=6.25 Hz), 2.58(q,2,J=7.51 Hz), 1.82(m,1), 1.52(s(br), 6), 1.19(t,3,J=7.46 Hz)

IR(KBr)3450, 2950, 2870, 2240, 1750, 1625, 1510 cm$^{-1}$

Mass Spec(FD) m/e 382(M$^+$+1)

Elem Anal Calc'd for C$_{24}$H$_{31}$NO$_3$:

C,75.56; H,8.19; N,3.67;

Found C,74.91; H,8.13, N,4.11.

E. Preparation of 1-Benzyloxy-3-(6-cyano-6-methyl-heptyloxy)-4-ethyl-6-pentyloxy benzene.

A suspension of hexane washed NaH (2.10 eqv) in dry DMF (1.3 M soln) was stirred under argon arm. at room temp. A solution of the phenol in dry DMF (0.15M) was added slowly to the NaH suspension. The reaction was stirred at room temp for 30 min. 18-Crown-6 was added to the reaction followed by the dropwise addition of alkyl halide (5.0 eqv). After stirring at room temp for several hours the reaction was quenched with saturated aqueous NH$_4$Cl solution, diluted with water and extracted with EtOAc. The EtOAc extract was washed with water and then dried over MgSO$_4$. Filtration and solvent gave the crude product which was purified by silica gel flash chromatography.

1-Benzyloxy-3-(6-cyano-6-methylheptyloxy)-4-ethyl-6-pentyloxy benzene was prepared in 100% yield as a white solid from 1-Benzyloxy-3-(6-cyano-6-methylheptyloxy)-4-ethyl-6-hydroxy benzene and 1-bromopentane.

TLC Rf=0.56 (30% EtOAc/Hexane)

$^1$HNMR(CDCl$_3$)$\delta$7.43(m,5), 6.78(s,1), 6.53(s,1), 5.12(s,2), 4.00(t,2,J=6.62 Hz), 3.86(t,2,J=6.02 Hz), 2.58(q,2, J=7.53 Hz), 1.80(m,4)1.47(m,12), 1.37(s,6), 1.19(t,3,J=7.50 Hz), 0.94 (t, 3, J=7.03 Hz)

IR(CHCl$_3$)3012, 2958, 2957, 2942, 2938, 2200, 1700, 1506, 1471, 1454, 1412 cm$^{-1}$

Mass Spec(FAB) m/e 452(M$^+$)

Elem Anal Calc'd for C$_{29}$H$_{41}$NO$_3$:

C,77.12; H,9.15; N, 3.10;

Found C,77.29; H,9.39; N, 2.91.

F. Preparation of 1-(6-cyano-6-methylheptyloxy)-2-ethyl-4-pentyloxy-5-hydroxy benzene.

To a solution of the benzyl ether in ethyl acetate or methanol (0.14M solution) was added 10% Pd/C (15% w/w). Hydrogen gas was bubbled through this solution for 15 min. The reaction was then stirred at room temp under an atmosphere of hydrogen. After starting material was consumed, argon was bubbled through the reaction mixture for 15 min. The reaction mixture was filtered through a celite pad in a sintered glass funnel, and the catalyst was washed with EtOAc. The resulting crude product was purified by flash chromatography using silica gel as the solid support and eluting with an ethyl acetate/hexane mixture.

1-(6-cyano-6-methylheptyloxy)-2-ethyl-4-pentyloxy-5-hydroxy benzene was prepared from 1-Benzyloxy-3-(6-cyano-6-methylheptyloxy)-4-ethyl-6-pentyloxy benzene in 97% yield.

TLC Rf=0.46 (30% EtOAc/Hexane)

$^1$HNMR(CDCl$_3$)$\delta$6.70(s,1), 6.53(s,1), 5.58(s,1), 3.99(t,2,J=6.58 Hz), 3.91(t,2,J=6.60 Hz), 2.57(q,2,J=7.51 Hz), 1.80(m,4), 1.57(s(br), 6), 1.42(m,4), 1.36(s,6), 1.18(t,3,J=7.50 Hz), 0.95(t,3,J=6.93 Hz).

IR(CHCl$_3$)3541, 3011, 2940, 2874, 2237, 1604, 1508, 1471 cm$^{-1}$

Mass Spec (FD) m/e 361 (M$^+$)

Elem Anal Calc'd for C$_{22}$H$_{35}$NO$_3$:

C, 73.13; H, 9.69;

Found C,73.33; H,9.53.

G. Preparation of 4-Ethyl-2-pentyloxy-5-[[6-methyl-6-(2H-tetrazol-5-yl)heptyl]oxy]phenol disodium salt.

To a solution of the nitrile in ethyleneglycol diethylether (0.20M solution) under argon atmosphere added tri-n-butyltin azide (6.0 eqv). The reaction was then refluxed from 48 to 72 h. The reaction was then cooled to room temperature and treated with 5N HCl (11 eqv) and stirred for 2 h. The reaction mixture was then diluted with water and extracted with EtOAc. The ethyl acetate extract was dried over MgSO$_4$, filtered and solvent removed under vacuum to give an orange oil. The resulting oil was dissolved in Et$_2$O and treated with 1.1M aq KF solution (8.0 eqv), and stirred for 2.5 h. The resulting precipitate was removed by filtration. The solvent was removed from the filtrate and the remaining residue was triturated with hexane. The resulting solid was dissolved in methanol and treated with 2N NaOH (5 eqv), and stirred for 1.5 h. The solvent was then removed under vacuum, and the resulting solid was purified by reverse phase chromatography using CHP-20 resin and eluting with 60% MeOH/H$_2$O. The desired product was obtained as a white lyophilate sodium salt.

4-Ethyl-2-pentyloxy-5-[[6-methyl-6-(2H-tetrazol-5-yl)heptyl]oxy]phenol disodium salt was prepared in 27% yield from 1-(6-cyano-6-methylheptyloxy)-2-ethyl-4-pentyloxy-5-hydroxy benzene.

TLC Rf=0.55 (10% MeOH/CH2Cl2)

$^1$HNMR(d$^6$-DMSO)$\delta$9.85(S(br),1), 6.61(s,1), 6.45(s,1), 3.82(t,2,J=6.58 Hz), 3.72(t,2,J=6.50 Hz), 2.38(q,2,J=7.47 Hz), 1.59(m,4), 1.30(m,8), 1.10(m,4), 1.02(t,3,J=7.45 Hz), 0.87 (t,3,J=6.97 Hz)

IR(KBr) 3420, 2936, 1612, 1519, 1448 cm$^{-1}$

Mass Spec (FAB) m/e 449 (M$^+$+2Na$^+$+H), 427 (M$^{30}$ +Na$^{30}$ H)

Elem Anal Calc'd for C$_{22}$H$_{34}$N$_4$O$_3$Na$_2$-2.OH$_2$O:

C, 54.54; H, 7.85; N, 11.57;

Found C,54.50; H,7.00; N, 11.26.

EXAMPLE 4

Preparation of 4-Ethyl-2-(1-methylethoxy)-5-[[6-methyl-6-(2H-tetrazol-5-yl)heptyl]oxy] phenol sodium salt, a compound represented by the formula:

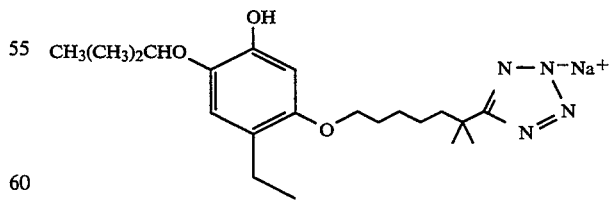

A. Preparation of 5-Ethyl-2,4-Dihydroxybenzaldehyde.

Dimethyformamide (250 mL) was cooled to 0° C. under argon atmosphere. With stirring, POCl$_3$ (18.60 mL, 0.20 mol) was added slowly to the DMF. After several minutes at 0° C., the reaction was warmed to room temp and CH$_2$Cl$_2$ (150 mL) was added to the reaction mixture to dissolve the solid. The reaction was subsequently recooled to 0° C. 4-Ethyresorcinol (25.0 g, 0.181 mol) was added to the reaction mixture as a 200 mL $CH_2Cl_2$ solution. After stirring at 0° C. for 10 min., the reaction was warmed to room temp and then refluxed for 16 h. The reaction was cooled to room temp, and a 100 mL water solution of NaOAc (50 g) was added slowly. This mixture was refluxed for 40 min then cooled to room temp. The aqueous layer was washed several times with $CH_2Cl_2$. The organics were combined and washed with 1N HCl solution and brine the dried over $MgSO_4$. Filtration and solvent removal gave an orange solid which was recrystallized from toluene and hexane (17 g, 56%)

TLC Rf=0.39 (30% EtOAc/Hexane)

$^1HNMR(CDCl_3)\delta 11.30(s,1)9.71(s,1)7.29(s,1)$ 6.36(s(br), 1), 2.61(q,2,J=7.48 Hz), 1.25(t,3,J=7.54 Hz)

B. Preparation of 1-[6-Methyl-6-cyanoheptyloxy]-2-ethyl-4-formyl-5-hydroxy benzene.

To a solution of 2-cyano-2-methyl-7-chloroheptane (15.01 g, 86.8 mmol) in 600 mL of acetone, added tetraethylammonium acetate tetrahydrate (45.36 g, 1.74 mol). The reaction was then refluxed under argon atmosphere for 25 h. The reaction was cooled to room temp and the acetone was removed under vacuum. To the resulting residue was added water and $Et_2O$. The aqueous layer was extracted with $Et_2O$ several times and then dried over $MgSO_4$. Filtration and solvent removal gave a clear oil (23.19 g).

To the above prepared acetate in 400 mL of methanol was added $K_2CO_3$ (16.27 g) and stirred at room temp for 24 h. The reaction mixture was filtered to remove the solids and the solvent was removed from the filtrate. The resulting solid was dissolved in EtOAc and the EtOAc solution was washed with $H_2O$. The organic solution was dried over $MgSO_4$. Filtration and solvent removal gave 14.50 g of a yellow oil which was purified by Waters Prep 500 chromatography using a silica gel support and eluting with a solvent gradient of 5% to 60% EtOAc/Hexane over 50 min. The desired alcohol was obtained as a clear oil (10.58 g, 57%).

TLC Rf=0.13 (30% EtOAc/Hexane)

A 50 mL dry THF solution of the above prepare 2-cyano-2-methyl-7-hydroxyheptane and 2,3-dihydroxy-4-ethylbenzaldehyde was stirred at room temp. To this solution added triphenylphosphine (17.91 g, 68.3 mmol) and finally diethyl azodicarboxylate (11.89 g, 68.3 mmol). The reaction was stirred at room temp for 2 h 15 min. and then quenched with saturated $NH_4Cl$ solution. The THF was removed under vacuum and the resulting residue was dissolved in EtOAc and the EtOAc solution was washed with brine. The organic layer was dried over $MgSO_4$. Filtration and solvent removal gave an orange solid. The product was purified by Waters Prep 500 chromatography using silica gel as a solid support and eluting with a gradient of 10% to 30% EtOAc/Hexane over 50 min. The desired product was obtained as a yellow oil (10.50 g, 51%).

$^1HNMR(CDCl_3)\delta 11.44(s,1)$, 9.67(s,1), 7.22(s,1), 6.36(s,1), 4.02(t,2,J=6.22 Hz), 2.56(q,2,J=7.52 Hz), 1.85(m,2), 1.55(s(br), 6), 1.34(s,6), 1.18(t,3,J=7.50 Hz)

IR($CHCl_3$) 2980, 2944, 2860, 2230, 1640, 1585, 1493 $cm^{-1}$

Mass Spec(FD) m/e 303(M+)

Elem Anal Calc'd for $C_{18}H_{25}NO_3$:

C,71.26; H, 8.31; N,4.62;

Found C,71.39; H, 8.10; N,4.75.

C. Preparation of 1-Benzyloxy-3-(6-cyano-6-methylheptyloxy)-4-ethyl-6-formyl benzene.

A solution of 40 mL of dry DMF, 1-[6-Methyl-6-cyanoheptyloxy]-2-ethyl-4-formyl-5-hydroxy benzene (3.05 g, 10.7 mmol) and $K_2CO_3$ (2,43 g, 17.6 mmol) were stirred at room temp. To this mixture was added benzylbromide (3.66 g, 21.4 mmol), and the reaction was warmed to 75° C. After 19 h the reaction was cooled to room temp. and the solids were removed by filtration. The DMF was removed from the filtrate by vacuum distillation at 6 mHg, and the resulting material was dissolved in EtOAc and washed with water and brine. The organic layer was dried over $MgSO_4$. Filtration and solvent removal gave a white solid (4.52 g). The solid was recrystallized from $Et_2O$/Hexane to give 3.42 g (82%) of white flakes.

TLC Rf=0.40 (30% EtOAc/Hexane)

$^1HNMR(CDCl_3)\delta 10.40(s,1)$, 7.67(s,1), 7.42(m,5), 6.45(s,1), 5.20(s,2), 4.00(t,2,J=6.15 Hz), 2.58(q,2,J=7.42 Hz), 1.86(m,2), 1.58(s(br), 6), 1.37(s,6), 1.18(t,3,J=7.50 Hz)

IR (KBr) 2980, 2940, 2860, 2230, 1660, 1600, 1575 $cm^{-1}$

Mass Spec(FD) m/e 393 (M+)

Elem Anal Calc'd for $C_{25}H_3NO_3$:

C,76.30; H, 7.94; N,3.56;

Found C,76.54; H, 7.84; N,3.60.

D. Preparation of 1-Benzyloxy-3-(6-cyano-6-methylheptyloxy)-4-ethyl-6-hydroxy benzene.

A solution of the aldehyde in $CH_2Cl_2$ (0.18M) at room temperature was treated with m-chloroperbenzoic acid (1.1 eqv), and the reaction was stirred at room temp. After 30 min. a ppt formed. The reaction was complete after 5 h. The precipitate was removed by filtration. The solvent was removed under vacuum and the resulting solid was dissolved in THF (0.28M) and stirred overnight with 2N NaOH (2.5 eqv). Subsequently, the THF was removed under vacuum, and the resulting aqueous mixture was diluted with $H_2O$ and acidified to pH 1 with 1N HCl. The milky suspension was extracted several times with EtOAc. The organic extract was washed several times with saturated aqueous $NaHCO_3$ solution and then with brine. The organic layer was dried over $MgSO_4$. Filtration and solvent removal gave 8.70 g of a brown oil. The oil was purified by silica gel chromatography.

1-Benzyloxy-3-(6-cyano-6-methylheptyloxy)-4-ethyl-6-hydroxy benzene was obtained in 94% yield from 1-Benzyloxy-3-(6-cyano-6-methyl-heptyloxy)-4-ethyl-6-formyl benzene.

TLC Rf=0.38 (30% EtOAc/Hexane)

$^1HNMR(CDCl_3)\delta 7.42(m$ 5), 6.79(s,1), 6.56(s,1)5.30(s,1) 5.10(s,2), 3.89(t,2,J=6.25 Hz), 2.58(q,2,J=7.51 Hz), 1.82(m,1), 1.52(s(br), 6), 1.19(t,3,J=7.46 Hz)

IR(KBr) 3450, 2950, 2870, 2240, 1750, 1625, 1510 $cm^{-1}$

Mass Spec (FD) m/e 382 (M++1)

Elem Anal Calc'd for $C_{24}H_{31}NO_3$

C,75.56; H,8.19; N,3.67;

Found C,74.91; H,8.13, N,4.11.

E. Preparation of 1-Benzyloxy-3-(6-cyano-6-methylheptyloxy)-4-ethyl-6-isopropoxy benzene.

A suspension of hexane washed NaH (2.10 eqv) in dry DMF (1.3M soln) was stirred under argon arm. at room temp. A solution of the phenol in dry DMF (0.15M) was added slowly to the NaH suspension. The reaction was stirred at room temp for 30 min. 18-

Crown-6 was added to the reaction followed by the dropwise addition of alkyl halide (5.0 eqv). After stirring at room temp for several hours the reaction was quenched with saturated aqueous NH$_4$Cl solution, diluted with water and extracted with EtOAc. The EtOAc extract was washed with water and then dried over MgSO$_4$. Filtration and solvent gave the crude product which was purified by silica gel flash chromatography.

1-Benzyloxy-3-(6-cyano-6-methylheptyloxy)-4-ethyl-6-isopropoxy benzene was prepared in 100% yield as a white solid from 1-Benzyloxy-3-(6-cyano-6-methylheptyloxy)-4-ethyl-6-hydroxy benzene and 2-iodo-propane.

TLC Rf=0.53 (30% EtOAc/Hexane)

$^1$HNMR(CDCl$_3$)δ7.38(m,5), 6.80(s,1), 6.52(s,1), 5.12(s,2), 4.40(m,1), 3.87(t,2,J=6.21 Hz), 2.57(q,2,J=7.51 Hz), 1.80(m,2), 1.56(s(br), 6), 1.37(s,6), 1.33(d, 6, J=6.05 Hz), 1.81 (t,3,J=7.50 Hz)

IR(CHCl$_3$) 3022, 2978, 2941, 2236, 1600, 1505, 1471, 1411, 1383, 1316 cm$^{-1}$

Mass Spec(FAB) m/e 423(M+)

Elem Anal Calc'd for C$_{27}$H$_{37}$NO$_3$
C,76.59; H,8.74; N, 3.31;
Found C, 76.67; H, 7.74; N, 3.58.

F. Preparation of 1-(6-cyano-6-methylheptyloxy)-2-ethyl-4-isopropoxy-5-hydroxy benzene.

To a solution of the benzyl ether in ethyl acetate or methanol (0.14M solution) was added 10% Pd/C (15% w/w). Hydrogen gas was bubbled through this solution for 15 min. The reaction was then stirred at room temp under an atmosphere of hydrogen. After starting material was consumed, argon was bubbled through the reaction mixture for 15 min. The reaction mixture was filtered through a celite pad in a sintered glass funnel, and the catalyst was washed with EtOAc. The resulting crude product was purified by flash chromatography using silica gel as the solid support and eluting with an ethyl acetate/hexane mixture.

1-(6-cyano-6-methylheptyloxy)-2-ethyl-4-isopropoxy-5-hydroxy benzene was prepared from 1-Benzyloxy-3-(6-cyano-6-methylheptyloxy)-4-ethyl-6-isopropoxy benzene in 97% yield.

TLC Rf=0.41 (30% EtOAc/Hexane)

$^1$HNMR(CDCl$_3$)δ6.72(s,1), 6.52(s,1), 5.58(s,1), 4.43(m,1), 3.90(t,2,J=6.22 Hz), 2.56(q,2,J=7.50 Hz), 1.82(m,2), 1.56(m,6), 1.36(s,6), 1.34(d,6,J=6.06 Hz), 1.16(t,3,J=7.50 Hz)

IR(CHCl$_3$) 3535, 3024, 2979, 2941, 2873, 2236, 1603, 1507, 1471 cm$^{-1}$

Mass Spec(FD) m/e 333(M+)

Elem Anal Calc'd for C$_{20}$H$_{31}$NO$_3$
C,72.04; H,9.37; N, 4.20;
Found C,72.32; H,9.63; N, 4.30.

G. Preparation of 4-Ethyl-2-(1-methylethoxy)-5-[[6-methyl-6-(2H-tetrazol-5-yl)heptyl]oxy]phenol sodium salt To a solution of the nitrile in ethyleneglycol diethylether (0.20M solution) under argon atmosphere added tri-n-butyltin azide (6.0 eqv). The reaction was then refluxed from 48 to 72 h. The reaction was then cooled to room temperature and treated with 5N HCl (11 eqv) and stirred for 2 h. The reaction mixture was then diluted with water and extracted with EtOAc. The ethyl acetate extract was dried over MgSO$_4$, filtered and solvent removed under vacuum to give an orange oil. The resulting oil was dissolved in Et$_2$O and treated with 1.1M aq KF solution (8.0 eqv), and stirred for 2.5 h.

The resulting precipitate was removed by filtration. The solvent was removed from the filtrate and the remaining residue was triturated with hexane. The resulting solid was dissolved in methanol and treated with 2N NaOH (5 eqv), and stirred for 1.5 h. The solvent was then removed under vacuum, and the resulting solid was purified by reverse phase chromatography using CHP-20 resin and eluting with 60% MeOH/H$_2$O. The desired product was obtained as a white lyophilate sodium salt.

4-Ethyl-2-(1-methylethyoxy)-5-[[6-methyl-6-(2H-tetrazol-5-yl)heptyl]oxy]phenol sodium salt was prepared in 43% yield from 1-(6-cyano-6-methylheptyloxy)-2-ethyl-4-isopropoxy-5-hydroxy benzene.

TLC Rf=0.48 (10% MeOH/CH$_2$Cl$_2$)

$^1$HNMR(d$^6$-DMSO)δ9.67(S(br),1), 6.63(s,1), 6.46(s,1), 4.29(m,2), 3.72(t,2,J=6.47 Hz), 2.37(q,2,J=7.54 Hz), 1.58(m,4), 1.32(m,4), 1.22(s,6), 1.16(d,6,J=6.10 Hz), 1.02(t,3,J=7.48 Hz).

IR(CHCl$_3$) 2973, 2937, 2872, 1620, 1508, 1437 cm$^{-1}$

Mass Spec(FAB) m/e 377(M+ +H)

Elem Anal Calc'd for C$_{20}$H$_{31}$N$_4$O$_3$Na·1.7H$_2$O.
C,55.93; H,8.08; N, 13.05;
Found C,56.26; H,8.24; N, 12.67.

EXAMPLE 5

Preparation of 4-Ethyl-2-(3-methylbutoxy)-5-[[6-methyl-6-(2H-tetrazol-5-yl) heptyl]oxy]phenol sodium salt, a compound represented by the formula:

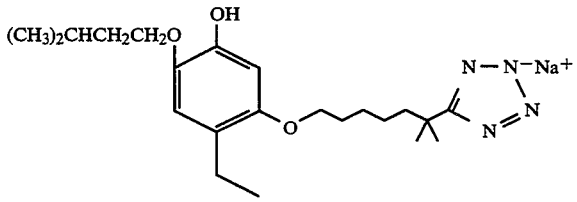

A. Preparation of 5-Ethyl-2,4-Dihydroxybenzaldehyde.

Dimethyformamide (250 mL) was cooled to 0° C. under argon atmosphere. With stirring, POCl$_3$ (18.60 mL, 0.20 mol) was added slowly to the DMF. After several minutes at 0° C., the reaction was warmed to room temp and CH$_2$Cl$_2$ (150 mL) was added to the reaction mixture to dissolve the solid. The reaction was subsequently recooled to 0° C. 4-Ethyresorcinol (25.0 g, 0.181 mol) was added to the reaction mixture as a 200 mL CH$_2$Cl$_2$ solution. After stirring at 0° C. for 10 min., the reaction was warmed to room temp and then refluxed for 16 h. The reaction was cooled to room temp, and a 100 mL water solution of NaOAc (50 g) was added slowly. This mixture was refluxed for 40 min then cooled to room temp. The aqueous layer was washed several times with CH$_2$Cl$_2$. The organics were combined and washed with 1N HCl solution and brine the dried over MgSO$_4$. Filtration and solvent removal gave an orange solid which was recrystallized from toluene and hexane (17 g, 56%)

TLC Rf=0.39 (30% EtOAc/Hexane)

$^1$HNMR(CDCl$_3$)δ11.30(s,1), 9.71(s,1), 7.29(s,1), 6.36(s(br), 1), 2.61(q,2,J=7.48 Hz), 1.25(t,3,J=7.54 Hz)

B. Preparation of 1-[6-Methyl-6-cyanoheptyloxy]-2-ethyl-4-formyl-5-hydroxy benzene.

To a solution of 2-cyano-2-methyl-7-chloroheptane (15.01 g, 86.8 mmol) in 600 mL of acetone, added tetraethylammonium acetate tetrahydrate (45.36 g, 1.74 mol). The reaction was then refluxed under argon atmosphere for 25 h. The reaction was cooled to room temp and the acetone was removed under vacuum. To the resulting residue was added water and Et$_2$O. The aqueous layer was extracted with Et$_2$O several times and then dried over MgSO$_4$. Filtration and solvent removal gave a clear oil (23.19 g).

To the above prepared acetate in 400 mL of methanol was added K$_2$CO$_3$ (16.27 g) and stirred at room temp for 24 h. The reaction mixture was filtered to remove the solids and the solvent was removed from the filtrate. The resulting solid was dissolved in EtOAc and the EtOAc solution was washed with H$_2$O. The organic solution was dried over MgSO$_4$. Filtration and solvent removal gave 14.50 g of a yellow oil which was purified by Waters Prep 500 chromatography using a silica gel support and eluting with a solvent gradient of 5% to 60% EtOAc/Hexane over 50 min. The desired alcohol was obtained as a clear oil (10.58 g, 57%).

TLC Rf=0.13 (30% EtOAc/Hexane)

A 50 mL dry THF solution of the above prepare 2-cyano-2-methyl-7-hydroxyheptane and 2,4-dihydroxy-5-ethylbenzaldehyde was stirred at room temp. To this solution was added triphenylphosphine (17.91 g, 68.3 mmol) and finally diethyl azodicarboxylate (11.89 g, 68.3 mmol). The reaction was stirred at room temp for 2 h 15 min. and then quenched with saturated NH$_4$Cl solution. The THF was removed under vacuum and the resulting residue was dissolved in EtOAc and the EtOAc solution was washed with brine. The organic layer was dried over MgSO$_4$. Filtration and solvent removal gave an orange solid. The product was purified by Waters Prep 500 chromatography using silica gel as a solid support and eluting with a gradient of 10% to 30% EtOAc/Hexane over 50 min. The desired product was obtained as a yellow oil (10.50 g, 51%).

$^1$HNMR(CDCl$_3$)δ11.44 (s,1)9.67 (s.1)7.22 (s,1)6.36 (s,1) 4.02(t,2,J=6.22 Hz), 2.56(q,2,J=7.52 Hz), 1.85(m,2), 1.55(s(br), 6), 1.34(s,6), 1.18(t,3,J=7.50 Hz)

IR (CHCl$_3$) 2980, 2944, 2860, 2230, 1640, 1585, 1493 cm$^{-1}$

Mass Spec(FD) m/e 303 (M+)

Elem Anal Calc'd for C$_{18}$H$_{25}$NO$_3$:

C,71.26; H, 8.31; N,4.62;

Found C,71.39; H, 8.10; N,4.75.

C. Preparation of 1-Benzyloxy-3-(6-cyano-6-methylheptyloxy)-4-ethyl-6-formyl benzene.

A solution of 40 mL of dry DMF, 1-[6-Methyl-6cyanoheptyloxy]-2-ethyl-4-formyl-5-hydroxy benzene (3.05 g, 10.7 mmol) and K$_2$CO$_3$ (2,43 g, 17.6 mmol) were stirred at room temp. To this mixture was added benzylbromide (3.66 g, 21.4 mmol), and the reaction was warmed to 75° C. After 19 h the reaction was cooled to room temp. and the solids were removed by filtration. The DMF was removed from the filtrate by vacuum distillation at 6 mHg, and the resulting material was dissolved in EtOAc and washed with water and brine. The organic layer was dried over MgSO$_4$. Filtration and solvent removal gave a white solid (4.52 g). The solid was recrystallized from Et$_2$O/Hexane to give 3.42 g (82%) of white flakes.

TLC Rf=0.40 (30% EtOAc/Hexane)

$^1$HNMR(CDCl$_3$)δ11.40(s,1), 9.71(s,1), 7.26(s,1), 6.42(s,1), 4.18(t,2,J=5.80 Hz), 3.77(t,2,J=6.28 Hz), 2.57(1,2,J=7.41 Hz), 2.30(m,2), 1.96(t,3,J=7.54 Hz)

IR(CHCl$_3$) 3021, 2971, 2937, 1643, 1586, 1494 cm$^{-1}$

Mass Spec(FD) m/e 303 (M+)

Elem Anal Calc'd for Cl$_2$H$_{15}$O$_3$Cl:

C,59.33; H, 6.23; Cl,14.61;

Found C,59.24; H, 6.18; Cl,14.69.

D. Preparation of 1-Benzyloxy-3-(6-cyano-6 methylheptyloxy)-4-ethyl-6-hydroxy benzene.

A solution of the aldehyde in CH$_2$Cl$_2$ (0.18M) at room temperature was treated with m-chloroperbenzoic acid (1.1 eqv), and the reaction was stirred at room temp. After 30 min. a ppt formed. The reaction was complete after 5 h. The precipitate was removed by filtration. The solvent was removed under vacuum and the resulting solid was dissolved in THF (0.28M) and stirred overnight with 2N NaOH (2.5 eqv). Subsequently, the THF was removed under vacuum, and the resulting aqueous mixture was diluted with H$_2$O and acidified to pH 1 with 1N HCl. The milky suspension was extracted several times with EtOAc. The organic extract was washed several times with saturated aqueous NaHCO$_3$ solution and then with brine. The organic layer was dried over MgSO$_4$. Filtration and solvent removal gave 8.70 g of a brown oil. The oil was purified by silica gel chromatography.

1-Benzyloxy-3-(6-cyano-6-methylheptyloxy)-4-ethyl -6-hydroxy benzene was obtained in 94% yield from 1-Benzyloxy-3-(6-cyano-6-methyl-heptyloxy)-4-ethyl-6-formyl benzene.

TLC Rf=0.38 (30% EtOAc/Hexane )

$^1$HNMR(CDCl$_3$)δ7.42(m,5), 6.79(s,1), 6.56(s,1), 5.30(s,1), 5.10(s,2), 3.89(t,2,J=6.25 Hz), 2.58(q,2,J=7.51 Hz), 1.82(m,1), 1.52(s(br), 6), 1.19(t,3,J=7.46 Hz)

IR(KBr) 3450, 2950, 2870, 2240, 1750, 1625, 1510 cm$^{-1}$

Mass Spec(FD) m/e 382(M++1)

Elem Anal Calc'd for C$_{24}$H$_{31}$NO$_3$

C,75.56; H,8.19; N,3.67;

Found C,74.91; H, 8.13,N, 4.11.

E. Preparation of 1-Benzyloxy-5-(6-cyano-6-methylheptyloxy)-4-ethyl-2-[1-(3-methyl-2-butenyl)]oxy benzene.

A THF solution (0.12M in phenol) of the phenol, triphenylphosphine (1.0 eqv) and the desired alcohol (1.0 eqv) was stirred at room temp under argon atmosphere. With stirring added diethylazo-dicarboxylate (1.0 eqv). The reaction was stirred at room temp for 16 h. The reaction solvent was then removed and the resulting residue was preabsorbed onto silica gel and purified by flash chromatography eluting with an ethyl acetate/hexane mixture.

1-Benzyloxy-5-(6-cyano-6-methylheptyloxy)-4-ethyl -2-[1-(3-methyl-2-butenyl)]oxy benzene was prepared in 92% yield as a white solid from 1-Benzyloxy-3-(6-cyano-6-methylheptyloxy)-4-ethyl-6-hydroxy benzene and 3-methyl-2-butene-1-ol.

TLC Rf=0.55 (30% EtOAc/Hexane)

$^1$HNMR(CDCl$_3$)δ7.39(m,5), 6.79(s,1), 6.50(s,1), 5.54(m,1), 5.13(s,2), 4.55(d,2,J=6.85 Hz), 3.84(t,2,J=6.23 Hz), 2.57(q, z, J=7.61 Hz), 1.78(m,5)1.71(s,3), 1.50(m,6), 1.37 (s,6), 1.18 (t, 3, J=7.55 Hz)

IR(CHCl$_3$) 3012, 2977, 2941, 2236, 1607, 1506, 1471, 1412 cm$^{-1}$

Mass Spec(FD) m/e 449(M+)

Elem Anal Calc'd for C$_{29}$H$_{39}$NO$_3$

C,77.47; H,8.74; N, 3.12;
Found C,78.49; H,8.55; N, 2.77.

F. Preparation of 1-[1-(3-methylbutyl)oxy]-2-hydroxy-4-(6-cyano-6-methylheptyloxy)-5-ethyl benzene.

To a solution of the benzyl ether in ethyl acetate or methanol (0.14M solution) was added 10% Pd/C (15% w/w). Hydrogen gas was bubbled through this solution for 15 min. The reaction was then stirred at room temp under an atmosphere of hydrogen. After starting material was consumed, argon was bubbled through the reaction mixture for 15 min. The reaction mixture was filtered through a celite pad in a sintered glass funnel, and the catalyst was washed with EtOAc. The resulting crude product was purified by flash chromatography using silica gel as the solid support and eluting with an ethyl acetate/hexane mixture.

1-[1-(3-methylbutyl)oxy]-2-hydroxy-4-(6-cyano-6-methylheptyloxy)-5-ethyl benzene was prepared from 1-Benzyloxy -5-(6-cyano-6-methylheptyloxy )-4-ethyl-2-[1-(3-methyl-2-butenyl)]oxy benzene in 91% yield.

TLC Rf=0.44 (30% EtOAc/Hexane)

$^1$HNMR(CDCl$_3$)δ6.70(s,1), 6.53(s,1), 5.53(s,1), 4.03(t,2,J=6.67(Hz), 3.91(t,2,J=6.24 Hz), 2.57(q,2,J=7.51 Hz), 1.81(m,2), 1.69(q,1,J=6.57 Hz), 1.56(m,8), 1.36(s,6), 1.17(t,6,J=7.50 Hz), 0.98(d,6,J=6.57 Hz)

IR(CHCl$_3$) 3541, 3019, 2962, 2873, 2236, 1604, 1508, 1471 cm$^{-1}$

Mass Spec(FD) m/e 361(M+)

Elem Anal Calc'd for C$_{22}$H$_{35}$NO$_3$:
C,73.09; H,9.76; N, 3.87;
Found C,73.36; H,9.68; N, 4.04.

G. 4-Ethyl-2-(3-methylbutoxy)-5-[[6-methyl-6-(2H-tetrazol-5-yl)heptyl]oxy]phenol sodium salt.

To a solution of the nitrile in ethyleneglycol diethylether (0.20M solution) under argon atmosphere added tri-n-butyltin azide (6.0 eqv). The reaction was then refluxed from 48 to 72 h. The reaction was then cooled to room temperature and treated with 5N HCl (11 eqv) and stirred for 2 h. The reaction mixture was then diluted with water and extracted with EtOAc. The ethyl acetate extract was dried over MgSO$_4$, filtered and solvent removed under vacuum to give an orange oil. The resulting oil was dissolved in Et$_2$O and treated with 1.1M aq KF solution (8.0 eqv), and stirred for 2.5 h. The resulting precipitate was removed by filtration. The solvent was removed from the filtrate and the remaining residue was triturated with hexane. The resulting solid was dissolved in methanol and treated with 2N NaOH 5 eqv), and stirred for 1.5 h. The solvent was then removed under vacuum, and the resulting solid was purified by reverse phase chromatography using CHP-20 resin and eluting with 60% MeOH/H2O. The desired product was obtained as a white lyophilate sodium salt.

4-Ethyl-2-(3-methylbutoxy)-5-[[6-methyl-6-(2H-tetrazol-5-yl)heptyl]oxy]phenol sodium salt was prepared in 43% yield from 1-(6-cyano-6-methylheptyloxy)-2-ethyl-4-(3-methylbutoxy)-5-hydroxy benzene.

TLC Rf=0.48 (10% MeOH/CH$_2$Cl$_2$)

$^1$HNMR(d$^6$-DMSO)δ9.70 (s(br),1) 6.62(s,1) 6.46(s,1) 3.86(t,2,J=6.74 Hz), 3.72(t,2,J=6.37 Hz), 2.38(q,2,J=7.48 Hz): 1.76(m,1), 1.54(m,4), 1.26(m,5), 1.21(s,6), 1.11(m,3), 1.02(t,3,J=7.46 Hz), 0.89 d,6,J=6.62 Hz)

IR 3415, 2960, 2930, 2860, 1610, 1516, 1466 cm$^{-1}$

Mass Spec (FAB) m/e 449(M+ +2Na+ +H), 427(M+ +Na+ +H), 404(M+)

Elem Anal Calc'd for C$_{22}$H$_{35}$N$_4$O$_3$Na-2.25H$_2$O:
C,56.52; H,8.52; N, 11.99;
Found C,56.26; H,8.00; N, 11.75.

EXAMPLE 6

Preparation of 2-(Cyclopentyloxy)-4-ethyl-5-[[6-methyl-6-(2H-tetrazol-5-yl)heptyl]oxy]phenol sodium salt, a compound represented by the formula:

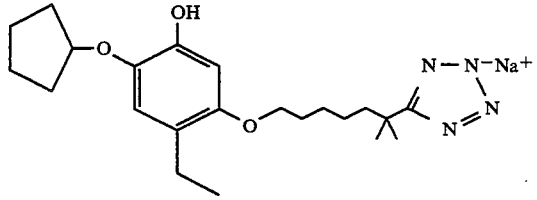

A. Preparation of 5-Ethyl-2,4-Dihydroxybenzaldehyde.

Dimethyformamide (250 mL) was cooled to 0° C. under argon atmosphere. With stirring, POCl$_3$ (18.60 mL, 0.20 mol) was added slowly to the DMF. After several minutes at 0° C., the reaction was warmed to room temp and CH$_2$Cl$_2$ (150 mL) was added to the reaction mixture to dissolve the solid. The reaction was subsequently recooled to 0° C. 4-Ethyresorcinol (25.0 g, 0.181 mol) was added to the reaction mixture as a 200 mL CH$_2$Cl$_2$ solution. After stirring at 0° C. for 10 min., the reaction was warmed to room temp and then refluxed for 16 h. The reaction was cooled to room temp, and a 100mL water solution of NaOAc (50 g) was added slowly. This mixture was refluxed for 40 min then cooled to room temp. The aqueous layer was washed several times with CH$_2$Cl$_2$. The organics were combined and washed with 1N HCl solution and brine the dried over MgSO$_4$. Filtration and solvent removal gave an orange solid which was recrystallized from toluene and hexane (17 g, 56%)

TLC Rf=0.39 (30% EtOAc/Hexane)

$^1$HNMR(CDCl$_3$)δ11.30(s,1), 9.71(s,1), 7.29 (s,1), 6.36(s(br),1), 2.61(q,2,J=7.48 Hz), 1.25(t,3,J=7.54 Hz)

B. Preparation of 1-[6-Methyl-6-cyanoheptyloxy]-2-ethyl-4-formyl-5-hydroxy benzene.

To a solution of 2-cyano-2-methyl-7-chloroheptane (15.01 g, 86.8 mmol) in 600 mL of acetone, added tetraethylammonium acetate tetrahydrate (45.36 g, 1.74 mol). The reaction was then refluxed under argon atmosphere for 25 h. The reaction was cooled to room temp and the acetone was removed under vacuum. To the resulting residue was added water and Et$_2$O. The aqueous layer was extracted with Et$_2$O several times and then dried over MgSO$_4$. Filtration and solvent removal gave a clear oil (23.19 g).

To the above prepared acetate in 400 mL of methanol added K$_2$CO$_3$ (16.27 g) and stirred at room temp for 24 h. The reaction mixture was filtered to remove the solids and the solvent was removed from the filtrate. The resulting solid was dissolved in EtOAc and the EtOAc solution was washed with H$_2$O. The organic solution was dried over MgSO$_4$. Filtration and solvent removal gave 14.50 g of a yellow oil which was purified by Waters Prep 500 chromatography using a silica gel support and eluting with a solvent gradient of 5% to 60% EtOAc/Hexane over 50 min. The desired alcohol was obtained as a clear oil (10.58 g, 57%).

TLC Rf=0.13 (30% EtOAc/Hexane)

A 50 mL dry THF solution of the above prepare 2-cyano-2-methyl-7-hydroxyheptane and 2,3-dihydroxy-4-ethylbenzaldehyde was stirred at room temp. To this solution added triphenylphosphine (17.91 g, 68.3 mmol) and finally diethyl azodicarboxylate (11.89 g, 68.3 mmol). The reaction was stirred at room temp for 2 h 15 min. and then quenched with saturated $NH_4Cl$ solution. The THF was removed under vacuum and the resulting residue was dissolved in EtOAc and the EtOAc solution was washed with brine. The organic layer was dried over $MgSO_4$. Filtration and solvent removal gave an orange solid. The product was purified by Waters Prep 500 chromatography using silica gel as a solid support and eluting with a gradient of 10% to 30% EtOAc/Hexane over 50 min. The desired product was obtained as a yellow oil (10.50 g, 51%).

$^1$HNMR(CDCl$_3$)$\delta$11.44(s,1), 9.67(s,1), 7.22(s,1), 4.02(t,2,J=6.22 Hz), 2.56(q,2,J=7.52 Hz), 1.85(m,2), 1.55(s(br),6), 1.34(s,6), 1.18(t,3,J=7.50 Hz)

IR(CHCl$_3$) 2980, 2944, 2860, 2230, 1640, 1585, 1493 cm$^{-1}$

Mass Spec(FD) m/e 303 (M+)

Elem Anal Calc'd for $C_{18}H_{25}NO_3$:

C,71.26; H, 8.31; N,4.62;

Found C,71.39; H, 8.10; N,4.75.

C. Preparation of 1-Benzyloxy-3-(6-cyano-6-methyl-heptyloxy)-4-ethyl-6-formyl benzene.

A solution of 40 mL of dry DMF, 1-[6-Methyl-6-cyanoheptyloxy]-2-ethyl-4-formyl-5-hydroxy benzene (3.05 g, 10.7 mmol) and $K_2CO_3$ (2,43 g, 17.6 mmol) were stirred at room temp. To this mixture was added benzylbromide (3.66 g, 21.4 mmol), and the reaction was warmed to 75° C. After 19 h the reaction was cooled to room temp. and the solids were removed by filtration. The DMF was removed from the filtrate by vacuum distillation at 6 mHg, and the resulting material was dissolved in EtOAc and washed with water and brine. The organic layer was dried over $MgSO_4$. Filtration and solvent removal gave a white solid (4.52 g). The solid was recrystallized from $Et_2O$/Hexane to give 3.42 g (82%) of white flakes.

TLC Rf=0.40 (30% EtOAc/Hexane)

$^1$HNMR(CDCl$_3$)$\delta$10.40(s,1), 7.67(s,1), 7.42(m,5), 6.45(s,1), 5.20(s,2), 4.00(t,2,J=6.15 Hz), 2.58(q,2,J=7.42 Hz), 1.86(m,2), 1.58(s(br),6), 1.37(s,6), 1.18(t,3,J=7.50 Hz)

IR(KBr) 2980, 2940, 2860, 2230, 1660, 1600, 1575 cm$^{-1}$

Mass Spec(FD) m/e 393 (M+)

Elem Anal Calc'd for $C_{25}H_3NO_3$:

C,76.30; H, 7.94; N,3.56;

Found C,76.54; H, 7.84; N,3.60.

D. Preparation of 1-Benzyloxy-3-(6-cyano-6-methyl-heptyloxy)-4-ethyl-6-hydroxy benzene.

A solution of the aldehyde in $CH_2Cl_2$ (0.18M) at room temperature was treated with m-chloroperbenzoic acid (1.1 eqv), and the reaction was stirred at room temp. After 30 min. a ppt formed. The reaction was complete after 5 h. The precipitate was removed by filtration. The solvent was removed under vacuum and the resulting solid was dissolved in THF (0.28M) and stirred overnight with 2N NaOH (2.5 eqv). Subsequently, the THF was removed under vacuum, and the resulting aqueous mixture was diluted with $H_2O$ and acidified to pH 1 with 1N HCl. The milky suspension was extracted several times with EtOAc. The organic extract was washed several times with saturated aqueous $NaHCO_3$ solution and then with brine. The organic layer was dried over $MgSO_4$.

Filtration and solvent removal gave 8.70 g of a brown oil. The oil was purified by silica gel chromatography.

1-Benzyloxy-2-(6-cyano -6-methylheptyloxy)-4-ethyl-6-hydroxy benzene was obtained in 94% yield from 1-Benzyloxy-2-(6-cyano-6-methyl-heptyloxy)-4-ethyl-6-formyl benzene.

TLC Rf=0.38 (30% EtOAc/Hexane)

$^1$HNMR(CDCl$_3$)$\delta$7.42(m,5) 6.79(s,1) 6.56(s,1) 5.30(s,1) 5.10(s,2), 3.89(t,2,J=6.25 Hz), 2.58(q,2,J=7.51 Hz), 1.82(m,1), 1.52(s(br),6), 1.19(t,3,J=7.46 Hz)

IR(KBr) 3450, 2950, 2870, 2240, 1750, 1625, 1510 cm$^{-1}$

Mass Spec(FD) m/e 382(M$^+$+1)

Elem Anal Calc'd for $C_{24}H_{31}NO_3$:

C,75.56; H,8.19; N,3.67;

Found C, 74.91; H, 8.13, N, 4.11.

E. Preparation of 1-Benzyloxy-3-(6-cyano-6-methyl-heptyloxy)-4-ethyl-6-cyclopentyloxy benzene.

A suspension of hexane washed NaH (2.10 eqv) in dry DMF (1.3M soln) was stirred under argon atm. at room temp. A solution of the phenol in dry DMF (0.15M) was added slowly to the NaH suspension. The reaction was stirred at room temp for 30 min. 18-Crown-6 was added to the reaction followed by the dropwise addition of alkyl halide (5.0 eqv). After stirring at room temp for several hours the reaction was quenched with saturated aqueous $NH_4Cl$ solution, diluted with water and extracted with EtOAc. The EtOAc extract was washed with water and then dried over $MgSO_4$. Filtration and solvent gave the crude product which was purified by silica gel flash chromatography.

1-Benzyloxy-2-(6-cyano-6-methylheptyloxy)-4-ethyl-6-cyclopentyloxy benzene was prepared in 92% yield as a white solid from 1-Benzyloxy-2-(6-cyano-6-methyl-heptyloxy)-4-ethyl-6-hydroxy benzene and bromocyclopentane.

TLC Rf=0.53 (30% EtOAc/Hexane)

$^1$HNMR(CDCl$_3$)$\delta$7.39(m,5), 6.78(s,1), 6.53(s,1), 5.10(s,2), 4.77(m,1), 3.87(t,2,J=6.22 Hz), 2.58(q, z, J=7.52 Hz), 1.86(m,7) 1.54(m,7), 1.37(s,6), 1.19(t,3,J=7.43 Hz), IR(CHCl$_3$) 3025, 3012, 2944, 2872, 2236, 1608, 1505, 1471, 1412 cm$^{-1}$ Mass Spec(FD) m/e 449(M+)

Elem Anal Calc'd for $C_{29}H_{39}NO_3$:

C,77.47; H,8.74; N, 3.12;

Found C,77.20; H,8.95; N, 3.23.

F. Preparation of 1-Cyclopentyloxy-2-hydroxy-4-(6-cyano-6-methylheptyloxy)-5-ethyl benzene To a solution of the benzyl ether in ethyl acetate or methanol (0.14M solution) was added 10% Pd/C (15% w/w). Hydrogen gas was bubbled through this solution for 15 min. The reaction was then stirred at room temp under an atmosphere of hydrogen. After starting material was consumed, argon was bubbled through the reaction mixture for 15 min. The reaction mixture was filtered through a celite pad in a sintered glass funnel, and the catalyst was washed with EtOAc. The resulting crude product was purified by flash chromatography using silica gel as the solid support and eluting with an ethyl acetate/hexane mixture.

1-Cyclopentyloxy-2-hydroxy-4-(6-cyano-6-methyl-heptyloxy)-5 -ethyl benzene was prepared from 1-Benzyloxy-5-(6-cyano-6methylheptyloxy)-4-ethyl-2-cyclopentyloxy benzene as a clear oil in 97% yield.

TLC Rf=0.44 (30% EtOAc/Hexane)

¹HNMR(CDCl₃)δ6.70(s,1), 6.52(s,1), 5.53(s,1), 4.70(m,1), 3.90(t,2,J=6.22 Hz), 2.57(q,2,J=7.50 Hz), 1.83(m,6), 1.64(m,2), 1.55(m,2), 1.36(s,6), 1.17(t,3,J=7.50 Hz)

IR(CHCl₃) 3550, 3013, 2968, 2945, 2873, 2238, 1600, 1506, 1471 cm⁻¹

Mass Spec(FD) m/e 359 (M+)

Elem Anal Calc'd for C₂₂H₃₃NO₃:
C,73.50; H,9.25; N, 3.90;
Found C,73.79; H,9.53; N, 3.73.

G. Preparation of 2-(Cyclopentyloxy)-4-ethyl-5-[[6-methyl-6-(2H-tetrazol-5-yl)heptyl]oxy]phenol sodium salt A solution of the nitrile in diglyme (0.4M solution) was treated with dimethylamino ethanol hydrochloride (2.0 eqv), dimethylamino ethanol (2.0 eqv) and sodium azide (5.0 eqv). The reaction mixture was then heated to 130° C. for 48 to 72 h. The reaction was then cooled to room temperature and quenched with 5N HCl and stirred for 2 h. The reaction mixture was diluted with water and extracted several times with ethyl acetate. The ethyl acetate extract was dried over MgSO₄, filtered and solvent removed to give a tan solid. The solid was dissolved in MeOH and treated with 3 eqv of NaOH. The methanol was removed, and the resulting solid was purified by reverse phase chromatography using CHP-20 resin and eluting with 60% MeOH/H2O. The desired product was obtained as a white lyophilate sodium salt.

2-(Cyclopentyloxy)-4-ethyl-5-[[6-methyl-6-(2H-tetrazol-5-yl)heptyl]oxy]phenol sodium salt was prepared in 34% yield from 1-cyclopentyloxy-2-hydroxy-4-(6-cyano-6-methylheptyloxy)-5-ethyl benzene via Method B.

TLC Rf=0.42 (10% MeOH/CH₂Cl₂)

¹HNMR(d⁶-DMSO)δ6.57(s,1), 6.47(s,1), 4.64(m,1), 3.72(t,2,J=6.45 Hz), 2.37(q,2,J=7.47 Hz), 1.70(S(br),6), 1.58(m,8), 1.26(m,4), 1.22(s,6), 1.09(m,4), 1.02 (t,3, J=7.41 Hz)

IR(KBr) 3423, 2960, 2869, 1608, 1527, 1464, 1389 cm⁻¹

Mass Spec(FAB) m/e 447(M++2Na+), 425(M++Na+)

Elem Anal Calc'd for C₂₂H₃₄N₄O₃Na-2.0H₂O:
C,57.19; H,8.29; N, 12.14;
Found C,57.28; H,8.32; N, 11.94.

EXAMPLE 7

Preparation of 4-Ethyl-2-(phenylthio)-5-[[6-methyl-6-(2H-tetrazol-5-yl)heptyl]oxy]phenol disodium salt, a compound represented by the formula:

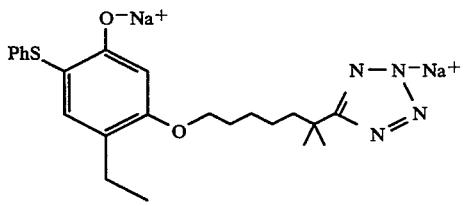

A. Preparation of 4-benzyloxy-2-hydroxy-1-acetophenone.

In a dry round-bottom flask under N₂, 2,4-dihydroxyacetophenone (15.2 g, 100 mmol) was dissolved in methyl ethyl ketone (400 ml) and DMSO (100 ml). To this solution were added benzyl bromide (17.0 g, 100 mmol) and K₂CO₃ (27.6 g, 200 mmol). The reaction was heated to reflux and stirred for 15 hours. The methyl ethyl ketone was removed in vacuo, and the DMSO solution was diluted with EtOAc and washed several times with brine. The organic material was collected, dried (MgSO₄), filtered, and concentrated to provide a dark solid. The solid was recrystallized from hexane/toluene to provide the benzyl ether as a tan solid 12.8 g, 55.7%);

mp 143°-144.5° C.;

NMR (CDCl₃)δ12.77 (s,1H), 7.70 (d, 1H, J=7 Hz), 7.3-7.5 (m,5H), 6.54 (d, 1H, J=7 Hz), 6.53 (s,1H), 5.11 (s,2H), 2.58 (s,3H);

Elem Anal. Calc'd for C₁₅H₁₂O₃: C 74.36; H 5.82.
Found: C, 74.52; H, 5.97.

B. Preparation of 2[6-methyl-6-cyanoheptyl]oxy-4-benzyloxy-1-acetophenone.

To a solution of 4-benzyloxy-2-hydroxy-1-acetophenone (9.65 g, 42 mmol) in DMF (150 ml) was added 2-cyano-2-methyl-7-chloroheptone (6.86 g, 40 mmol), K₂CO₃ (10.6 g, 77 mmol), and KI (1.6 g, 9.6 mmol). The reaction was heated to 90° C. and stirred for 24 hours. The solids were removed by filtration, and the DMF was removed in vacuo. The residue was purified by Prep-500 HPLC, using a gradient of 5% EtOAc in hexane to 20% over 30 minutes as a mobile phase to yield the pure ether as a clear oil (12.1 g, 79.8%);

NMR (CDCl₃)δ7.85 (d, 1H, J=7.4 Hz ), 7.3-7.5 (m,5H), 6.60 (dd, 1H, J=7.4, 1.8 Hz), 6.53 (d, 1H, J=1.8 Hz), 5.12 (s, 2H), 4.04 (t,2H, J=5.3 Hz), 2.61 (s,3H), 1.85-1.95 (m,2H), 1.5-1.6 (m,6H) 1.37 (s,6H); IR (CHCl₃) 2943, 2238, 1601 cm⁻¹; MS (m/e)379;

C. Preparation of 1-benzyloxy-3[6-methyl-6-cyanoheptyl]oxy-5-ethyl benzene.

To a solution of the 2[6-methyl-6-cyanoheptyl]oxy-4-benzyloxy-1-acetophenone (12.1 g, 31.6 mmol) in CCl₄ (30 ml) were added trifluoroacetic acid (44.4 g, 390 mmol) and triethylsilane (21.8 g, 188 mmol). The reaction was stirred at room temperature for 1.5 hours, then was worked-up by diluting with EtOAc and washing with aqueous Na₂CO₃. The organic material was collected, dried (MgSO₄), filtered, and concentrated in vacuo. The residue was purified by Prep-500 HPLC using a 3% EtOAc in hexane to 5% grade over 15 minutes, then holding at 5%. Concentration of the appropriate fractions provided the reduced product (10.6 g, 91.5%) as a clear liquid.

NMR CDCl₃δ7.35-7.5 (m,5H), 7.06 (d, 1H, J=6.5 Hz), 6.53 (s,1H), 6.52 (dd, 1H, J=6.5, 2 Hz), 5.06 (s,2H), 3.96 (t, 2H, J=5.3 Hz), 2.60 (q,2H, J=6.3 Hz), 1.8-1.85 (m,2H), 1.5-1.6 (m,6H), 1.37 (s,6H), 1.20 (t,3H, J=6.3 Hz);

D. Preparation of 1-bromo-2-benzyloxy-4[6-methyl-6-cyanoheptyl]oxy-5-ethyl benzene.

To a solution of 1-benzyloxy-3[6-methyl-6-cyanoheptyl]oxy-5-ethyl benzene (10.6 g, 28.9 mmol) in CCl₄ (125 ml) was added NBS (6.0 g, 33.3 mmol). Stirring was continued for 6 hours at room temperature. The mixture was then diluted with CH₂Cl₂ and washed with H₂O. The organic material was collected, dried (MgSO₄), filtered, and concentrated in vacuo. The residue was recrystallized from hexane/EtOAc to provide the aryl bromide (12.6 g, 97.8 %) as a pale yellow solid.

NMR (CDCl₃)δ7.35-7.5 (m,5H), 7.22 (s,1H), 6.50 (s,1H), 5.17 (s,2H), 3.90 (t,2H, J=5.3 Hz), 2.58 (q,2H,

J=6.3 Hz), 1.75–1.85 (m,2H), 1.50–1.65 (m,6H), 1.37 (s,6H), 1.18 (t, 3H, J=6.3 Hz);

IR (CHCl₃) 3020, 2981, 2946, 2238, 1662, 1600 cm⁻¹; MS (m/e) 444, 445, 446;

E. Preparation of 1-benzyloxy-5-[[6-cyano-6-methyl-5-yl)heptyl]oxy]-4-ethyl-2-(phenylthio)-benzene.

A solution of 1-bromo-2-benzyloxy-4[6-methyl-6cyanoheptyl]oxy-5-ethyl benzene (1.0 g, 2.25 mmol) in 50 mL of dry THF was cooled to −78° C. tert-Butyllithium (2.8 mL of a 1.7M hexane solution, 4.5 mmol) was added to the arylbromide solution and stirred for 30 min at −78° C. Diphenyldisulfide (1.0 g, 4,5 mmol) was then added to the anion solution and the mixture was stirred for 5 min at −78° C. and then warmed to room temperature. After stirring at room temp for 30 min., the reaction was quenched with aq saturated NH₄Cl and extracted with ethyl acetate. The organic extract was dried over MgSO₄, filtered and solvent removed to give the crude product. The crude product was purified by flash chromatography on silica gel eluting with 6% ethyl acetate/hexane. The thioether product was obtained in 80% yield.

¹HNMR(CDCl₃)δ7.10(m,6), 6.50(s,1), 5.10(s,2), 3.94(t,2,J=6.20 Hz), 2.54(q,2,J=7.50 Hz), 1.83(m,2), 1.58(s(br),6), 1.20(s,6), 1.18(t,3,J=7.50 Hz)

IR(CHCl₃) 3020, 2978, 2943, 2870, 2230, 1750, 1599, 1575, 1550, 1499 cm⁻¹

Mass Spec(FAB) m/e 473 (M⁺)

F. Preparation of 4-(6-cyano-6-methylheptyloxy)-5-ethyl-2-hydroxy-1-(phenylthio) benzene.

A solution of 1-benzyloxy-5-[[6-cyano-6-methyl-5-yl)heptyl]oxy]-4-ethyl-2-(phenylthio)-benzene (1.0 g) in CH₂Cl₂ (30 mL) was cooled to −78° C. To this solution added BBr₃ (2.1 mL of a 1.0M solution in CH₂Cl₂). Subsequently, the reaction was warmed to room temperature and quenched with water. The reaction mixture was extracted with CH₂Cl₂. The organic extract was dried over MgSO₄, filtered and concentrated under vacuum. The crude product was purified by flash chromatography on silica gel eluting with 5% ethyl acetate/hexane. The desired phenol was obtained in 74% yield.

¹HNMR(CDCl₃)δ7.00–7.40(m,7), 6.60(s,1), 6.40(s(br),1), 4.00(t,2,J=6.20 Hz), 2.60(q,2,J=7.50 Hz), 1.88(m,2), 1.60(s(br),6), 1.40(s,6), 1.20(t,3,7.50 Hz)

IR(CHCl₃) 3441, 3021, 2977, 2943, 2230, 1608, 1580, 1490 cm⁻¹

Mass Spec (FAB m/e 384 (M⁺ +H), 383 (M⁺)

G. Preparation of 4-ethyl-2-(phenylthio)-5-[[6-methyl-6-(2H-tetrazol-5-yl)heptyl]oxy]phenol disodium salt.

A solution of 4-(6-cyano-6-methylheptyloxy)-5-ethyl-2-hydroxy-1-(phenylthio) benzene (0. 680 g) in diglyme (5 mL) was treated with dimethylamino ethanol hydrochloride (0.80 g. 2.0 eqv), dimethylamino ethanol (0.36 g, 2.0 eqv) and sodium azide (0.50 g, 5.0 eqv),. The reaction mixture was then heated to 130° C. for 48 h. The reaction was then cooled to room temperature and quenched with 5N HCl and stirred for 2 h. The reaction mixture wa s diluted with water and extracted several times with ethyl acetate. The ethyl acetate extract was dried over MgSO₄, filtered and solvent removed to give a tan solid. The solid was dissolved in MeOH and treated with 3 eqv of NaOH. The methanol was removed, and the resulting solid was purified by reverse phase chromatography using CHP-20 resin and eluting with 60% MeOH/H₂O. The desired product was obtained as a white lyophilate sodium salt in 36% yield.

¹HNMR(d⁶DMSO)δ7.20(m,2), 7.00(m,4), 6.70(s,1), 3.82(m,2), 2.20(q,2,J=7.50 Hz), 1.62(m,4), 1.25(m,2), 1.20(s,6), 1.10 (m,2 ) 1.05 (t,3, J=7.50 Hz )

IR(KBr) 3430, 2935, 2880, 1605, 1581, 1478 cm⁻¹

Mass Spec (FAB) m/e 471 (M+2Na⁺+H), 449 (M⁺+Na⁺+H), 428 (M⁺+H)

Elem Anal Calc'd for C₂₃H₂₈N₄O₂SNa₂-0.5H₂O: C,57.62; H,6.05; N,11.69;

Found C,57.57; H,6.31; N,11.59.

EXAMPLE 8

Preparation of 2-[(4-Fluorophenyl)methoxy]-4-ethyl-5-[[6-methyl-6-(2H-tetrazol-5-yl)heptyl]oxy]-phenol sodium salt, a compound represented by the formula:

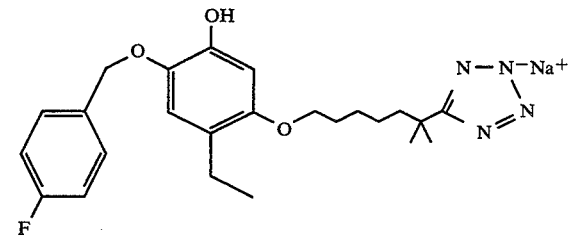

Preparation of 5-Ethyl-2,4-Dihydroxybenzaldehyde.

Dimethyformamide (250 mL) was cooled to 0° C. under argon atmosphere. With stirring, POCl₃ (18.60 mL, 0.20 mol) was added slowly to the DMF. After several minutes at O° C., the reaction was warmed to room temp and CH₂Cl₂ (150 mL) was added to the reaction mixture to dissolve the solid. The reaction was subsequently recooled to 0° C. 4-Ethyresorcinol (25.0 g, 0.181 mol) was added to the reaction mixture as a 200 mL CH₂Cl₂ solution. After stirring at 0° C. for 10 min., the reaction was warmed to room temp and then refluxed for 16 h. The reaction was cooled to room temp, and a 100 mL water solution of NaOAc (50 g) was added slowly. This mixture was refluxed for 40 min then cooled to room temp. The aqueous layer was washed several times with CH₂Cl₂. The organics were combined and washed with 1N HCl solution and brine the dried over MgSO₄. Filtration and solvent removal gave an orange solid which was recrystallized from toluene and hexane (17 g, 56%)

TLC Rf=0.39 (30% EtOAc/Hexane)

¹HNMR(CDCl₃)δ11.30(s,1), 9.71(s,1), 7.29(s,1), 6.36(s(br),2), 2.61(q,2,J=7.48 Hz), 1.25(t,3,J=7.54 Hz)

B. Preparation of 1-[6-Methyl-6-cyanoheptyloxy]-2-ethyl-4-formyl-5-hydroxy benzene.

To a solution of 2-cyano-2-methyl-7-chloroheptane (15.01 g, 86.8 mmol) in 600 mL of acetone, added tetraethylammonium acetate tetrahydrate (45.36 g, 1.74 mol). The reaction was then refluxed under argon atmosphere for 25 h. The reaction was cooled to room temp and the acetone was removed under vacuum. To the resulting residue was added water and Et₂O. The aqueous layer was extracted with Et₂O several times and then dried over MgSO₄. Filtration and solvent removal gave a clear oil (23.19 g).

To the above prepared acetate in 400 mL of methanol added K₂CO₃ (16.27 g) and stirred at room temp for 24 h. The reaction mixture was filtered to remove the solids and the solvent was removed from the filtrate. The resulting solid was dissolved in EtOAc and the EtOAc solution was washed with H₂O. The organic solution was dried over MgSO₄. Filtration and solvent removal gave 14.50 g of a yellow oil which was purified by Waters Prep 500 chromatography using a silica gel support and eluting with a solvent gradient of 5% to 60% EtOAc/Hexane over 50 min. The desired alcohol was obtained as a clear oil (10.58 g, 57%).

TLC Rf=0.13 (30% EtOAc/Hexane)

A 50 mL dry THF solution of the above prepare 2-cyano-2-methyl-7-hydroxyheptane and 2,3-dihydroxy-4-ethylbenzaldehyde was stirred at room temp. To this solution added triphenylphosphine (17.91 g, 68.3 mmol) and finally diethyl azodicarboxylate (11.89 g, 68.3 mmol). The reaction was stirred at room temp for 2 h 15 min. and then quenched with saturated NH$_4$Cl solution. The THF was removed under vacuum and the resulting residue was dissolved in EtOAc and the EtOAc solution was washed with brine. The organic layer was dried over MgSO$_4$. Filtration and solvent removal gave an orange solid. The product was purified by Waters Prep 500 chromatography using silica gel as a solid support and eluting with a gradient of 10% to 30% EtOAc/Hexane over 50 min. The desired product was obtained as a yellow oil (10.50 g, 51%).

$^1$HNMR(CDCl$_3$)δ11.44(s,1), 9.67(s,1), 7.22(s,1), 6.36(s,1), 4.02(t,2,J=6.22 Hz), 2.56(q,2,J=7.52 Hz), 1.85(m,2), 1.55(s(br),6), 1.34(s,6), 1.18(t,3,J=7.50 Hz)

IR(CHCl$_3$) 2980, 2944, 2860, 2230, 1640, 1585, 1493 cm$^{-1}$

Mass Spec(FD) m/e 303(M+)

Elem Anal Calc'd for C$_{18}$H$_{25}$NO$_3$:

C,71.26; H, 8.31; N,4.62;

Found C,71.39; H, 8.10; N,4.75.

C. Preparation of 1-Benzyloxy-3-(6-cyano-6-methylheptyloxy)-4-ethyl-6-formyl benzene.

A solution of 40 mL of dry DMF, 1-[6-Methyl-6-cyanoheptyloxy]-2-ethyl-4-formyl-5-hydroxy benzene 3.05 g, 10.7 mmol) and K$_2$CO$_3$ (2,43 g, 17.6 mmol) were stirred at room temp. To this mixture was added benzylbromide (3.66 g, 21.4 mmol), and the reaction was warmed to 75° C. After 19 h the reaction was cooled to room temp. and the solids were removed by filtration. The DMF was removed from the filtrate by vacuum distillation at 6 mHg, and the resulting material was dissolved in EtOAc and washed with water and brine. The organic layer was dried over MgSO$_4$. Filtration and solvent removal gave a white solid (4.52 g). The solid was recrystallized from Et$_2$O/Hexane to give 3.42 g (82%) of white flakes.

TLC Rf=0.40 (30% EtOAc/Hexane)

$^1$HNMR(CDCl$_3$)δ10.40(s,1), 7.67(s,1), 7.42(m,5), 6.45(s,1), 5.20(s,2), 4.00(t,2,J=6.15 Hz), 2.58(q,2,J=7.42 Hz), 1.58(s(br),6), 1.37(s,6), 1.18(t,3,J=7.50 Hz)

IR(KBr) 2980, 2940, 2860, 2230, 1660, 1600, 1575 cm$^{-1}$

Mass Spec(FD) m/e 393(M+)

Elem Anal Calc'd for C$_{25}$H$_3$NO$_3$:

C,76.30; H, 7.94; N,3.56;

Found C,76.54; H, 7.84; N,3.60.

D. Preparation of 1-Benzyloxy-3-(6-cyano-6-methylheptyloxy)-4-ethyl-6-hydroxy benzene.

A solution of the aldehyde in CH$_2$Cl$_2$ (0.18M) at room temperature was treated with m-chloroperbenzoic acid 1.1 eqv), and the reaction was stirred at room temp. After 30 min. a ppt formed. The reaction was complete after 5 h. The precipitate was removed by filtration. The solvent was removed under vacuum and the resulting solid was dissolved in THF (0.28M) and stirred overnight with 2N NaOH (2.5 eqv). Subsequently, the THF was removed under vacuum, and the resulting aqueous mixture was diluted with H$_2$O and acidified to pH 1 with 1N HCl. The milky suspension was extracted several times with EtOAc. The organic extract was washed several times with saturated aqueous NaHCO$_3$ solution and then with brine. The organic layer was dried over MgSO$_4$. Filtration and solvent removal gave 8.70 g of a brown oil. The oil was purified by silica gel chromatography.

1-Benzyloxy-3-(6-cyano-6-methylheptyloxy)-4-ethyl-6-hydroxy benzene was obtained in 94% yield from 1-Benzyloxy-2-(6-cyano-6-methyl-heptyloxy)-4-ethyl-6-formyl benzene.

TLC Rf=0.38 (30% EtOAc/Hexane)

$^1$HNMR(CDCl$_3$)δ7.42(m,5), 6.79(s,1), 6.56(s,1), 5.30(s,1), 5.10(s,2), 3.89(t,2,J=6.25 Hz), 2.58(q,2,J=7.51 Hz), 1.82(m,1), 1.52(s(br),6), 1.19(t,3,J=7.46 Hz)

IR(KBr) 3450, 2950, 2870, 2240, 1750, 1625, 1510 cm$^{-1}$

Mass Spec(FD) m/e 382(M+ +1)

Elem Anal Calc'd for C$_{24}$H$_{31}$NO$_3$:

C,75.56; H,8.19; N,3.67;

Found C,74.91; H,8.13, N,4.11.

E. Preparation of 1-Benzyloxy-5-(6-cyano-6-methylheptyloxy)-4-ethyl-2-(4-fluorobenzyl)oxy benzene.

A THF solution (0.12M in phenol) of the phenol, triphenylphosphine (1.0 eqv) and the desired alcohol (1.0 eqv) was stirred at room temp under argon atmosphere. With stirring added diethylazo-dicarboxylate (1.0 eqv). The reaction was stirred at room temp for 16 h. The reaction solvent was then removed and the resulting residue was preabsorbed onto silica gel and purified by flash chromatography eluting with an ethyl acetate/hexane mixture.

1-Benzyloxy-5-(6- cyano-6-methylheptyloxy )-4-ethyl-2-(4-fluorobenzyl)oxy benzene was prepared in 52% yield as a white solid from 1-Benzyloxy-2-(6-cyano-6-methylheptyloxy)-4-ethyl-6-hydroxy benzene and 4-fluorobenzyl alcohol.

TLC Rf=0.55 (30% EtOAc/Hexane)

$^1$HNMR(CDCl$_3$)δ7.46(m,5), 7.07(d,2,J=8.70 Hz), 7.05(d,2,J=8.70 Hz), 6.87(s,1), 6.61(s,1), 5.17(s,2), 5.07(s,2), 3.92(t,2,J=6.20 Hz), 2.63(q,2,J=7.51 Hz), 1.85 m,2), 1.60(m,6), 1.39(s,6), 1.23(t,3,J=7.44 Hz)

IR(KBr) 3066, 2976, 2938, 2858, 2232, 1608, 1553, 1462 cm$^{-1}$

Mass Spec(FAB) m/e 489(M+)

Elem Anal Calc'd for C$_{31}$H$_{36}$NO$_3$:

C,76.05; H,7.41; N, 2.86;

Found C,76.28; H,7.70; N, 3.16.

F. Preparation of 1-(4-Fluorobenzyl)oxy-2-hydroxy-4-(6-cyano-6-methylheptyloxy)-5-ethyl benzene.

To a solution of the benzyl ether in ethyl acetate or methanol (0.14M solution) was added 10% Pd/C (15% w/w). Hydrogen gas was bubbled through this solution for 15 min. The reaction was then stirred at room temp under an atmosphere of hydrogen. After starting material was consumed, argon was bubbled through the reaction mixture for 15 min. The reaction mixture was filtered through a celite pad in h sintered glass funnel, and the catalyst was washed with EtOAc. The resulting crude product was purified by flash chromatography using silica gel as the solid support and eluting with an ethyl acetate/hexane mixture.

1-(4-Fluorobenzyl)oxy-2-hydroxy-4-(6-cyano-6-methylheptyloxy)-5-ethyl benzene was prepared from 1-Benzyloxy-5-(6-cyano-6-methylheptyloxy)-4-ethyl-2-(4-fluorobenzyl)oxy benzene as a clear oil in 85% yield.

TLC Rf=0.36 (30% EtOAc/Hexane)

1HNMR(CDCl3)δ7.40(d,1,J=5.48 Hz), 7.37(d,1,J=5.42 Hz), 7.08 (d, 1 ,J=8.66 (Hz), 7.06(d,1,J=8.66 Hz), 6.77(s,1), 6.55(s,1), 5.75(s,1), 5.00(s,2), 3.90(t,2,J=6.20 Hz), 2.60 (dd,2,J=7.48 Hz), 1.82(m,2), 1.57(s(br),6), 1.36(s,6), 1.19 (t,3,J=7.45 Hz).

IR(CHCl3) 3546, 2977, 2943, 2873, 2250, 1604, 1513, 1471 cm$^{-1}$

Mass Spec(FAB) m/e 399(M+)

Elem Anal Calc'd for $C_{24}H_{30}NO_3$:
C,72.16; H,7.57; N, 3.51;
Found C,71.86; H,7.66; N, 3.27.

G. Preparation of 2-[(4-fluorophenyl)methoxy]-4-ethyl-5-[[6-methyl-6-(2H-tetrazol-5-yl)heptyl]oxy]-phenol sodium salt.

A solution of the nitrile in diglyme (0.4M solution) was treated with dimethylamino ethanol hydrochloride (2.0 eqv), dimethylamino ethanol (2.0 eqv) and sodium azide (5.0 eqv). The reaction mixture was then heated to 130° C. for 48 to 72 h. The reaction was then cooled to room temperature and quenched with 5N HCl and stirred for 2 h. The reaction mixture was diluted with water and extracted several times with ethyl acetate. The ethyl acetate extract was dried over MgSO4, filtered and solvent removed to give a tan solid. The solid was dissolved in MeOH and treated with 3 eqv of NaOH. The methanol was removed, and the resulting solid was purified by reverse phase chromatography using CHP-20 resin and eluting with 60% MeOH/H2O. The desired product was obtained as a white lyophilate sodium salt.

2-[(4-fluorophenyl)methoxy]-4-ethyl-5-[[6-methyl-6-(2H-tetrazol-5-yl)heptyl]oxy]phenol sodium salt was prepared in 43% yield from 1-(4-fluorobenzyl)oxy-2-hydroxy-4-(6-cyano-6-methylheptyloxy)-5-ethyl benzene.

TLC Rf=0.45 (10% MeOH/CH2Cl2 )

1HNMR(d$^6$-DMSO)δ10.10(S(br),1), 7.48(dd,2,J=8.51, 5.78 Hz), 7.18(d,1,J=8.89 Hz), 7.15(d,1,J=8.90 Hz), 6.69(s,1), 6.51(s,1), 4.94(s,2), 3.72(t,2,J=6.38 Hz), 2.36(q,2,J=7.49 Hz), 1.57(m,4), 1.27(m,2), 1.22(s,6), 1.10(m,2), 1.00(t,3,J=7.43 Hz)

IR (KBr) 3482 2941 2857 1607 1512 1466 cm$^{-1}$

Mass Spec (FAB) m/e 487 (M++2Na+), 465 (M++Na++H)

Elem Anal Calc'd for $C_{24}H_{30}N_4O_3FNa \cdot 2.2H_2O$:
C,57.13; H,6.87; N, 11.11;
Found C,57.08; H,6.75; N, 10.98.

EXAMPLE 9

Preparation of 3,4-Dihydro-8-propyl-7-[3-(2-ethyl-5-hydroxy-4-methoxy-phenoxy)propoxy]-2H-1-benzopyran-2-carboxylic acid, a compound represented by the formula:

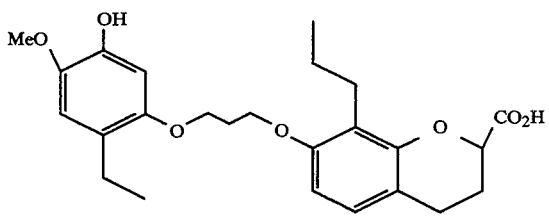

A. Preparation of 5-Ethyl-2,4-Dihydroxybenzaldehyde.

Dimethyformamide (250 mL) was cooled to 0° C. under argon atmosphere. With stirring, POCl3 (18.60 mL, 0.20 mol) was added slowly to the DMF. After several minutes at 0° C., the reaction was warmed to room temp and CH2Cl2 (150 mL) was added to the reaction mixture to dissolve the solid. The reaction was subsequently recooled to 0° C. 4-Ethyresorcinol (25.0 g, 0.181 mol) was added to the reaction mixture as a 200 mL CH2Cl2 solution. After stirring at 0° C. for 10 min., the reaction was warmed to room temp and then refluxed for 16 h. The reaction was cooled to room temp, and a 100 mL water solution of NaOAc (50 g) was added slowly. This mixture was refluxed for 40 min then cooled to room temp. The aqueous layer was washed several times with CH2Cl2. The organics were combined and washed with 1N HCl solution and brine the dried over MgSO4. Filtration and solvent removal gave an orange solid which was recrystallized from toluene and hexane (17 g, 56%)

TLC Rf=0.39 (30% EtOAc/Hexane)

1HNMR(CDCl3)δ11.30(s,1), 9.71(s,1), 7.29(s,1), 6.36(s(br),1), 2.61(q,2,J=7.48 Hz), 1.25(t,3,J=7.54 Hz)

B. Preparation of Chromone

To a solution of 225 mL of EtOH(Abs) under argon atm. and at room temp added 16.56 g of Na metal over a 1 h. period. After all of the Na was added the reaction mixture was refluxed for 1 h. then cooled to room temp. A mixture of 2,4-dihydroxyacetophenone (34.82 g, 0.180 mol), diethyloxylate (54.57 mL, 0.41 mol), absolute EtOH (45 mL), and diethylether (45 mL) was added to the sodium ethoxide solution over 25 min. The resulting deep maroon reaction mixture was then refluxed for 2.5 h and then cooled to room temp. The reaction mixture was poured into approx. 600 mL of 1N HCl and then extracted several times with Et2O. The ether was removed form the extract and the resulting gum was dissolved in 135 mL of EtOH. To this solution was then added 2.25 mL of conc. HCl and subsequently refluxed for 45 min. The reaction was cooled to room temp and EtOH was removed under reduced pressure leaving a brown solid. This solid was dissolved in EtOAc and washed 1 x with H2O, 2 x's with sat'd NaHCO3, 1 x with H2O and then dried over MgSO4. Filtration and solvent removal gave 87 g of a brown solid which was recrystallized from EtOAc/petroleum ether. Recrystallization provided 24.07 g (48%) of a tan solid chromone.

TLC: Rf=0.27 (40% EtOAc/Hexane).

1H NMR (CDCl3)δ8.80 (s(br),1), 7.98 (d,1,J=8.78 Hz), 7.13 (d,1,J=8.78 Hz), 7.13(s,1), 4.47 (q,2,J=7.11 Hz), 2.96 (t,2,J=7.25 Hz), 1.73 (m,2), 1.46 (t,3,J=7.16 Hz ), 1.02 (t,3,J=7.11 Hz ).

C. Preparation of Ethyl 3,4-dihydro-8-propyl-2H-1-benzopyran-2-carboxylate.

In a parr bottle, chromone (12.07 g, 0.044 mol) was dissolved in 210 mL of acetic acid. 10% Pd/C (7.2 g) catalyst was added to this solution and the bottle was pressurized with 52 psi of H2 gas. The reaction was agitated for 23 h. The catalyst was removed by filtration through a celite pad in a sintered glass funnel. The catalyst was washed with EtOAc. The solvent was removed from the filtrate and the resulting oil was azeotroped with toluene providing 12 g of brown oil. The material was purified on a Waters Prep 500 HPLC, equiped with silica gel cartridges, running a 5% to 40% EtOAc/Hexane gradient over 50 min at a flow rate of 250 mL/min and collecting 500 mL fractions. The purified chroman was obtained as a pink oil (10 g, 86%).

TLC: Rf=0.50 (40% EtOAc/Hexane).

1H NMR (CDCl3)δ6.73 (d,1 J=8.20 Hz) 6.37 (d,1,J=8.20 Hz), 4.78 (s(br), 1), 4.75 (m,1), 4.25 (m,2), 2.68 (m, 4), 2.16 (m,2), 1.60 (m,2), 1.29 (t,3,J=7.07 Hz), 0.99 (t,3,J=7.34 Hz).

D. Preparation of ethyl 3,4-dihydro-7-[1-(3-hyroxypropoxy)]-8-propyl-2H-1-benzopyran-2-carboxylate.

A 30 mL dry DMF solution of ethyl 3,4-dihydro-8-propyl-2H-1-benzopyran-2-carboxylate (2.04 g, 7.73 mmol) was stirred with $K_2CO_3$ (3.20 g, 23.2 mmol) at room temperature. To the reaction mixture was added allylbromide (1.87 g, 15.5 mmol). The reaction was stirred at room temp for 20 h and then diluted with water and extracted several times with ethyl acetate. The EtOAc extract was washed with water and then dried over $MgSO_4$. Filtration and solvent removal gave 2.23 g of the allyl ether as a clear oil.

The allyl ether was then dissolved in dry THF (35 mL) under argon atmosphere. To this solution added 9-BBN (14.40 mL, 7.19 mmol) over 5 min. The reaction was stirred at room temperature for 3 h.

Subsequently, 2.88 mL of 3.5M NaOH was added slowly to the reaction mixture followed by 30% $H_2O_2$ (2.88 mL). After 1 h at room temperature the reaction was diluted with water and extracted several times with EtOAc. The organic extract was dried over $MgSO_4$, filtered and the solvent removed under vacuum to leave 2.82 g of a yellow oil. The crude product was purified by Waters Prep 500 chromatography using a silica gel support and eluting with an solvent gradient of 5% to 50% EtOAc/Hexane. The desired product (1.43 g, 62%) was obtained as a clear oil.

TLC Rf=0.17 (30% EtOAc/Hexane)
$^1$HNMR δ6.82 (1,d,J=8.38 Hz), 6.47 (1,d,J=6.38 Hz), 4.76(dd, 1,J=6.41, 4.16 Hz), 4.24(m,2), 4.10(t,2,J=6.21 Hz), 3.90(m,2, 2.73(m,2), 2.64(m,2), z,14(m,2), 1.92(m,1), 1.57(m,2 , 1.29(t,3,J=6.90 Hz), 0.96(t,3.J=7.35 Hz)
IR(CHCl3) 3425, 3025, 1600, 1687, 1675, 1600 cm$^{-1}$
Mass Spec(FD) m/e 322(M$^+$)
Elem Anal Calc'd for $C_{18}H_{26}O_5$:
C,67.06; H, 8.13;
Found C,67.26; H, 8.10.

E. Preparation of ethyl 7-[3-[(6-formyl-4-ethyl-1-hydroxy3-yl)oxy]propoxy]-3,4-dihydro-8-propyl-2H-1-benzopyran-2-carboxylate A solution of 3,4-dihydro-7-[1-(3-hyroxypropoxy)]-8-propyl2H-1-benzopyran-2-carboxylate (2.21 g, 6.82 mmol), 5-ethyl2,3-dihydroxybenzaldehyde (1.13 g, 6.82 mmol) and triphenylphosphene (1.80 g, 6.82 mmol) in dry THF (45 mL) was stirred at room temperature. To this solution was added diethyl azodicarboxylate (1.19 g, 6.82 mmol), and the reaction was stirred at room temp for 4.5 h. The reaction was quenched with water and then extracted with ethyl acetate. The ethyl acetate extract was washed with water and brine and then dried over $MgSO_4$. Filtration and solvent removal gave an orange material which was purified by flash chromatography on silica gel eluting with 20% EtOAc/Hexane. The desired product was obtained as a clear oil (2.04 g) in 63% yield.

TLC Rf=0.29 (20% EtOAc/Hexane)
$^1$HNMR(CDCl3)δ11.46(s,1), 7.26(d,1,J=8.93 Hz), 6.81(d,1,J=S.40 Hz), 6.47(d,1,J=8.40 Hz), 6.43(s,1), 4.75(dd, 1,J=6.43,4.20 Hz), 4.23(m,5), 4.14(t,2,J=6.00 Hz), 2.65(m,3), 2.62(m,2), 2.29(m,2), 2.14(m,2), 1.55(m,2), 1.28(t,3,J=7.12 Hz), 1.19(t,3,J=7.60 Hz), 0.93(t,3,J=7.40 Hz), IR(CHCl3) 2965, 2934, 1749, 1728, 1641, 1613, 1587 cm$^{-1}$
Mass Spec (FD) m/e 470 (M$^+$)
Elem Anal Calc'd for $C_{27}H_{34}O_7$:
C, 68.92; H, 7.28;
Found C,69.02; H, 7.23.

F. Preparation of ethyl 7-[3-[(1-benzyloxy-6-formyl-4-ethyl-3-yl)oxy]propoxy]-3,4-dihydro-8-propyl-2H-1-benzopyran-2-carboxylate.

A solution of 20 mL of dry DMF, ethyl 7-[3-[(6-formyl-4-ethyl-1-hydroxy-3-yl) oxy]propoxy]-3,4-dihydro-8-propyl-2H-1 -benzopyran-2-carboxylate (1.97 g, 4.18 mmol) and $K_2CO_3$ (0.960 g, 7.31 mmol) were stirred at room temp. To this mixture was added benzylbromide (1.43 g, 8.36 mmol), and the reaction was warmed to 75° C. After 17 h the reaction was cooled to room temp. The reaction was quenched with water and the resulting mixture was extracted with EtOAc. The organic extract was washed with water and brine. The organic layer was dried over $MgSO_4$. Filtration and solvent removal gave a yellow oil. The oil was purified via Waters Prep 500 chromatography using a silica gel support and eluting with a solvent gradient of 5% to 35% EtOAc/Hexane over 45 min. The desired product was obtained as a white solid (2.41 g).

TLC Rf=0.39 (30% EtOAc/Hexane)
$^1$HNMR(CDCl3)δ10.40(s,1), 7.68(s,1), 7.57(m,5), 6.82(d,1,J=8.40 Hz), 6.50(s,1), 6.46(d,1,J=8.41 Hz) 5.16(s,2), 4.74(dd, 1,J=6.50, 4.16 Hz), 4.24(m,4), 4.15(t,2,J=5.85 Hz), 2.67(m,4), 2.55(q,2,J=7.45 Hz), 2.31(m,2), 2.19(m,2), 1.55 (m,2), 1.29 (t,3,J=7.07 Hz), 1.18 (t,3,J=7.48 Hz), 0.94 (t,3,J=7.34 Hz )
IR(KBr) 3292, 3475, 1750, 1725, 1641, 1587 cm$^{-1}$
Mass Spec (FAB) m/e 561 (M$^+$+1)
Elem Anal Calc'd for $C_{24}H_{46}O_7$:
C,72.86; H,7.14;
Found C, 73.07; H,7.41.

G. Preparation of Ethyl 7-[3-[(1-benzyloxy-6-hydroxy-4-ethyl-3-yl) oxy]propoxy]-3,4-dihydro-8-propyl-2H-1-benzopyran-2-carboxylate.

A solution of the aldehyde in $CH_2Cl_2$ (0.18M) at room temperature was treated with m-chloroperbenzoic acid (1.1 eqv), and the reaction was stirred at room temp. After 30 min. a ppt formed. The reaction was complete after 5 h. The precipitate was removed by filtration. The solvent was removed under vacuum and the resulting solid was dissolved in THF (0.28M) and stirred overnight with 2N NaOH (2.5 eqv). Subsequently, the THF was removed under vacuum, and the resulting aqueous mixture was diluted with $H_2O$ and acidified to pH 1 with 1N HCl. The milky suspension was extracted several times with EtOAc. The organic extract was washed several times with saturated aqueous $NaHCO_3$ solution and then with brine. The organic layer was dried over $MgSO_4$. Filtration and solvent removal gave 8.70 g of a brown oil. The oil was purified by silica gel chromatography.

Ethyl 7-[3-[(1-benzyloxy-6-hydroxy-4-ethyl-3-yl ) oxy]propoxy]-3,4-dihydro-8-propyl-2H-1-benzopyran-2-carboxylate was obtained in 27% yield from ethyl 7-[3-[(1-benzyloxy-6-formyl-4-ethyl-3-yl )oxy]propoxy]-3,4-dihydro-8-propyl-2H-1-benzopyran-2-carboxylate.

TLC Rf=0.37 (30% EtOAc/Hexane)
$^1$HNMR(CDCl3)δ7.43(m,5), 6.86(d,1,J=8.40 Hz), 6.83(s,1), 6.62(s,1), 6.53(d,1,J=8.40 Hz), 5.39(s,1), 5.06(s,1), 4.76(dd, 1,J=6.50, 4.21 Hz), 4.27(m,2), 4.18(m,2), 2.74(m,4), 2.62(q,2,J=7.44 Hz), 2.26(m,4), 1.65(m,2), 1.33(t,3,J=7.07 Hz), 1.22(t,3,J=7.45 Hz), 1.01(t,3,J=7.33 Hz), IR(CHCl₃) 3643, 3579, 3029, 2979, 2943, 2800, 1757, 1729, 1620, 1586, 1514 cm⁻¹

Mass Spec (FAB) m/e 548 (M+)
Elem Anal Calc'd for C₁₃H₄₀O₇-0.1 H₂O:
C,71.94; H,7.36;
Found C, 71.37; H, 7.52.

H. Preparation of Ethyl [3-[(1-benzyloxy-4-ethyl-2-methoxy-5-yl)oxy]propoxy]-3,4-dihydro-8-propyl-2H-1-benzopyran-2-carboxylate A suspension of hexane washed NaH (2.10 eqv) in dry DMF (1.3M soln) was stirred under argon atm. at room temp. A solution of the phenol in dry DMF (0.15M) was added slowly to the NaH suspension. The reaction was stirred at room temp for 30 min. 18-Crown-6 was added to the reaction followed by the dropwise addition of alkyl halide (5.0 eqv). After stirring at room temp for several hours, the reaction was quenched with saturated aqueous NH₄Cl solution, diluted with water and extracted with EtOAc. The EtOAc extract was washed with water and then dried over MgSO₄. Filtration and solvent gave the crude product which was purified by silica gel flash chromatography.

Ethyl [3-[(1-benzyloxy-4-ethyl-2-methoxy-5-yl)oxy]propoxy]-3,4-dihydro-8-propyl-2H-1-benzopyran-2-carboxylate was prepared in 84% yield as a clear oil from ethyl 7-[3-[(1-benzyloxy-6-hydroxy-4-ethyl-3-yl)oxy]propoxy]-3,4-dihydro-8-propyl-2H-1-benzopyran-2-carboxylate.

TLC Rf=0.48 (30% EtOAc/Hexane)
¹HNMR(CDCl₃)δ7.43(m,5), 6.85(d,2,J=8.40 Hz), 6.80(s,1), 6.61(s,1), 6.51(d,2,J=8.40 Hz), 5.15(s,2), 4.78(dd, 1,J=6.44,4.25 Hz), 4.27(m,2), 4.16(t,2,J=6.00 Hz), 4.10(t,2,J=6.00 Hz), 3.90(s,3), 2.69(m,6), 2.24(m,4), 1.64(m,2), 1.32(t,3,J=7.06 Hz), 1.23(t,3,J=7.53 Hz), 1.00 (t,3,J=7.35 Hz)

IR(CHCl₃) 3031, 3015, 2977, 2946, 2870, 1750, 1730, 1630, 1600, 1515, 1450 cm⁻¹

Mass Spec (FAB) m/e 562 (M+)
Elem Anal Calc'd for C₃₄H₄₂O₇:
C,72.57; H,7.52;
Found C, 73.85; H,7.40.

I. Preparation of Ethyl [3-[(6-ethyl-3-hydroxy-4-methoxy-1-yl)oxy]propoxy]-3,4-dihydro-8-propyl-2H-1-benzopyran-2-carboxylate.

To a solution of the benzyl ether in ethyl acetate or methanol (0.14M solution) was added 10% Pd/C (15% w/w). Hydrogen gas was bubbled through this solution for 15 min. The reaction was then stirred at room temp under an atmosphere of hydrogen. After starting material was consumed, argon was bubbled through the reaction mixture for 15 min. The reaction mixture was filtered through a celite pad in a sintered glass funnel, and the catalyst was washed with EtOAc. The resulting crude product was purified by flash chromatography using silica gel as the solid support and eluting with an ethyl acetate/hexane mixture.

Ethyl [3-[(6-ethyl-3-hydroxy-4-methoxy-1-yl)oxy]propoxy]-3,4-dihydro-8-propyl-2H-1-benzopyran-2-carboxylate was prepared from ethyl [3-[(1-benzyloxy-4-ethyl-2-methoxy-5-yl)oxy]propoxy]-3,4-dihydro-8-propyl-2H-1-benzopyran-2-carboxylate in 91% yield.

TLC Rf=0.32 (30% EtOAc/Hexane)
¹HNMR(CDCl₃)δ6.81(d,1,J=8.32 Hz), 6.70(s,1), 6.57(s,1), 6.47(d,1,J=8.32 Hz), 5.51(s,1), 4.75(dd,1,J=6.63,4.13 Hz), 4.23(m,2), 4.12(m,4), 3.86(s,3), 2.65(m,6), 2.23(m,4), 1.60(m,2), 1.29(t,3,J=7.18 Hz), 1.17(t,3,J=7.43 Hz), 0.94 (t,3,J=7.32 Hz)

IR(CHCl₃) 3546, 3022, 2964, 2877, 1762, 1730, 1615, 1585, 1510 cm⁻¹

Mass Spec (FAB) m/e 472 (M+)
Elem Anal Calc'd for C₂₇H₃₆O₇:
C, 68.62; H,7.68;
Found C, 68.88; H,7.40.

J. Preparation of 3,4-dihydro-8-propyl-7-[3-(2-ethyl-5-hydroxy-4-methoxy-phenoxy)propoxy]-2H-1-benzopyran-2-carboxylic acid.

The ethyl ester was stirred in dioxane (0.14M solution) at room temperature. This solution was treated with 3.0 eqv of NaOH (2N aq solution). The reaction was stirred at room temperature for 2.5 h and then the dioxane was removed under vacuum. The resulting residue was dissolved in water and acidified to pH 1 with 5N HCl (a white ppt. forms). The aqueous mixture was extracted several times with ethyl acetate and then dried over MgSO₄. Filtration and solvent removal gave the crude product.

3,4-dihydro-8-propyl-7-[3-(2-ethyl-5-hydroxy-4-methoxyphenoxy)propoxy]-2H-1-benzopyran-2-carboxylic acid was purified by flash chromatography on silica gel eluting with 6.5/3.4/0.1 EtOAc/Hexane/AcOH. The desired acid was obtained as a white solid (0.115 g, 41%)

TLC Rf=0.38 (6.5/3.4/0.1 EtOAc/Hexane/AcOH)
¹HNMR(CDCl₃)δ6.84(d,1,J=8.40 Hz), 6.70(s,1), 6.56(s,1), 6.51(d,1,J=8.40 Hz), 4.76(dd, 1,J=8.40, 3.72 Hz), 4.15(t,2,J=6.10 Hz), 4.11(t,2,J=6.28 Hz), 3.86(s,3), 2.78(m,2), 2.63(m,4), 2.27(m,4), 1.54(m,2), 1.17(t,3,J=7.46 Hz), 0.94(t,3,J=7.30 Hz)

IR(KBr) 3430, 2957, 2945, 2885, 1701, 1612, 1515, 1464 cm⁻¹

Mass Spec (FAB) m/e 444 (M+)
Elem Anal Calc'd for C₂₅H₃₂O₇:
C,67.55; H,7.26;
Found C, 66.29; H, 6.86.

EXAMPLE 10

Preparation of 3,4-Dihydro-8-propyl-7-[3-(2-ethyl-5-hydroxy-4-ethoxy-phenoxy)propoxy]-2H-1-benzopyran-2-carboxylic acid, a compound represented by the formula:

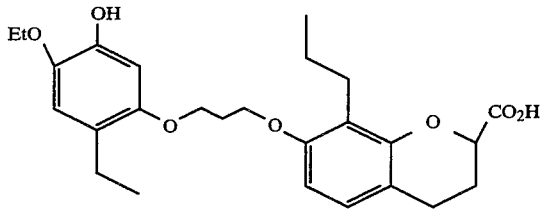

A. Preparation of 5-Ethyl-2,4-Dihydroxybenzaldehyde.

Dimethyformamide (250 mL) was cooled to 0° C. under argon atmosphere. With stirring, POCl₃ (18.60 mL, 0.20 mol) was added slowly to the DMF. After several minutes at 0° C., the reaction was warmed to room temp and CH₂Cl₂ (150 mL) was added to the reaction mixture to dissolve the solid. The reaction was subsequently recooled to 0° C. 4-Ethyresorcinol (25.0 g, 0.181 mol) was added to the reaction mixture as a 200 mL CH₂Cl₂ solution. After stirring at 0° C. for 10 min., the reaction was warmed to room temp and then refluxed for 16 h. The reaction was cooled to room temp, and a 100 mL water solution of NaOAc (50 g) was added slowly. This mixture was refluxed for 40 min then cooled to room temp. The aqueous layer was washed several times with CH$_2$Cl$_2$. The organics were combined and washed with 1N HCl solution and brine the dried over MgSO$_4$. Filtration and solvent removal gave an orange solid which was recrystallized from toluene and hexane (17 g, 56%)

TLC Rf=0.39 (30% EtOAc/Hexane)

$^1$HNMR(CDCl$_3$)δ11.30(s,1), 9.71(s,1), 7.29(s,1), 6.36(s(br),1), 2.61(q,2,J=7.48 Hz), 1.25(t,3,J=7.54 Hz)

B. Preparation of 1-(3-chloropropoxy-1-yl)-3-hydroxy-4-formyl-5-ethyl benzene.

A 190 mL dry THF solution of 5-ethyl-2,4-dihydroxybenzaldehyde (8.00 g, 48.1 mmol), 3-chloropropanol (4.55 g, 48.1 mmol) and triphenylphosphine (12.62 g, 48.1 mmol) were stirred at room temperature. To this solution was added a 10 mL THF solution of diethyl azodicarboxylate (7.60 mL, 48.1 mmol). The reaction was stirred at room temperature for 17 h after which the solvent was removed under vacuum. The crude material was adsorbed onto 125 g of Merck 60μ silica gel and then eluted through a plug 100 mL plug of Merck silica gel with 1 L of 30% EtOAc/Hexane. The resulting yellow oil was then further purified by Waters Prep 500 chromatography on silica gel eluting with a solvent gradient of 5% to 30% EtOAc/Hexane over 45 min. The desired product was obtained as a clear oil (7.03 g, 61%).

TLC Rf=0.47 (30% EtOAc/Hexane)

$^1$HNMR(CDCl$_3$)δ11.40(s,1), 9.71(s,1), 7.26(s,1), 6.42(s,1), 4.18(t,2,J=5.80 Hz), 3.77(t,2,J=6.28 Hz), 2.57(q,2,J=7.41 Hz), 2.30(m,2), 1.96(t,3,J=7.54 Hz)

IR (CHCl$_3$) 3021, 2971, 2937, 1643, 1586, 1494 cm$^{-1}$

Mass Spec(FD) m/e 243 (M+)

Elem Anal Calc'd for C$_{12}$H$_{15}$O$_3$Cl:

C,59.33; H, 6.23; Cl,14.61;

Found C,59.24; H, 6.18; Cl,14.69.

C. Preparation of 1-Benzyloxy-3-[3-chloropropoxy]-4-ethyl6- formyl benzene.

A suspension of hexane washed NaH (2.40 g of 60% oil dispersion, 60 mmol) in dry DMF was stirred under argon atmosphere at room temperature. A 50 mL dry DMF solution of 1-(3-chloropropoxy-1-yl)-3-hydroxy-4-formyl-5-ethyl benzene (6.92 g, 28.6 mmol) was added slowly to the NaH suspension, and this mixture was stirred for 30 min at room temperature. Benzyl bromide (9.78 g, 57.2 mmol) was added to the alkoxide solution and stirring was continued at room temperature. After three hours the reaction was carefully quenched with saturated NH$_4$Cl solution and then the reaction was diluted with water and extracted several times with EtOAc. The organic extract was washed with water and dried over MgSO$_4$. Filtration and solvent removal gave a yellow solid. The solid was purified by Waters Prep 500 chromatography using a silica gel support and eluting with a solvent gradient of 5% to 40% EtOAc/Hexane over a 45 min period. The desired product was obtained as a white solid (7.14 g, 75%).

TLC Rf=0.34 (30% EtOAc/Hexane)

$^1$HNMR(CDCl$_3$)δ10.41(s,1) 7.68(s,1) 7.42(m,5) 6.49(s,1) 5.20 (s,2), 4.17 (t,2,J=5.78 Hz), 3.78 (t,2,J=6.22 Hz), 2.57 (q,2,J=7.53 Hz), 2.29 (m,2), 1.18 (t,3,J=7.50 Hz)

IR(CHCl$_3$) 3013, 2971, 2875, 1667, 1607, 1505, 1465 cm$^{-1}$

Mass Spec(FD) m/e 332 (M+)

Elem Anal Calc'd for C$_{19}$H$_{21}$O$_3$Cl:

C,68.57; H,6.36; Cl,10,65;

Found C, 68.68; H, 6.54; Cl,10,53.

D. Preparation of 1-Benzyloxy-3-[3-chloropropoxy]-4-ethyl6- hyroxybenzene.

A solution of the aldehyde in CH$_2$Cl$_2$ (0.18M) at room temperature was treated with m-chloroperbenzoic acid (1.1 eqv), and the reaction was stirred at room temp. After 30 min. a ppt formed. The reaction was complete after 5 h. The precipitate was removed by filtration. The solvent was removed under vacuum and the resulting solid was dissolved in THF (0.28M) and stirred overnight with 2N NaOH (2.5 eqv). Subsequently, the THF was removed under vacuum, and the resulting aqueous mixture was diluted with H$_2$O and acidified to pH 1 with 1N HCl. The milky suspension was extracted several times with EtOAc. The organic extract was washed several times with saturated aqueous NaHCO$_3$ solution and then with brine. The organic layer was dried over MgSO$_4$. Filtration and solvent removal gave 8.70 g of a brown oil. The oil was purified by silica gel chromatography.

1-Benzyloxy-2-[3-chloropropoxy]-4-ethyl-6-hyroxybenzene was obtained in 66% yield from 1-Benzyloxy-2-[3-chloropropoxy]-4-ethyl-6-formylbenzene.

TLC Rf=0.46 (30% EtOAc/Hexane)

$^1$HNMR(CDCl$_3$)δ7.44(m,5), 6.79(s,1), 6.58(s,1), 5.25(s,1), 5.10 (s,2), 4.03 (t,2,J=5.77 Hz), 3.78 (t,3,J=6.36 Hz), 2.56(q,2,J=7.56 Hz), 2.23(m,2), 1.17(t,3,J=7.59 Hz).

IR(CHCl$_3$) 3552, 3012, 2969, 2934, 1511, 1469 cm$^{-1}$

Mass Spec (FAB) m/e 320 (M+)

Elem Anal Calc'd for C$_{18}$H$_{21}$O$_3$Cl:

C,67.39; H,6.60; Cl,11.05;

Found C, 67.09; H, 6.56; Cl,10.82.

E. Preparation of 1-Benzyloxy-3-[3-chloropropoxy]-4-ethyl-6-ethoxy benzene.

A suspension of hexane washed NaH (2.10 eqv) in dry DMF (1.3M soln) was stirred under argon atm. at room temp. A solution of the phenol in dry DMF (0.15M) was added slowly to the NaH suspension. The reaction was stirred at room temp for 30 min. 18-Crown-6 was added to the reaction followed by the dropwise addition of alkyl halide (5.0 eqv). After stirring at room temp for several hours the reaction was quenched with saturated aqueous NH$_4$Cl solution, diluted with water and extracted with EtOAc. The EtOAc extract was washed with water and then dried over MgSO$_4$. Filtration and solvent gave the crude product which was purified by silica gel flash chromatography.

1-Benzyloxy-2-[3-chloropropoxy]-4-ethyl-6-ethoxy benzene was prepared in 77% yield as a white solid from 1-Benzyloxy-2-[3-chloropropoxy]-4-ethyl-6-hydroxy benzene and ethyliodide.

TLC Rf=0.48 (30% EtOAc/Hexane)

$^1$HNMR(CDCl$_3$)δ7.40(m,5), 6.80(s,1), 6.56(s,1), 5.16(s,2), 4.10(q,2,J=6.97 Hz), 4.00(t,2,J=5.70 Hz), 3.77(t, z, J=6.73 Hz), 2.60(q,2,J=7.50 Hz), 2.21(m,2), 1.43(t,3,J=6.97 Hz), 1.20 (t,3 ,J=7.46 Hz)

IR(CHCl$_3$) 3011, 2971, 2950, 2890, 1620, 1507, 1471 cm$^{-1}$

Mass Spec(FAB) m/e 348(M+)

Elem Anal Calc'd for C$_{20}$H$_{25}$O$_3$Cl:

C,68.86; H,7.22;

Found C,69.35; H,7.38.

F. Preparation of Chromone

To a solution of 225 mL of EtOH(Abs) under argon atm. and at room temp added 16.56 g of Na metal over a 1 h. period. After all of the Na was added the reaction mixture was refluxed for 1 h. then cooled to room temp. A mixture of 2,4-dihydroxyacetophenone (34.82 g, 0.180 mol), diethyloxylate (54.57 mL, 0.41 mol ), absolute EtOH (45 mL ), and diethylether (45 mL) was added to the sodium ethoxide solution over 25 min. The resulting deep maroon reaction mixture was then refluxed for 2.5 h and then cooled to room temp. The reaction mixture was poured into approx. 600 mL of 1N HCl and then extracted several times with $Et_2O$. The ether was removed form the extract and the resulting gum was dissolved in 135 mL of EtOH. To this solution was then added 2.25 mL of conc. HCl and subsequently refluxed for 45 min. The reaction was cooled to room temp and EtOH was removed under reduced pressure leaving a brown solid. This solid was dissolved in EtOAc and washed 1 x with H2O, 2 x's with sat'd $NaHCO_3$, 1 x with $H_2O$ and then dried over $MgSO_4$. Filtration and solvent removal gave 87 g of a brown solid which was recrystallized from EtOAc/petroleum ether. Recrystallization provided 24.07 g (48%) of a tan solid chromone.

TLC: Rf=0.27 (40% EtOAc/Hexane).

$^1$H NMR $(CDCl_3)\delta8.80$ (s(br), 1), 7.98 (d,1,J=8.78 Hz), 7.13 (d,1,J=8.78 Hz), 7.13(s,1), 4.47 (q,2,J=7.11 Hz), 2.96 (t,2,J=7.25 Hz), 1.73 (m,2), 1.46 (t,3,J=7.16 Hz), 1.02 (t,3,J=7.11 Hz).

G. Preparation of Ethyl 3,4-dihydro-8-propyl-2H-1-benzopyran-2-carboxylate.

In a parr bottle, chromone (12.07 g, 0.044 mol) was dissolved in 210 mL of acetic Acid. 10% Pd/C (7.2 g) catalyst was added to this solution and the bottle was pressurized with 52 psi of $H_2$ gas. The reaction was agitated for 23 h. The catalyst was removed by filtration through a celite pad in a sintered glass funnel. The catalyst was washed with EtOAc. The solvent was removed from the filtrate and the resulting oil was azeotroped with toluene providing 12 g of brown oil. The material was purified on a Waters Prep 500 HPLC, equiped with silica gel cartridges, running a 5% to 40% EtOAc/Hexane gradient over 50 min at a flow rate of 250 mL/min and collecting 500 mL fractions. The purified chroman was obtained as a pink oil (10 g, 86%).

TLC: Rf=0.50 (40% EtOAc/Hexane).

$^1$H NMR $(CDCl_3)\delta6.73$ (d,1,J=8.20 Hz), 6.37 (d,1,J=8.20 Hz), 4.78 (s(br), 1), 4.75 (m,1), 4.25 (m,2), 2.68 (m, 4), 2.16 (m,2), 1.60 (m,2), 1.29 (t,3,J=7.07 Hz), 0.99 (t,3,J=7.34 Hz).

H. Preparation of ethyl [3-[(1-benzyloxy-4-ethyl-2-ethoxy-5-yl)oxy]propoxy]-3,4-dihydro-8-propyl-2H-l-benzopyran-2-carboxylate.

To a solution of 1-benzyloxy-3-[3-chloropropoxy]-4-ethyl-6-ethoxy benzene (1.0 g, 2.87 mmol) in acetone (8.0 mL) and under argon atmosphere, added NaI (4.31 g, 28.7 mmol). The reaction mixture was refluxed for 8 h and then cooled to room temperature. The acetone was removed from the reaction mixture under vacuum, and the residue was dissolved in diethylether and washed with water. The ether extract was dried over $MgSO_4$ and filtered. Solvent removal gave 1.09 g of the iodide as a yellow oil which solidified on standing at $-4°$ C.

Under argon atmosphere and at room temperature, a mixture of ethyl 3,4-dihydro-8-propyl-2H-l-benzopyran-2-carboxylate (0.545 g, 2.06 mmol) and $K_2CO_3$ (0.854 g,6.18 mmol) in 4.0 mL of dry DMF was treated with a 4.0 mL DMF solution of the above prepared iodide.

After stirring at room temp for 42 h the reaction was quenched with water and then extracted several times with ethyl acetate. The ethyl acetate extract was washed with water and then dried over $MgSO_4$. Filtration and solvent removal gave 1.30 g of a yellow oil. The oil was purified by flash chromatography on silica gel eluting with 20% EtOAc/Hexane. The desired coupled product (0.932 g) was obtained in 79% yield as a yellow oil.

TLC Rf=0.48 (30% EtOAc/Hexane)

$^1$HNMR$(CDCl_3)\delta7.43$ (m,5), 6.85(d,1,J=8.37 Hz), 6.82 (s,1), 6.60(s,1), 6.50(d,1,J=8.37 Hz), 5.13(s,2), 4.78(m,1), 4.26(m,2), 4.13(m,6), 2.67(m,6), 2.24(m,4), 1.62(m,2), 1.46 (t,3,J=7.00 Hz), 1.32 (t,3,J=7.09 Hz), 1.21 (t,3 ,J=7.47 Hz), 0.98 (t,3,J=7.34 Hz )

IR$(CHCl_3)$ 3027, 3010, 2966, 2930, 2867, 1750, 1611, 1507, 1469 cm$^{-1}$

Mass Spec (FAB) m/e 486 (M+)

Elem Anal Calc'd for $C_{35}H_{44}O_7$:

C,72.89; H,7.69;

Found C, 72.85; H, 7.40.

I. Preparation of Ethyl [3-[(6-ethyl-4-ethoxy-3-hydroxy-1-yl)oxy]propoxy]-3,4-dihydro-8-propyl-2H-l-benzopyran-2carboxylate.

To a solution of the benzyl ether in ethyl acetate or methanol (0.14M solution) was added 10% Pd/C (15% w/w). Hydrogen gas was bubbled through this solution for 15 min.

The reaction was then stirred at room temp under an atmosphere of hydrogen. After starting material was consumed, argon was bubbled through the reaction mixture for 15 min. The reaction mixture was filtered through a celite pad in a sintered glass funnel, and the catalyst was washed with EtOAc. The resulting crude product was purified by flash chromatography using silica gel as the solid support and eluting with an ethyl acetate/hexane mixture.

Ethyl [3-[(6-ethyl-4-ethoxy-3-hydroxy-1-yl)oxy]-propoxy]-3,4-dihydro-8-propyl-2H-l-benzopyran-2-carboxylate was prepared from ethyl [3-[(1-benzyloxy-4-ethyl-2-ethoxy)-5-yl)oxy]propoxy]-3,4-dihydro -8-propyl-2H-1-benzopyran-2 -carboxylate in 87% yield as a white solid.

TLC Rf=0.32 (30% EtOAc/Hexane)

$^1$HNMR$(CDCl_3)\delta6.85$(d,1,J=8.37 Hz), 6.74(s,1), 6.62(s,1), 6.52(d,1,J=8.37 Hz), 4.79(m,1), 4.19(m,8), 2.68(m,8), 2.26(m,4), 1.62(m,2), 1.45(t,3,J=6.96 Hz), 1.33(t,3,J=7.14 Hz), 1.21(t,3,J=7.54 Hz), 1.00(t,3,J=7.33 Hz)

IR$(CHCl_3)$ 3540, 3026, 2965, 2934, 2873, 1750, 1611, 1509, 1492 cm$^{-1}$

Mass Spec (FD) m/e 486 (M+)

Elem Anal Calc'd for $C_{28}H_{38}NO_7$:

C,69.11; H,7.87;

Found C,69.00; H,8.00.

J. Preparation of 3,4-dihydro-8-propyl-7-[3-(2-ethyl-5-hydroxy-4-ethoxy-phenoxy)propoxy]-2H-l-benzopyran-2-carboxylic acid.

The ethyl ester was stirred in dioxane (0.14M solution) at room temperature. This solution was treated with 3.0 eqv of NaOH (2N aq solution). The reaction was stirred at room temperature for 2.5 h and then the dioxane was removed under vacuum. The resulting residue was dissolved in water and acidified to pH 1 with 5N HCl (a white ppt. forms). The aqueous mixture was extracted several times with ethyl acetate and then dried over MgSO4. Filtration and solvent removal gave the crude product.

3,4-dihydro-8-propyl-7-[3-(2-ethyl-5-hydroxy-4-ethoxyphenoxy)propoxy]-2H-1-benzopyran-2-carboxylic acid was purified by recrystallization from EtOAc/-Hexane. The desired acid was obtained as white crystals (0.436 g, 71%)

TLC Rf=0.49 (6.5/3.4/0.1 EtOAc/Hexane/AcOH)

$^1$HNMR(CDCl$_3$)δ6.84(d,1,J=8.44 Hz), 6.69(s,1), 6.56(s,1), 6.50(d,1,J=8.44 Hz), 5.65(s(br),1), 4.77(dd, 1,J=7.62, 3.72 Hz), 4.10(m,6), 2.77(m,2), 2.62(m,4), 2.22(m,4), 1.54(m,2), 1.42(t,3,J=6.98 Hz), 1.16(t,3,J=7.48 Hz), 0.94(t,3,J=7.30 Hz)

IR(KBr) 3215(br), 2956, 2930, 2870, 1706, 1613, 1589, 1516 cm$^{-1}$

Mass Spec(FD) m/e 458(M+)

Elem Anal Calc'd for $C_{26}H_{34}O_7$:

C,68.10; H,7.47;

Found C,68.13; H,7.56.

The compounds of Formula I should be useful in treating any condition, including clinical conditions, which is characterized by the excessive release of leukotriene B$_4$. These conditions include immediate type hypersensitivity reactions such as asthma. The term "excessive release" of leukotriene B$_4$ refers to an amount of the leukotriene sufficient to cause the particular condition associated with such amount. The amount of leukotriene which is considered to be excessive will depend on a variety of factors, including the amount of leukotriene required to cause the particular condition, and the species of the mammal involved. As will be appreciated by those skilled in the art, the success of treating a mammal suffering from or susceptible to a condition characterized by an excessive release of leukotriene with a compound of Formula I will be measured by the regression or prevention of the symptoms of the condition.

Inhibition of [$^3$H]-LTB$_4$ Binding to Human Neutrophils.

The effectiveness of the compounds of the present invention to inhibit binding of [$^3$H]-LTB$_4$ to human neutrophils was measured by using an adaptation of a radioligand binding assay developed by Goldman, D. W. and Goetzl, E. J.: Specific binding of leukotriene B$_4$ to receptors on human polymornuclear leukocytes. J. Immunol. 129: 1600–1604(1982). Heparinized venous blood was drawn from normal human volunteers and neutrophils isolated by standard techniques of Ficoll-Hypaque centrifugation, dextran 70 sedimentation and hypotonic lysis. Cell preparations were ≧90% neutrophils and ≧90% viable. The binding assay was carried out in silanized 12×75 mm glass tubes by adding in the following order: 10 μl DMSO containing different amounts of test compound,20 μl of 2.65 nM [$^3$H]-LTB$_4$ and 500 μl of the cells suspended in Hanks' balanced salt solution containing 0.1% ovalbumin (2×10$^7$ cells/ml). Tubes were incubated at 4° C. for 10 minutes and the reaction terminated by isolating the cells with a Brandel MB-48R harvester. Radioactivity bound to the cells was measured by scintillation spectrometry. Nonspecific binding was determined by measuring the amount of label bound when a greater than 2000-fold excess of nonradioactive ligand was added. Appropriate corrections for nonspecific binding were made when analyzing the data. The concentration of DMSO in the incubation mixture (1.9%) had no effect on the binding of radioligands. Data were analyzed using linear regression analysis of log-logit plots of the values between 10% and 90% of control binding to calculate IC$_{50}$'s.

The effectiveness of compounds of Formula I to inhibit the binding of tritiated LTB$_4$ to guinea pig lung membranes was determined as follows.

[$^3$H]-LTB$_4$ Radioligand Binding Assay in Guinea Pig Lung Membranes

[$^3$H]-LTB$_4$ (196–200 Ci/mmole) was purchased from New England Nuclear (Boston, Mass.). All other materials were purchased from Sigma (St. Louis, Mo.). Incubations (555 mL) were performed in polypropylene minitubes for 45 minutes at 30° C. and contained 25 mg of guinea pig lung membrane protein (Saussy, et al., Mol. Pharmacol., 39, 72 (1991)) in a buffer containing 25 mM MOPS, 10 mM MgCl$_2$, 10 mM CaCl$_2$, pH 6.5, approximately 140 pM [$^3$H]-LTB$_4$, and displacing ligand or vehicle (0.1% DMSO in 1 mM sodium carbonate, final concentration) as appropriate. The binding reaction was terminated by the addition of 1 mL ice cold wash buffer (25 mM Tris-HCl, pH 7.5) followed immediately by vacuum filtration over Whatman GF/C glass fiber filters using a Brandel (Gaithersburg, Md.) 48 place harvester. The filters were washed three times with 1 mL of wash buffer. Retained radioactivity was determined by liquid scintillation counting at 50% counting efficiency using Ready Protein Plus cocktail (Beckman, Fullerton, Calif.). Nondisplaceable binding was determined in the presence of 1 mM LTB$_4$ and was usually less than 10% of total binding. Data were analyzed using linear regression analysis of log-logit plots of the values between 10% and 90% of control binding to calculate IC$_{50}$s and slope factors (pseudo-Hill coefficients). IC$_{50}$ values thus obtained were corrected for radioligand concentration (Cheng and Prusoff, Biochem. Pharmacol., 22, 3099 (1973)) to calculate K$_i$ values. The data reported below is the average -log K$_i$, otherwise known as the pKi, for n experiments.

TABLE I

| Compound of Example No. | Binding Human Neutrophils IC50 (nM) | Binding Guinea Pig Lung pKi (n) |
|---|---|---|
| 1 | 6.0 | 7.64 ± 0.16 (4) |
| 2 | 4.8 | 7.91 ± 0.10 (7) |
| 3 | 6.6 | 7.67 ± 0.13 (3) |
| 4 | 12 | 7.39 ± 0.13 (7) |
| 5 | 36 | 7.13 ± 0.09 (7) |
| 6 | 42 | 7.11 ± 0.14 (4) |
| 7 | 885 | 6.66 ± 0.13 (4) |
| 8 | 31 | 6.96 ± 0.02 (3) |
| 9 | 2.9 | 8.82 ± 0.25 (3) |
| 10 | 4.2 | 8.89 ± 0.20 (8) |

As noted above, the compounds of the present invention are useful as selective leukotriene B$_4$ antagonists. Therefore, another embodiment of the present invention is a method of treating a mammal suffering from or susceptible to a condition characterized by an excessive release of leukotriene B$_4$ which comprises administering an effective amount of a compound according to Formula I or a pharmaceutically acceptable salt thereof.

The term "effective amount" as used herein, means an amount of a compound of the present invention which is capable of regressing or preventing the symptoms of the condition. The leukotriene antagonism contemplated by the present method includes both medical therapeutic and/or prophylactic treatment, as appropriate. The specific dose of compound administered according to this invention will, of course, be determined by the particular circumstances surrounding the case, including, for example, the compound administered, the route of administration, and the condition being treated. A typical daily dose will contain from about 0.1 mg/kg to about 300 mg/kg of the active compound of this invention. Preferred daily doses generally will be from about 0.5 to about 20 mg/kg.

The compounds can be administered by a variety of routes including oral, rectal, transdermal, subcutaneous, intravenous, intramuscular, and intranasal.

A variety of physiologic functions have been associated with leukotriene $B_4$. As such, the compounds of this invention are believed to have the ability to treat in mammals a variety of disorders associated with leukotriene $B_4$ such as asthma and allergic diseases, (including allergic rhinitis), inflammatory bowel disease, psoriasis, ischemia, shock, adult respiratory distress syndrome and arthritis. Therefore, the present invention also provides methods of treating the above disorders at the rates set forth above for antagonizing leukotriene $B_4$ by administering an asthma, allergic disease, inflammatory bowel disease, psoriasis, shock, ischemia, adult respiratory distress syndrome or arthritis relieving dose of a compound of the present invention.

The compounds of the present invention are preferably formulated prior to administration. Therefore, another embodiment of the present invention is a pharmaceutical formulation comprising an effective amount of a compound of Formula I or a pharmaceutically acceptable salt thereof and a pharmaceutically acceptable carrier, diluent or excipient therefor.

The active ingredient in such formulations comprises from 0.1% to 99.9% by weight of the formulation. By pharmaceutically acceptable it is meant the carrier, diluent or excipient must be compatible with the other ingredients of the formulation and not deleterious to the recipient thereof.

The present pharmaceutical formulations are prepared by known procedures using well known and readily available ingredients. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), ointments containing, for example, up to 10% by weight of the active compound, soft and hard gelatin capsules, suppositories, sterile injectable solutions, sterile packaged powders, and the like.

Examples of suitable carriers, excipients, and diluents are lactose, dextrose, sucrose, sorbitol, mannitol, starches, gumacacia, calcium phosphate, alginates, tragacanth, gelatin, calcium silicate, microcrystalline cellulose, polyvinylpyrrolidone, cellulose, water syrup, methyl cellulose, methylhydroxybenzoates, propylhydroxybenzoates, talc, magnesium stearate and mineral oil. The formulations may additionally include lubricating agents, wetting agents, sweetening agents, flavoring agents, and the like. The compositions of the invention may be formulated so as to provide quick, sustained or delayed release of the active ingredient after administration to the patient by employing procedures well known in the art.

The compositions are preferably formulated in a unit dosage from, each dosage generally containing form about 0.1 to about 300 mg, and preferably from about 1 to about 250 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The following formulation examples are illustrative only and are not intended to limit the scope of the invention in any way. "Active ingredient," of course, means a compound according to Formula I or a pharmaceutically acceptable salt thereof.

Formulation 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

The above ingredients are mixed and filled into hard gelatin capsules in 460 mg quantities.

Formulation 2

A tablet is prepared using the ingredients below:

|  | Quantity (mg/capsule) |
| --- | --- |
| Active ingredient | 250 |
| Cellulose, microcrystalline | 400 |
| Silicon dioxide, fumed | 10 |
| Stearate acid | 5 |
| Total | 665 mg |

The components are blended and compressed to form tablets each weighing 665 mg.

Formulation 3

An aerosol solution is prepared containing the following components:

|  | Quantity (mg/capsule) |
| --- | --- |
| Active ingredient | 250 |
| Cellulose, microcrystalline | 400 |
| Silicon dioxide, fumed | 10 |
| Stearate acid | 5 |
| Total | 665 mg |

The active compound is mixed with ethanol and the mixture added to a portion of the propellant 22, collected to −30° C. and transferred to a filling device. The required amount ks then fed to a stainless steel container and diluted with the remainder of the propellant. The valve units are then fitted to the container.

Formulation 4

Tablets, each containing 60 mg of active ingredient, are made as follows:

|  |  |
|---|---|
| Active ingredient | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate starch | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

|  |  |
|---|---|
| Active ingredient | 80 mg |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

|  |  |
|---|---|
| Active ingredient | 225 mg |
| Saturated fatty acid glycerides | 2,000 mg |
| Total | 2,225 mg. |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, such containing 50 mg of active ingredient per 5 ml dose, are made as follows:

|  |  |
|---|---|
| Active ingredient Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

|  |  |
|---|---|
| Active ingredient | 100 mg |
| Isotonic saline | 1,000 ml |

The solution of the above ingredients generally is administered intravenously to a subject at a rate of 1 ml per minute.

I claim:

1. A compound of the Formula

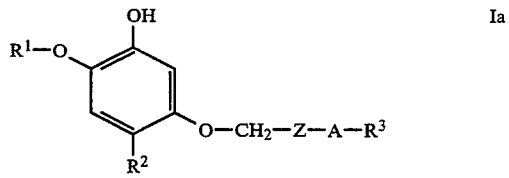

and pharmaceutically acceptable base addition salts thereof, wherein $R_1$ is $C_1$–$C_6$ alkyl, or $C_5$–$C_6$ cycloalkyl; $R^2$ is $C_1$–$C_4$ alkyl; Z is $C_2$–$C_4$ alkylidene; A is —O—, —$CH_2$—, or —$C(CH_3)_2$—; $R^3$ is —COOH, 5-tetrazolyl or a bicyclic group having the structure

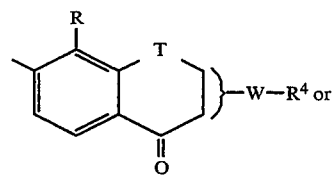

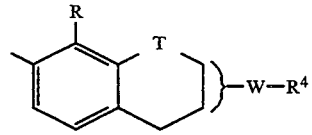

where
R is n-propyl,
T is —O—,
W is a bond, and $R^4$ is —COOH or 5-tetrazolyl.

2. The compound of claim 1 which is 4-ethyl-2-methoxy-5-[[6-methyl-6-(2H-tetrazol-5-yl)heptyl]oxy]-phenol or a pharmaceutically acceptable base addition salt thereof.

3. The compound of claim 1 which is 3,4-dihydro-8-propyl-7-[3-(2-ethyl-5-hydroxy-4-methoxy-phenoxy)propoxy]-2H-1-benzopyran-2-carboxylic acid or a pharmaceutically acceptable base addition salt thereof.

4. The compound of claim 1 which is 4-ethyl-2-ethoxy-5-[[6-methyl-6-(2H-tetrazol-5-yl)heptyl]oxy]-phenol or a pharmaceutically acceptable base addition salt thereof.

5. The compound of claim 1 which is 3,4-dihydro-8-propyl-7-[3-(2-ethyl-5-hydroxy-4-ethoxy-phenoxy)-propoxy]-2H-1-benzopyran-2-carboxylic acid or a pharmaceutically acceptable base addition salt thereof.

6. A method of treating a mammal suffering from or susceptible to any condition characterized by an excessive release of leukotrienes, which comprises administering to said mammal a leukotriene antagonizing amount of a compound of claim 2 or a pharmaceutically acceptable base addition salt thereof.

7. A method of treating a mammal suffering from or susceptible to any condition characterized by an excessive release of leukotrienes, which comprises administering to said mammal a leukotriene antagonizing amount of a compound of claim 2 or a pharmaceutically acceptable base addition salt thereof.

8. The method of claim 7 employing 4-ethyl-2-methoxy-5-[[6-methyl-6-(2H-tetrazol-5-yl)heptyl]oxy]-phenol or a pharmaceutically acceptable base addition salt thereof.

9. The method of claim 8 employing 3,4-dihydro-8-propyl-7-[3-(2-ethyl-5-hydroxy-4-methoxy-phenoxy)-propoxy]-2H-1-benzopyran-2-carboxylic acid or a pharmaceutically acceptable base addition salt thereof.

10. The method of claim 8 employing 4-ethyl-2-ethyl-5-[[6-methyl-6-(2H-tetrazol-5-yl)heptyl]oxy]phenol or a pharmaceutically acceptable base addition salt thereof.

11. The method of claim 8 employing 3,4-dihydro-8-propyl-7-[3-(2-ethyl-5-hydroxy-4-ethoxy-phenoxy)-propoxy]-2H-1-benzopyran-2-carboxylic acid or a pharmaceutically acceptable base addition salt thereof.

12. A method of treating a mammal suffering from or susceptible to an immediate hypersensitivity reaction of the type represented by asthma, which comprises administering to said mammal a therapeutically-effective amount of a compound of claim 2 or a pharmaceutically acceptable base addition salt thereof.

13. A method of treating a mammal suffering from or susceptible to an immediate hypersensitivity reaction of the type represented by asthma, which comprises administering to said mammal a therapeutically-effective amount of a compound of claim 1 or a pharmaceutically acceptable base addition salt thereof.

14. The method of claim 13 employing 4-ethyl-2-methoxy-5-[[6-methyl-6-(2H-tetrazol-5-yl)heptyl]oxy]-phenol or a pharmaceutically acceptable base addition salt thereof.

15. The method of claim 13 employing 3,4-dihydro-8-propyl-7-[3-(2-ethyl-5-hydroxy-4-methoxy-phenoxy)-propoxy]-2H-1-benzopyran-2-carboxylic acid or a pharmaceutically acceptable base addition salt thereof.

16. The method of claim 13 employing 4-ethyl-2-ethoxy-5-[[6-methyl-6-(2H-tetrazol -5-yl)heptyl]oxy]-phenol or a pharmaceutically acceptable base addition salt thereof.

17. The method of claim 13 employing 3,4-dihydro-8-propyl-7-[3-(2-ethyl-5-hydroxy-4-ethoxy-phenoxy)-propoxy]-2H-1-benzopyran-2-carboxylic acid or a pharmaceutically acceptable base addition salt thereof.

18. A pharmaceutical formulation comprising a compound of claim 2 or a pharmaceutically acceptable base addition salt thereof in association with a pharmaceutically acceptable carrier.

19. A pharmaceutical formulation comprising a compound of claim 1 or a pharmaceutically acceptable base addition salt thereof in association with a pharmaceutically acceptable carrier.

20. A formulation according to claim 19 wherein said compound is 4-ethyl-2-methoxy-5-[[6-methyl-6-(2H-tetrazol-5-yl)heptyl]oxy]phenol or a pharmaceutically acceptable base addition salt thereof.

21. A formulation according to claim 19 employing 3,4-dihydro-8-propyl-7-[3-(2-ethyl-5-hydroxy-4-methoxyphenoxy)propoxy]-2H-1-benzopyran-2-carboxylic acid or a pharmaceutically acceptable base addition salt thereof.

22. A formulation according to claim 19 wherein said compound is 4-ethyl-2-ethoxy-5-[[6-methyl-6-(2H-tetrazol-5-yl)heptyl]oxy]phenol or a pharmaceutically acceptable base addition salt thereof.

23. A formulation according to claim 19 wherein said compound is 3,4-dihydro-8-propyl-7-[3-(2-ethyl-5-hydroxy-4-ethoxy-phenoxy)propoxy]-2H-1-benzopyran-2-carboxylic acid or a pharmaceutically acceptable base addition salt thereof.

* * * * *

UNITED STATES PATENT AND TRADEMARK OFFICE
CERTIFICATE OF CORRECTION

PATENT NO. : 5,352,690

DATED : October 4, 1994

INVENTOR(S) : Michael J. Sofia

It is certified that error appears in the above-indentified patent and that said Letters Patent is hereby corrected as shown below:

Column 59, line 33 reads "The method of claim 8 employing 4-ethyl-2-ethyl-..."
should read -- The method of claim 8 employing 4-ethyl-2-ethoxy-...--.

Signed and Sealed this

Twenty-fourth Day of December, 1996

Attest:

BRUCE LEHMAN

Attesting Officer     Commissioner of Patents and Trademarks